United States Patent
Keene et al.

(10) Patent No.: US 9,149,483 B2
(45) Date of Patent: Oct. 6, 2015

(54) METHODS FOR TREATMENT OF DISEASES

(71) Applicants: Jeffery L. Keene, St. Louis, MO (US); Dennis P. Riley, Chesterfield, MO (US); Robert A. Beardsley, University City, MO (US)

(72) Inventors: Jeffery L. Keene, St. Louis, MO (US); Dennis P. Riley, Chesterfield, MO (US); Robert A. Beardsley, University City, MO (US)

(73) Assignee: GALERA LABS, LLC, Creve Coeur, MO (US)

( * ) Notice: Subject to any disclaimer, the term of this patent is extended or adjusted under 35 U.S.C. 154(b) by 0 days.

(21) Appl. No.: 13/625,617

(22) Filed: Sep. 24, 2012

(65) Prior Publication Data

US 2013/0079317 A1 Mar. 28, 2013

Related U.S. Application Data

(60) Provisional application No. 61/539,365, filed on Sep. 26, 2011.

(51) Int. Cl.
| | |
|---|---|
| A01N 55/02 | (2006.01) |
| A61K 31/555 | (2006.01) |
| A61K 9/00 | (2006.01) |
| A61K 9/19 | (2006.01) |

(52) U.S. Cl.
CPC .............. *A61K 31/555* (2013.01); *A61K 9/0019* (2013.01); *A61K 9/19* (2013.01)

(58) Field of Classification Search
CPC ...... A61K 31/555; A61K 9/0019; A61K 9/19
See application file for complete search history.

(56) References Cited

U.S. PATENT DOCUMENTS

| | | | |
|---|---|---|---|
| 5,610,293 | A | 3/1997 | Riley et al. |
| 5,637,578 | A | 6/1997 | Riley et al. |
| 5,874,421 | A | 2/1999 | Riley et al. |
| 5,976,498 | A | 11/1999 | Neumann et al. |
| 6,084,093 | A | 7/2000 | Riley et al. |
| 6,180,620 | B1 | 1/2001 | Salvemini |
| 6,204,259 | B1 | 3/2001 | Riley et al. |
| 6,214,817 | B1 | 4/2001 | Riley et al. |
| 6,245,758 | B1 | 6/2001 | Stern et al. |
| 6,395,725 | B1 | 5/2002 | Salvemini |
| 6,525,041 | B1 | 2/2003 | Neumann et al. |
| 2006/0089710 | A1 | 4/2006 | Richard et al. |
| 2007/0149498 | A1* | 6/2007 | Crapo et al. ............. 514/185 |
| 2009/0131377 | A1 | 5/2009 | Salvemini |
| 2010/0304415 | A1 | 12/2010 | Slomczynska et al. |
| 2011/0136756 | A1 | 6/2011 | Keene et al. |

FOREIGN PATENT DOCUMENTS

WO    WO 2009143454 A2 *  11/2009

OTHER PUBLICATIONS

Goodman & Gilman's the pharmacological basis of therapeutics, 10th Edition, 2001.*
Patent Cooperation Treaty, International Search Report issued for PCT/US2012/056921 on Feb. 22, 2013, 5 pages.
Simic, M. G. et al., "Oxygen Radicals in Biology and Medicine," Basic Life Sciences, vol. 49, Plenum Press, New York and London, 1988.
Weiss et al., "Catalytic Efficacies of Agents that Dismutate Superoxide," J, Cell. Biochem., 1991 Suppl. 15C, 216 Abstract C110, 1991.
Petkau, "Scientific Basis for the Clinical Use of Superoxide Dismutase," Cancer Treat. Rev. 13, 17, 1986.
McCord, "Superoxide Dismutase: Rationale for use in Reperfusion Injury and Inflammation," J. Free Radicals Biol. Med., 2, 307, 1986.
Bannister et al., "Aspects of the Structure, Function, and Applications of Superoxide Dismutase," Crit. Rev. Biochem., 22, 111 (1987).
Gryglewski et al., "Superoxide Anion is Involved in the Breakdown of Endothelium-derived Vascular Relaxing Factor", Nature, vol. 320, pp. 454-456 (1986).
Palmer et al., "Nitric Oxide Release Accounts for the Biological Activity of Endothelium Derived Relaxing Factor", Nature, vol. 327, pp. 523-526 (1987).
Samlowski et al., "A nonpeptidyl mimic of superoxide dismutase, M40403, inhibits dose-limiting hypotension associated with interleukin-2 and increases its antitumor effects," Nature Medicine (2003) 9:750 755.
Riley, D.P., Schall, O.F., "Structure-Activity Studies and the Design of Synthetic Superoxide Dismutase (SOD) Mimetics as Therapeutics," Advances in Inorganic Chemistry, 59, 233-263, 2006.
European Patent Office, Extended Search Report issued for 12835035.2, dated Mar. 9, 2015.
Masini et al., Prevention of antigen-induced early obstruction reaction by inhaled M40419 in actively sensitized guinea-pigs, American Journal of Respiratory and Critical Case Medicine, American Lung Associations, New York, NY, Jan. 1, 2002.
McCarthy, A., Metaphore Pharmaceuticals, Chemistry & Biology, 2003, 10(12): 1139-1140.
Murphy et al., Efficacy of Superoxide Dismutase Mimetic M40403 in Attenuating Radiation-Induced Oral Mucositis in Hamsters, Clin Cancer Res, 2008, 14(13): 4292-4297.
Salvemini et al., A nonpeptidyl mimic of superoxide dismutase with therapeutic activity in rats, Science, 1999, 286: 304-306.
Thompson et al., The manganese superoxide dismutase mimetic, M40403, protects adult mice from lethal total body irradiation, Free Radical Research, 2010; 44(5): 529-540.
Tuder et al., Oxidative stree and apoptosis interative and cause emphsema due to vascular endothelial growth factor receptor blockade, Am. J. Respir. Cell Mol. Biol., 2003, 29: 88-97.

* cited by examiner

*Primary Examiner* — Wu-Cheng Winston Shen
*Assistant Examiner* — Jean Cornet
(74) *Attorney, Agent, or Firm* — Bryan Cave LLP

(57) ABSTRACT

The present disclosure relates to methods of treating a range of diseases or conditions. The methods involve administration of a superoxide dismutase mimetic.

22 Claims, 4 Drawing Sheets

METHODS FOR TREATMENT OF DISEASES

TECHNICAL FIELD

The present invention generally relates to methods for the treatment (including inhibition) of various diseases and conditions. The methods involve the administration of a superoxide dismutase (SOD) mimetic.

BACKGROUND

The enzyme superoxide dismutase catalyzes the conversion of superoxide into oxygen and hydrogen peroxide according to equation (I) (this process is often referred to herein and in the art as dismutation).

$$2O_2^{-} + 2H^{+} \rightarrow O_2 + H_2O_2 \tag{I}$$

Reactive oxygen metabolites derived from superoxide have been demonstrated to contribute to the tissue pathology in a number of inflammatory diseases and disorders, such as reperfusion injury to the ischemic myocardium, inflammatory bowel disease, rheumatoid arthritis, osteoarthritis, atherosclerosis, hypertension, metastasis, psoriasis, organ transplant rejections, radiation-induced injury, asthma, influenza, stroke, burns and trauma. See, for example, Simic, M. G., et al., Oxygen Radicals in Biology and Medicine, BASIC LIFE SCIENCES, vol. 49, Plenum Press, New York and London, 1988; Weiss, J, Cell. Biochem., 1991 Suppl. 15C, 216 Abstract C110 (1991); Petkau, A., Cancer Treat. Rev. 13, 17 (1986); McCord, J. Free Radicals Biol. Med., 2, 307 (1986); and Bannister, J. V., et al., Crit. Rev. Biochem., 22, 11 1 (1987). In certain situations, cells are deficient in natural SOD activity; for example, this may occur as a result of heart attack, organ transplant, and even cancer: cancer cells are often deficient in SOD and can thus permit superoxide concentrations to rise and can cause injury to surrounding tissue.

It is also known that superoxide is involved in the breakdown of endothelium derived vascular relaxing factor (EDRF), which has been identified as nitric oxide (NO), and that EDRF is protected from breakdown by superoxide dismutase. This suggests a central role for activated oxygen species derived from superoxide in the pathogenesis of hypertension, vasospasm, thrombosis and atherosclerosis. See, for example, Gryglewski, R. J. et al., "Superoxide Anion is Involved in the Breakdown of Endothelium-derived Vascular Relaxing Factor", Nature, Vol. 320, pp. 454-56 (1986) and Palmer, R. M. J. et al., "Nitric Oxide Release Accounts for the Biological Activity of Endothelium Derived Relaxing Factor", Nature, Vol. 327, pp. 523-526 (1987).

Clinical trials and animal studies with natural, recombinant and modified superoxide dismutase enzymes have been completed or are ongoing to demonstrate the therapeutic efficacy of reducing superoxide levels in the disease states noted above. However, numerous problems have arisen with the use of the enzymes as potential therapeutic agents, including lack of oral activity (a common problem with polypeptides), short half-lives in vivo, immunogenicity of nonhuman derived enzymes, and poor tissue distribution.

In an effort to overcome the problems associated with superoxide dismutase enzymes, several investigations have been made into the design of non-proteinaceous catalysts for the dismutation of superoxide, and their use in various superoxide-related ailments. One group of catalysts which has been shown to be nearly as effective catalysts as the native superoxide dismutase enzymes are the manganese and iron complexes of pentaazacyclopentadecane ligands, described in U.S. Pat. Nos. 5,610,293, 5,637,578, and 5,874,421. These ligands include a pentaazacyclopentadecane macrocycle with various substituents on the carbons of the macrocycle, or with cyclic or heterocyclic structures attached to the carbons of the macrocycle. Some of these complexes possess potent catalytic superoxide dismutating activity, and produce anti-inflammatory activity and prevent oxidative damage in vivo. In addition, these compounds, which are sometimes referred to as SOD mimetics, have been shown to possess analgesic activity and to reduce inflammation and edema in the rat-paw carrageenan hyperalgesia model, see, e.g., U.S. Pat. No. 6,180,620.

One particular compound that has been demonstrated to be an effective catalysts for the dismutation of superoxide is the following pentaazacyclopentadecane compound, described in the prior art under such names as SC-72325, M40403, KM40403, or (for purposes herein) GC4403:

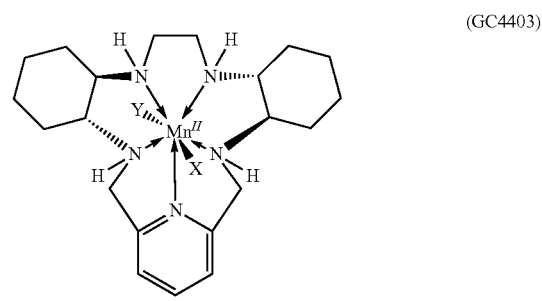

(GC4403)

wherein X and Y are independently neutral or negatively-charged ligands. It is generally known that superoxide dismutase mimetics may be used, per se, as anticancer agents (see, e.g., Simic, M. G., et al., supra; Weiss, supra; Petkau, A., supra, etc.). In addition, it has been reported that combination treatments of the superoxide dismutase mimetic KM4403 with interleukin-2 (IL-2) potentiates the antitumor effect of IL-2. See, Samlowski, W. E., et al., Nature Medicine (2003) 9:750-755.

Although GC4403 has shown efficacy in the treatment of inflammatory conditions such as oral mucositis, there is room for other superoxide dismutase mimetic compounds and treatment methods.

SUMMARY OF THE INVENTION

Among the various aspects of the present disclosure is the provision of methods for the treatment of a range of diseases and conditions, comprising administering to a patient a superoxide dismutase mimetic corresponding to Formula (GC4419):

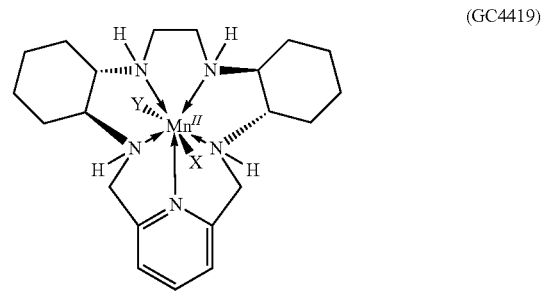

(GC4419)

wherein X and Y are independently neutral or negatively-charged ligands. Pharmaceutical compositions, unit dose formulations, articles of manufacture, and kits are also described herein.

Briefly, therefore, the present disclosure is directed to a unit dose formulation comprising at least 50 mg of a superoxide dismutase mimetic in a container, the superoxide dismutase mimetic corresponding to Formula (GC4419).

Another aspect of the disclosure is directed to an article of manufacture. The article of manufacture comprises packaging material and contained within the packaging material is a parenteral formulation for treating a disease or condition or for protecting tissue against damage resulting from exposure to a cancer treatment in a patient in need thereof. The parenteral formulation comprises a unit dose formulation as described herein and the packaging material comprises a label or package insert with instructions for parenterally administering the dose to the patient.

Another aspect of the disclosure is directed to a pharmaceutical composition in solution form comprising about 0.25 mg/mL to about 3.5 mg/mL of a superoxide dismutase mimetic, the composition being a unit dose in a container for intravenous administration, wherein the superoxide dismutase mimetic corresponds to Formula (GC4419).

Various methods of treatment are also described herein involving the administration of the superoxide dismutase mimetic corresponding to Formula (GC4419).

Thus, another aspect of the disclosure is directed to a method for treating a human patient for tissue damage resulting from the administration of radiation therapy or chemotherapy to the patient. The method comprises administering to the patient a therapeutically effective amount of a superoxide dismutase mimetic corresponding to Formula (GC4419).

Another aspect of the disclosure is directed to a method for treating a human patient for tissue damage resulting from exposure to radiation. The method comprises administering to the patient a therapeutically effective amount of a superoxide dismutase mimetic corresponding to Formula (GC4419).

Another aspect of the disclosure is directed to a method of treating a human patient for a disease or condition, the method comprising administering to the patient, within a 15 minute period, at least 25 mg of a superoxide dismutase mimetic corresponding to Formula (GC4419). Another aspect of the disclosure is directed to a method of treating a human patient for a disease or condition, the method comprising administering to the patient, within a 15 minute period, at least 50 mg of a superoxide dismutase mimetic corresponding to Formula (GC4419). Another aspect of the disclosure is directed to a method of treating a human patient for a disease or condition, the method comprising administering to the patient, within a 30 minute period, at least 50 mg of a superoxide dismutase mimetic corresponding to Formula (GC4419). Another aspect of the disclosure is directed to a method of treating a human patient for a disease or condition, the method comprising administering to the patient, within a 60 minute period, at least 100 mg of a superoxide dismutase mimetic corresponding to Formula (GC4419).

Another aspect of the disclosure is directed to a method of treating a disease or condition in a human patient, the method comprising administering to the patient a superoxide dismutase mimetic at a rate of at least 100 mg/hr, wherein the superoxide dismutase mimetic corresponds to Formula (GC4419). For example, at least 25 mg of a superoxide dismutase mimetic can be administered to the patient at a rate of at least 100 mg/hr.

Another aspect of the disclosure is directed to a method of treating a disease or condition in a human patient, the method comprising administering to the patient a superoxide dismutase mimetic to provide an exposure as measured by an area under the curve (AUC) of at least 4,000 ng-h/mL as calculated from the measurement of the superoxide dismutase mimetic concentration in the patient's plasma, wherein the superoxide dismutase mimetic corresponds to Formula (GC4419).

Other objects and features will be in part apparent and in part pointed out hereinafter.

DETAILED DESCRIPTION

Figure 1:
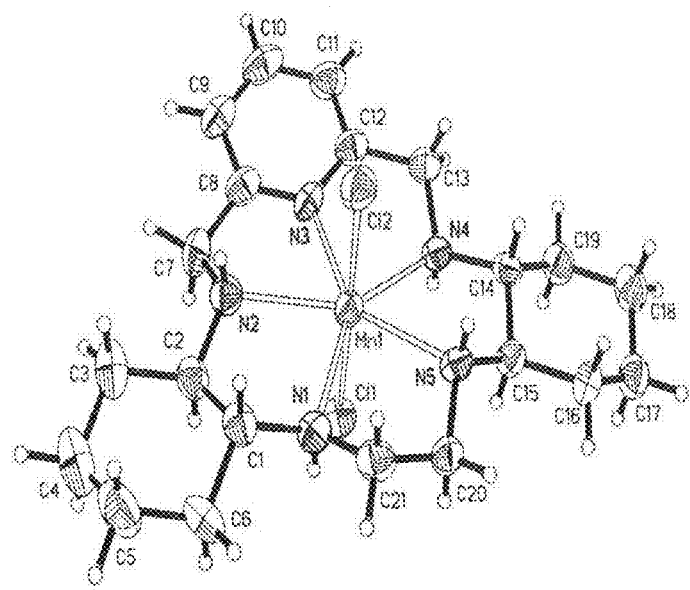
FIG. 1 is the Ortep drawing for the GC4403 complex based on single-crystal X-ray diffraction showing the 50% probability ellipsoids for the non-hydrogen atoms and the hydrogen atoms bound to the secondary amines (see Example 1).

The present disclosure is generally directed to methods and pharmaceutical compositions for the treatment of a range of diseases and conditions. The methods involve the administration of a superoxide dismutase mimetic, or more preferably, a pharmaceutical composition including the superoxide dismutase mimetic, to a subject in need. Pharmaceutical compositions and formulations (such as unit dose formulations) including a superoxide dismutase mimetic and, optionally, a pharmaceutically acceptable carrier, are also described herein. The superoxide dismutase mimetics administered in accordance with the methods described herein (e.g., the compounds corresponding to Formula (GC4419), below) are structurally similar to certain superoxide dismutase mimetics known in the art. Specifically, the chemical structures of GC4403 (such as the dichloro complex form described, for example, in Riley, D. P., Schall, O. F., 2007, *Advances in Inorganic Chemistry*, 59: 233-263) and the compounds of Formula (GC4419) herein (such as the dichloro complex form of Formula (GC4419)), are identical except that they possess mirror image chirality; that is, the enantiomeric structures are non-superimposable.

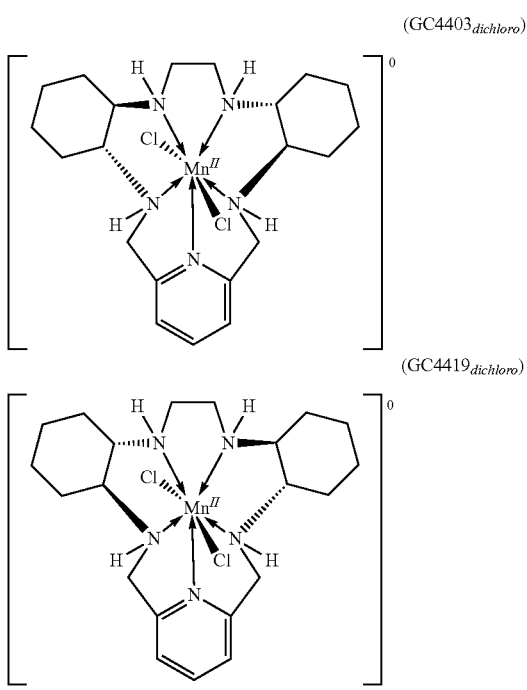

As shown in the above structures, the dichloro complex form of GC4403 has four chiral carbon centers that exist in the R-absolute configuration, while the dichloro complex form of GC4419 has four chiral carbon atoms in the S-absolute configuration.

As detailed in the description and examples herein, these two compounds possess nearly identical physiochemical properties, including stability, reactivity with non-chiral reagents, electronic spectra, solubility in non-chiral media, and reactivity with superoxide (see Example 3, below). Activities in vitro, for example antiproliferative activity of GC4403 and GC4419 in cell culture, are also very similar (see Example 4, below). Despite these similarities, however, it has been surprisingly discovered that the compounds of Formula (GC4419) exhibit a superior safety profile (on the order of five-fold improvement) as compared to the mirror image compound GC4403. By way of example, compounds of Formula (GC4419) may be capable of being administered to a human subject at least 2× more rapidly than GC4403, and at five-fold the dose, with no serious adverse events. Furthermore, this increased safety does not appear at the expense of potency, as compounds of Formula (GC4419) are at least as potent as GC4403 (see Examples 5-9, below).

Superoxide production can be increased in cells (e.g., tumor cells), while native superoxide dismutase expression can be reduced by the cells, leading to elevated superoxide accumulation. The superoxide dismutase mimetics corresponding to Formula (GC4419) can take the place of or supplement native superoxide dismutase and catalyze the conversion of superoxide to hydrogen peroxide, which provides a therapeutic or otherwise beneficial effect. As described in further detail below, in certain embodiments the superoxide dismutase mimetics corresponding to Formula (GC4419) may be administered to increase the capacity of the cells to dismute superoxide.

In various embodiments described herein, the superoxide dismutase mimetics corresponding to Formula (GC4419) may be administered alone or in combination with another (e.g., one or more) pharmaceutically active agent(s) or compound(s). In accordance with certain preferred embodiments, a superoxide dismutase mimetic corresponding to Formula (GC4419) is administered to the subject as the sole pharmaceutically active agent; thus, in one embodiment, for example, the pharmaceutical composition or formulation consists essentially of the superoxide dismutase mimetic corresponding to Formula (GC4419), and optionally (but preferably) includes a pharmaceutically acceptable carrier or excipient. In other embodiments, superoxide dismutase mimetic corresponding to Formula (GC4419) is administered to the subject in combination with another pharmaceutically active agent or compound. In accordance with certain methods described herein, therefore, the superoxide dismutase mimetic corresponding to Formula (GC4419) and the additional pharmaceutically active agent or compound are administered in combination; that is, they can be administered simultaneously (concurrently), or sequentially.

Superoxide Dismutase Mimetics

The superoxide dismutase mimetic compounds that are administered in accordance with the methods described herein are non-proteinaceous molecules that catalyze the conversion of the superoxide radical, $O_2^{-\cdot}$, to molecular oxygen and hydrogen peroxide. In accordance with one embodiment, for example, the superoxide dismutase mimetic is administered to the subject to increase the capacity of cells in the subject (e.g., cancer cells) to dismute superoxide.

The superoxide dismutase mimetics used in the methods, compositions, and formulations disclosed herein, are capable of selectively catalyzing the conversion of superoxide to oxygen and hydrogen peroxide and exhibits no significant activity toward hydrogen peroxide. For example, selective superoxide dismutase mimetics corresponding to Formula (GC4419), below, exhibit no detectable activity towards hydrogen peroxide, whereas non-selective superoxide dismutase mimetics such as mangafodipir, copper [II] diisopropylsalicylate (CuDIPS), manganese [III] tetrakis-(5,10,15,20)-benzoic acid porphyrin (MnTBAP), and the like, exhibit significant activity toward hydrogen peroxide. In general, the efficacy of the superoxide dismutase mimetics employed in the methods described herein tends to decrease as the activity of the superoxide dismutase mimetic toward hydrogen peroxide increases. Accordingly, it is preferred that the ratio of the activity of the superoxide dismutase mimetic toward superoxide to the activity of the superoxide dismutase mimetic toward hydrogen peroxide be at least 10:1 (activity toward superoxide:activity toward hydrogen peroxide). More preferably, the ratio of the activity of the superoxide dismutase mimetic toward superoxide to the activity of the superoxide dismutase mimetic toward hydrogen peroxide is at least 100:1 (activity toward superoxide:activity toward hydrogen peroxide). Still more preferably, the ratio of the activity of the superoxide dismutase mimetic towards superoxide to the activity of the superoxide dismutase mimetic toward hydrogen peroxide is at least 1000:1 (activity toward superoxide: activity toward hydrogen peroxide). In one particularly preferred embodiment, the superoxide dismutase mimetic exhibits no detectable activity toward hydrogen peroxide.

In various aspects of the present disclosure, therefore, the methods described herein involve the administration of a superoxide dismutase mimetic corresponding to Formula (GC4419):

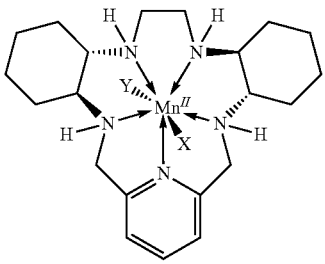

(GC4419)

wherein X and Y in Formula (GC4419) are independently neutral or negatively-charged ligands.

As noted above, X and Y represent suitable neutral or negatively-charged ligands which are derived from any monodentate or polydentate coordinating ligand or ligand system or the corresponding anion thereof (for example benzoic acid or benzoate anion, phenol or phenoxide anion, alcohol or alkoxide anion). For example, X and Y may be independently selected from the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid, aryl carboxylic acid, urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate, aryl thiocarbamate, alkylaryl thiocarbamate, alkyl dithiocarbamate, aryl dithiocarbamate, alkylaryl dithiocarbamate, bicarbonate, carbonate, perchlorate, chlorate, chlorite, hypochlorite, perbromate, bromate, bromite, hypobromite, tetrahalomanganate, tetrafluoroborate, hexafluoroantimonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or the corresponding anions thereof, among other possibilities.

In one embodiment, X and Y are independently selected from monodentate ligands. In a preferred embodiment, for example, X and Y are independently selected from the group consisting of aquo ligands, halo ligands (e.g., chloro, iodo, fluoro), carboxylato ligands (e.g., formato, acetato), thiocyanato ligands, and bicarbonato ligands. In another preferred embodiment, X and Y are independently selected from aquo ligands and halo ligands. In another preferred embodiment, X and Y are independently halo ligands; more preferably in this embodiment X and Y are chloro ligands.

In particularly preferred embodiments, the superoxide dismutase mimetic for use in the methods and compositions described herein corresponds to the dichloro complex form of Formula (GC4419):

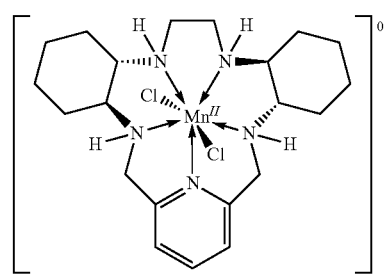

(GC4419$_{dichloro}$)

It will be understood that, when the superoxide dismutase mimetics described herein are dissolved or dispersed in solution such as water or saline, a dynamic and rapid equilibrium is typically established in which the ligands (e.g., chloro ligands) can dissociate with the axial coordination sites being occupied by the solvent (e.g., water) molecules, forming both mono-aquo (monocationic) and bis-aquo (dicationic) complexes. As a result, it is difficult to accurately represent the compound by a single structural formula when in solution. The dissociation reaction generally proceeds in accordance with the following reaction scheme (again, using the chloro and aqua ligands as illustrative examples):

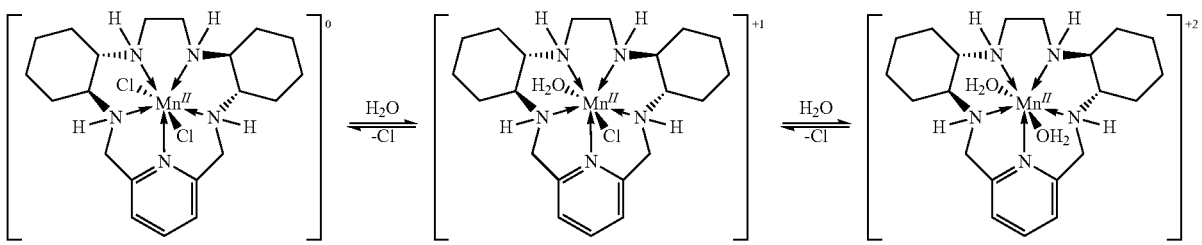

Where the ligands are defined in a particular structure (e.g., where X and Y are chloro ligands, X is aquo and Y is chloro, X and Y are aquo, etc.) the complexes are bracketed and the net charge is shown in the interest of clarity. The rate of exchange of bound/coordinated waters/ligands has been measured by NMR relaxation techniques and is very rapid, e.g., on the order of $10^{+7} s^{-1}$. Due, at least in part, to the rapid rate of exchange of the X and Y ligands in solution, it will be understood that, at a given point in time, the ligands at X and Y will depend on the ligands initially present on the superoxide dismutase mimetic at X and Y (e.g., halo such as chloro, carboxylato such as formato or acetato, or bicarbonato) and any ligands present in the solution in which the compound is dissolved (e.g., water (aquo ligands) or saline (chloro anions), and the like). Thus, in one embodiment, for example, a solution comprising the dichloro complex form of Formula (GC4419) dissolved in buffered saline would be expected to include a mixture of at least the following complexes in equilibrium:

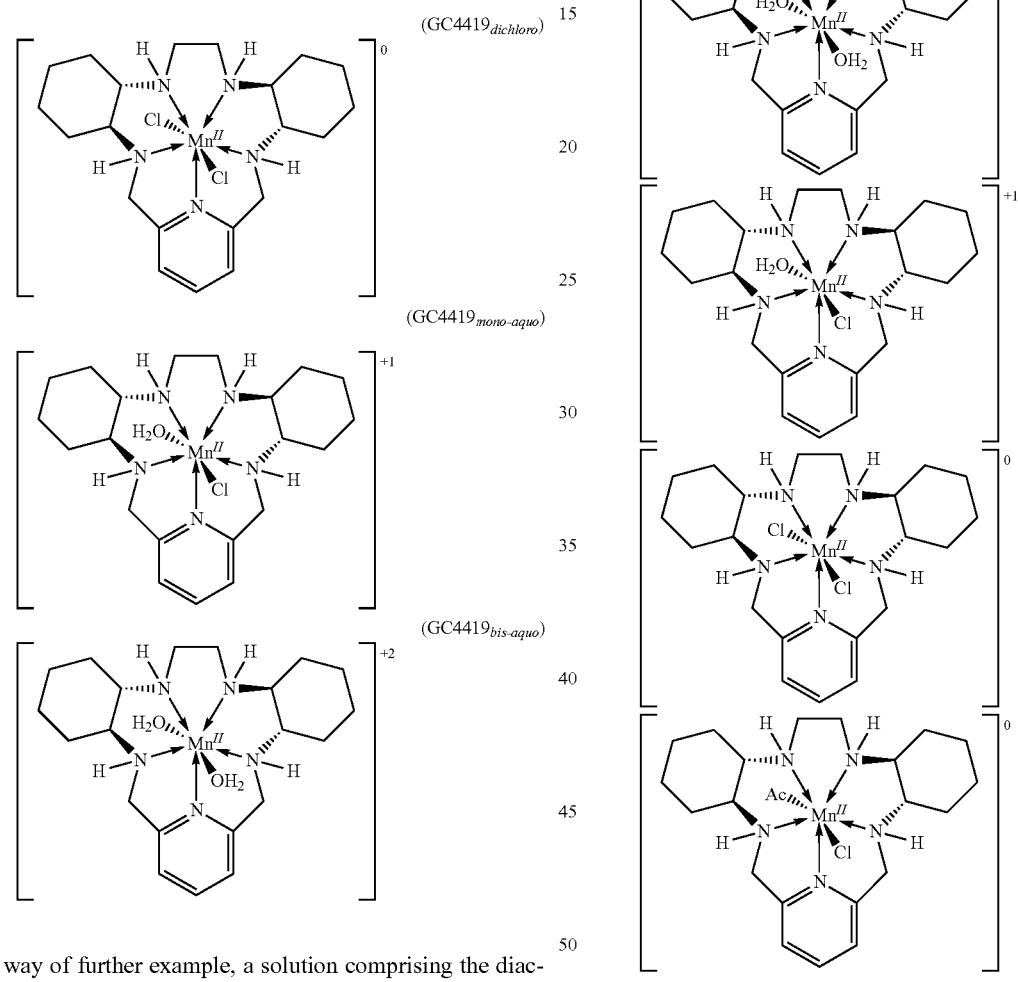

By way of further example, a solution comprising the diacetate complex form of Formula (GC4419) dissolved in buffered saline would be expected to include a mixture of at least the following complexes in equilibrium:

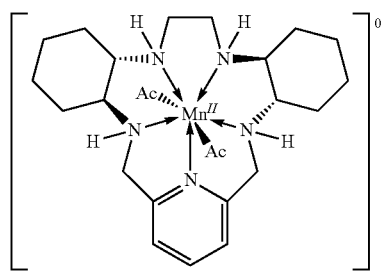

Preferably, the enantiomeric purity of the superoxide dismutase mimetic compound is greater than 95%, more preferably greater than 98%, more preferably greater than 99%, and most preferably greater than 99.5%. As used herein, the term "enantiomeric purity" refers to the amount of a compound having the depicted absolute stereochemistry, expressed as a percentage of the total amount of the depicted compound and its enantiomer. Preferably, the diastereomeric purity of the superoxide dismutase mimetic compound is greater than 98%, more preferably greater than 99%, and most preferably greater than 99.5%. As used herein, the term "diastereomeric purity" refers to the amount of a compound having the depicted absolute stereochemistry, expressed as a percentage of the total amount of the depicted compound and its diastereomers. Methods for determining diastereomeric and enantiomeric purity are well-known in the art. Diastereomeric purity can be determined by any analytical method capable of quantitatively distinguishing between a compound and its diastereomers, such as high performance liquid chromatography (HPLC). Similarly, enantiomeric purity can be determined by any analytical method capable of quantitatively distinguishing between a compound and its enantiomer. Examples of suitable analytical methods for determining enantiomeric purity include, without limitation, optical rotation of plane-polarized light using a polarimeter, and HPLC using a chiral column packing material.

The superoxide dismutase mimetics are also preferably chemically pure. Preferably, the chemical purity of the superoxide dismutase mimetic compound is greater than 95%, more preferably greater than 98%, and most preferably greater than 99%. Chemical purity can be ascertained, for example, by high pressure liquid chromatography.

High Dose/Amount of the Superoxide Dismutase Mimetic and Improved Pharmacokinetic Parameters Actual dosage levels of superoxide dismutase mimetic active ingredients in the pharmaceutical compositions and formulations described herein can be varied so as to obtain an amount of the active compound(s) that is effective to achieve the desired therapeutic response for a particular patient, compositions and mode of administration. The selected dosage level will generally depend, for instance, upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, the superoxide dismutase mimetic compound can be administered as a pharmaceutical composition or unit dose formulation containing the compound of interest, typically in combination with one or more pharmaceutically acceptable carriers. It will be understood that therapeutically effective amounts of the superoxide dismutase mimetics (or other compounds described herein) include a sufficient amount of the compound to treat diseases or conditions, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular subject will depend upon a variety of factors including the disease or disorder being treated and the severity of the diseases or disorder; activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed; and like factors well known in the medical arts. For example, it is well within the skill of the art to start doses of compounds at levels lower than required to achieve the desired therapeutic effect and to gradually increase the dosage until the desired effect is achieved.

Administration of the superoxide dismutase mimetic(s) can occur as a single event or over a time course of treatment. For example, a superoxide dismutase mimetic can be administered daily (including multiple daily doses), weekly, bi-weekly, or monthly. For treatment of acute conditions, the time course of treatment may be at least several minutes, hours, or days. Certain conditions could extend treatment from several days to several weeks. For example, treatment could extend over one week, two weeks, or three weeks, and so on. For more chronic conditions, treatment could extend from several weeks to several months, a year or more, or the lifetime of the subject in need of such treatment. Alternatively, the superoxide dismutase mimetic can be administered daily, weekly, bi-weekly, or monthly, for a period of several weeks, months, years, or over the lifetime of the mammal as a prophylactic or inhibitory measure.

As noted above, it has been surprisingly discovered that relatively high doses (including single doses and unit doses), and high rates of administration to the patient, of the superoxide dismutase mimetics described herein can be administered to subjects in need thereof, as compared, for example, to structurally similar compounds, such as its enantiomer (e.g., Formula (GC4419) vs. prior art compound (GC4403)).

In general, therefore, methods described herein involve the administration of the superoxide dismutase mimetic corresponding to Formula (GC4419), at relatively high doses and/or relatively rapid time intervals. In accordance with the treatment methods described herein for tissue damage resulting from a cancer treatment or other radiation exposure, the superoxide dismutase mimetic may also be administered within a particular time period, e.g., a 15 minute time period, a 30 minute time period, a 45 minute time period, or a 60 minute time period, or longer, in various amounts (e.g., at least 25 mg, 50 mg, 100 mg, and so on, or other amounts based upon the body weight of the patient). Thus, for example, at least 25 mg, at least 50 mg, at least 75 mg, at least 100 mg, at least 125 mg, at least 150 mg, at least 175 mg, at least 200 mg, at least 225 mg, at least 250 mg, at least 275 mg, or at least 300 mg of the superoxide dismutase mimetic corresponding to Formula (GC4419) can be administered within a 15 minute time period, a 30 minute time period, a 45 minute time period, or a 60 minute time period, or longer.

In one embodiment, for example, an amount of the superoxide dismutase mimetic corresponding to Formula (GC4419) is administered to the patient at a rate of at least 100 mg/hr. In accordance with this embodiment, for example, the amount can be administered at a rate of at least 150 mg/hr, at least 200 mg/hr, at least 250 mg/hr, at least 300 mg/hr, at least 350 mg/hr, at least 400 mg/hr, at least 450 mg/hr, at least 500 mg/hr, at least 550 mg/hr, or at least at least 600 mg/hr. Thus, for example, the amount administered may be at least 25 mg, at least 50 mg, at least 75 mg, at least 100 mg, at least 125 mg, at least 150 mg, at least 175 mg, at least 200 mg, at least 225 mg, at least 250 mg, at least 275 mg, or at least 300 mg of the superoxide dismutase mimetic corresponding to Formula (GC4419).

In one embodiment, for example, an amount of the superoxide dismutase mimetic corresponding to Formula (GC4419) is administered to the patient within a 15 minute time period. In accordance with this embodiment, for example, the amount administered may be at least 25 mg, at least 50 mg, at least 75 mg, at least 100 mg, at least 125 mg, at least 150 mg, at least 175 mg, at least 200 mg, at least 225 mg, at least 250 mg, at least 275 mg, or at least 300 mg of the superoxide dismutase mimetic corresponding to Formula (GC4419). Thus, for example, at least 25 mg can be administered to the patient within the 15 minute time period; at least 50 mg can be administered to the patient within the 15 minute time period; at least 75 mg can be administered to the patient within the 15 minute time period; at least 100 mg can be administered to the patient within the 15 minute time period; at least 125 mg can be administered to the patient within the 15 minute time period; or at least 150 mg can be administered to the patient within the 15 minute time period. In accordance with these embodiments, one preferred superoxide dismutase mimetic is the dichloro complex form of Formula (GC4419).

In another embodiment, for example, an amount of the superoxide dismutase mimetic corresponding to Formula (GC4419) is administered to the patient within a 30 minute period. In accordance with this embodiment, for example, the amount administered may be at least 50 mg, at least 75 mg, at least 100 mg, at least 125 mg, at least 150 mg, at least 175 mg, at least 200 mg, at least 225 mg, at least 250 mg, at least 275 mg, or at least 300 mg of the superoxide dismutase mimetic corresponding to Formula (GC4419). Thus, for example, at least 50 mg can be administered to the patient within the 30 minute time period; at least 75 mg can be administered to the patient within the 30 minute time period; at least 100 mg can be administered to the patient within the 30 minute time period; at least 125 mg can be administered to the patient within the 30 minute time period; at least 125 mg can be administered to the patient within the 30 minute time period; at least 150 mg can be administered to the patient within the 30 minute time period; at least 175 mg can be administered to the patient within the 30 minute time period; at least 200 mg can be administered to the patient within the 30 minute time period; at least 225 mg can be administered to the patient within the 30 minute time period; at least 250 mg can be administered to the patient within the 30 minute time period; at least 275 mg can be administered to the patient within the 30 minute time period; or at least 300 mg can be administered to the patient within the 30 minute time period. In accordance with these embodiments, one preferred superoxide dismutase mimetic is the dichloro complex form of Formula (GC4419).

In another embodiment, for example, an amount of the superoxide dismutase mimetic corresponding to Formula (GC4419) is administered to the patient within a 45 minute period. In accordance with this embodiment, for example, the amount administered may be at least 50 mg, at least 75 mg, at least 100 mg, at least 125 mg, at least 150 mg, at least 175 mg, at least 200 mg, at least 225 mg, at least 250 mg, at least 275 mg, at least 300 mg, at least 325 mg, at least 350 mg, at least 375 mg, at least 400 mg, at least 425 mg, or at least 450 mg of the superoxide dismutase mimetic corresponding to Formula (GC4419). Thus, for example, at least 50 mg can be administered to the patient within the 45 minute time period; at least 75 mg can be administered to the patient within the 45 minute time period; at least 100 mg can be administered to the patient within the 45 minute time period; at least 125 mg can be administered to the patient within the 45 minute time period; at least 125 mg can be administered to the patient within the 45 minute time period; at least 150 mg can be administered to the patient within the 45 minute time period; at least 175 mg can be administered to the patient within the 45 minute time period; at least 200 mg can be administered to the patient within the 45 minute time period; at least 225 mg can be administered to the patient within the 45 minute time period; at least 250 mg can be administered to the patient within the 45 minute time period; at least 275 mg can be administered to the patient within the 45 minute time period; at least 300 mg can be administered to the patient within the 45 minute time period; at least 325 mg can be administered to the patient within the 45 minute time period; at least 350 mg can be administered to the patient within the 45 minute time period; at least 375 mg can be administered to the patient within the 45 minute time period; at least 400 mg can be administered to the patient within the 45 minute time period; at least 425 mg can be administered to the patient within the 45 minute time period; or at least 450 mg can be administered to the patient within the 45 minute time period. In accordance with these embodiments, one preferred superoxide dismutase mimetic is the dichloro complex form of Formula (GC4419).

In another embodiment, for example, an amount of the superoxide dismutase mimetic corresponding to Formula (GC4419) is administered to the patient within a 60 minute period. In accordance with this embodiment, for example, the amount administered may be at least 50 mg, at least 75 mg, at least 100 mg, at least 125 mg, at least 150 mg, at least 175 mg, at least 200 mg, at least 225 mg, at least 250 mg, at least 275 mg, at least 300 mg, at least 325 mg, at least 350 mg, at least 375 mg, at least 400 mg, at least 425 mg, at least 450 mg, at least 475 mg, at least 500 mg, at least 525 mg, at least 550 mg, at least 575 mg; or at least 600 mg of the superoxide dismutase mimetic corresponding to Formula (GC4419). Thus, for example, at least 50 mg can be administered to the patient within the 60 minute time period; at least 75 mg can be administered to the patient within the 60 minute time period; at least 100 mg can be administered to the patient within the 60 minute time period; at least 125 mg can be administered to the patient within the 60 minute time period; at least 125 mg can be administered to the patient within the 60 minute time period; at least 150 mg can be administered to the patient within the 60 minute time period; at least 175 mg can be administered to the patient within the 60 minute time period; at least 200 mg can be administered to the patient within the 60 minute time period; at least 225 mg can be administered to the patient within the 60 minute time period; at least 250 mg can be administered to the patient within the 60 minute time period; at least 275 mg can be administered to the patient within the 60 minute time period; at least 300 mg can be administered to the patient within the 60 minute time period; at least 325 mg can be administered to the patient within the 60 minute time period; at least 350 mg can be administered to the patient within the 60 minute time period; at least 375 mg can be administered to the patient within the 60 minute time period; at least 400 mg can be administered to the patient within the 60 minute time period; at least 425 mg can be administered to the patient within the 60 minute time period; at least 450 mg can be administered to the patient within the 60 minute time period; at least 475 mg can be administered to the patient within the 60 minute time period; at least 500 mg can be administered to the patient within the 60 minute time period; at least 525 mg can be administered to the patient within the 60 minute time period; at least 550 mg can be administered to the patient within the 60 minute time period; at least 575 mg can be administered to the patient within the 60 minute time period; or at least 600 mg can be administered to the patient within the 60 minute time period. In accordance with these embodiments, one preferred superoxide dismutase mimetic is the dichloro complex form of Formula (GC4419).

In other embodiments, for example, at least 0.67 mg/kg of patient body weight; at least 1.0 mg/kg of patient body weight; at least 1.5 mg/kg of patient body weight; at least 2.0 mg/kg of patient body weight; at least 2.5 mg/kg of patient body weight; at least 3.0 mg/kg of patient body weight; at least 3.5 mg/kg of patient body weight; at least 4.0 mg/kg of patient body weight; at least 5.0 mg/kg of patient body weight; at least 6.0 mg/kg of patient body weight; at least 7.5 mg/kg of patient body weight; or at least 10.0 mg/kg of patient body weight of the superoxide dismutase mimetic corresponding to Formula (GC4419) is administered to the patient within a particular time period (e.g., a 15 minute time period, a 30 minute time period, a 45 minute time period, or a 60 minute time period). Thus, for example, at least 0.67 mg/kg of patient body weight can be administered to the patient within a 15 minute time period; at least 1.0 mg/kg of patient body weight can be administered to the patient within a 15 minute time period; at least 1.5 mg/kg of patient body weight can be administered to the patient within a 15 minute time period; at least 2.0 mg/kg of patient body weight can be administered to the patient within a 15 minute time period; at least 2.5 mg/kg of patient body weight can be administered to the patient within a 15 minute time period; at least 0.67 mg/kg of patient body weight can be administered to the patient within a 30 minute time period; at least 1.0 mg/kg of patient body weight can be administered to the patient within a 30 minute time period; at least 1.5 mg/kg of patient body weight can be administered to the patient within a 30 minute time period; at least 2.0 mg/kg of patient body weight can be administered to the patient within a 30 minute time period; at least 2.5 mg/kg of patient body weight can be administered to the patient within a 30 minute time period; at least 3.0 mg/kg of patient body weight can be administered to the patient within a 30 minute time period; at least 3.5 mg/kg of patient body weight can be administered to the patient within a 30 minute time period; at least 4.0 mg/kg of patient body weight can be administered to the patient within a 30 minute time period; at least 5.0 mg/kg of patient body weight can be administered to the patient within a 30 minute time period; at least 6.0 mg/kg of patient body weight can be administered to the patient within a 30 minute time period; at least 7.5 mg/kg of patient body weight can be administered to the patient within a 30 minute time period; at least 0.67 mg/kg of patient body weight can be administered to the patient within a 45 minute time period; at least 1.0 mg/kg of patient body weight can be administered to the patient within a 45 minute time period; at least 1.5 mg/kg of patient body weight can be administered to the patient within a 45 minute time period; at least 2.0 mg/kg of patient body weight can be administered to the patient within a 45 minute time period; at least 2.5 mg/kg of patient body weight can be administered to the patient within a 45 minute time period; at least 3.0 mg/kg of patient body weight can be administered to the patient within a 45 minute time period; at least 3.5 mg/kg of patient body weight can be administered to the patient within a 45 minute time period; at least 4.0 mg/kg of patient body weight can be administered to the patient within a 45 minute time period; at least 5.0 mg/kg of patient body weight can be administered to the patient within a 45 minute time period; at least 6.0 mg/kg of patient body weight can be administered to the patient within a 45 minute time period; at least 7.5 mg/kg of patient body weight can be administered to the patient within a 45 minute time period; at least 0.67 mg/kg of patient body weight can be administered to the patient within a 60 minute time period; at least 1.0 mg/kg of patient body weight can be administered to the patient within a 60 minute time period; at least 1.5 mg/kg of patient body weight can be administered to the patient within a 60 minute time period; at least 2.0 mg/kg of patient body weight can be administered to the patient within a 60 minute time period; at least 2.5 mg/kg of patient body weight can be administered to the patient within a 60 minute time period; at least 3.0 mg/kg of patient body weight can be administered to the patient within a 60 minute time period; at least 3.5 mg/kg of patient body weight can be administered to the patient within a 60 minute time period; at least 4.0 mg/kg of patient body weight can be administered to the patient within a 60 minute time period; at least 5.0 mg/kg of patient body weight can be administered to the patient within a 60 minute time period; at least 6.0 mg/kg of patient body weight can be administered to the patient within a 60 minute time period; at least 7.5 mg/kg of patient body weight can be administered to the patient within a 60 minute time period; or at least 10.0 mg/kg of patient body weight can be administered to the patient within a 60 minute time period. In accordance with these embodiments, one preferred superoxide dismutase mimetic is the dichloro complex form of Formula (GC4419).

In other embodiments, for example, the amount administered is at least 25 mg, at least 50 mg, at least 75 mg, at least 100 mg, at least 125 mg, at least 150 mg, at least 175 mg, at least 200 mg, at least 225 mg, at least 250 mg, at least 275 mg, at least 300 mg, at least 325 mg, at least 350 mg, at least 375 mg, at least 400 mg, at least 425 mg, at least 450 mg, at least 475 mg, at least 500 mg, at least 525 mg, at least 550 mg, at least 575 mg, or at least 600 mg of the superoxide dismutase mimetic corresponding to Formula (GC4419) (i.e., without regard to the time period for administration). In other embodiments, for example, the amount administered is at least 0.67 mg/kg of patient body weight; at least 1.0 mg/kg of patient body weight; at least 1.5 mg/kg of patient body weight; at least 2.0 mg/kg of patient body weight; at least 2.5 mg/kg of patient body weight; at least 3.0 mg/kg of patient body weight; at least 3.5 mg/kg of patient body weight; at least 4.0 mg/kg of patient body weight; at least 5.0 mg/kg of patient body weight; at least 6.0 mg/kg of patient body weight; at least 7.5 mg/kg of patient body weight; or at least 10.0 mg/kg of patient body weight; or at least 10.0 mg/kg of patient body weight (i.e., without regard to the time period for administration).

If desired, the effective dose can be divided into multiple doses for purposes of administration; consequently, single dose compositions may contain such amounts or submultiples thereof to make up the dose.

Also, some aspects of the disclosure relate to improved pharmacokinetic profiles for the superoxide dismutase mimetics described herein when administered to a subject. Due, at least in part, to the improved safety profile of the superoxide dismutase mimetics corresponding to Formula (GC4419) (e.g., the dichloro complex of Formula (GC4419)), for example, administration of these compounds result in a patient exposure as measured by AUC (i.e., the area under the curve in a graph of the concentration of a compound in blood plasma over time) that is greater than that of related superoxide dismutase mimetics (such as the mirror image compound GC4403, discussed above).

In one embodiment, for example, the methods described herein comprise administering to a patient a superoxide dismutase mimetic corresponding to Formula (GC4419) to provide an exposure as measured by an area under the curve (AUC) of at least 4,000 ng-h/mL, as calculated from the measurement of the superoxide dismutase mimetic concentration in the patient's plasma. Thus, for example, the AUC may be at least 5,000 ng-h/mL; at least 7,500 ng-h/mL; at least 10,000 ng-h/mL; at least 12,500 ng-h/mL; at least 15,000 ng-h/mL; at least 17,500 ng-h/mL; at least 20,000 ng-h/mL; at least 22,500 ng-h/mL; at least 25,000 ng-h/mL; at least 27,500 ng-h/mL; at least 30,000 ng-h/mL; at least 32,500 ng-h/mL; at least 35,000 ng-h/mL; at least 37,500 ng-h/mL; at least 40,000 ng-h/mL; at least 42,500 ng-h/mL; at least 45,000 ng-h/mL; at least 47,500 ng-h/mL; or at least 50,000 ng-h/mL; as calculated from the measurement of the superoxide dismutase mimetic concentration in the patient's plasma. In accordance with these embodiments, one preferred superoxide dismutase mimetic is the dichloro complex form of Formula (GC4419).

Methods and Indications

The superoxide dismutase mimetics described herein (e.g., those corresponding to Formula (GC4419)) can be used for treating tissue damage and/or a range of diseases and conditions modulated by superoxide. Typically, such tissue damage, diseases, and conditions can be treated by controlling superoxide levels in a subject, preferably by administering a compound corresponding to Formula (GC4419), either alone or in combination with another active agent, for example, as part of a therapeutic or prophylactic regimen. Treating diseases and conditions (including damaged tissue) as described herein may generally involve not only inhibiting the disease in a patient that is experiencing or displaying the pathology or symptomatology of the disease or condition (i.e., arresting further development of the pathology and/or symptomatology), but also ameliorating the disease or condition in a patient that is experiencing or displaying the pathology or symptomatology of the disease or condition (i.e., reversing the pathology and/or symptomatology). Treating a human patient for a disease or condition as described herein, e.g., tissue damage resulting from the administration of radiation therapy or chemotherapy, or exposure to radiation, also amounts to the inhibition or prophylaxis of such damage in a patient that is not necessarily experiencing or displaying the pathology or symptomatology of the disease or condition.

The methods of the present disclosure may advantageously be used to treat (e.g., inhibit, ameliorate, or mitigate) a variety of diseases or conditions in a variety of subjects (i.e., patients). The subject may be, for example, a mammal such as bovine, avian, canine, equine, feline, ovine, porcine, or primate (including humans and non-human primates). A subject may also include mammals of importance due to being endangered, or economic importance, such as animals raised on farms for consumption by humans, or animals of social importance to humans such as animals kept as pets or in zoos. Examples of such animals include but are not limited to: cats, dogs, swine, ruminants or ungulates such as cattle, oxen, sheep, giraffes, deer, goats, bison, camels or horses. In one embodiment, the subject is bovine, avian, canine, equine, feline, ovine, porcine, or non-human primate. In one preferred embodiment, the subject is a human patient.

Treatment of Tissue Damage

In accordance with one aspect of the present disclosure, methods are described herein for treating tissue damage resulting from a cancer treatment (e.g., radiation therapy or chemotherapy) delivered to a subject in need thereof. In accordance with another aspect of the present disclosure, methods are described herein for treating a human patient for tissue damage resulting from exposure to radiation. Thus, in various embodiments for example, the exposure to radiation in various embodiments may be an accidental radiation exposure, an unintentional radiation exposure, or an intentional radiation exposure. As noted above, treatment of tissue damage as described herein may include both inhibition (i.e., prophylaxis) and amelioration of any tissue damage that may result from an occurrence or activity. In general, the methods involve administering to the subject a therapeutically effective amount of a superoxide dismutase mimetic corresponding to Formula (GC4419). In one preferred embodiment, the superoxide dismutase mimetic is the dichloro complex form of Formula (GC4419).

Treatment of tissue damage resulting from a cancer treatment or other radiation exposure in accordance with the methods described herein involves the administration of a therapeutically effective amount of the superoxide dismutase mimetic corresponding to Formula (GC4419). In general, a range of therapeutically effective amounts may be used, depending, for example, on the compound selected and its safety and efficacy, the type, location, and severity of the tissue damage, among other factors.

In some embodiments, treatment of tissue damage in accordance with the methods described herein involves the administration of the superoxide dismutase mimetic corresponding to Formula (GC4419), at relatively high doses and/or relatively rapid time intervals. In accordance with the treatment methods described herein for tissue damage resulting from a cancer treatment or other radiation exposure, the superoxide dismutase mimetic may also be administered within a particular time period, e.g., a 15 minute time period, a 30 minute time period, or a 60 minute time period, or longer, in various amounts (e.g., at least 25 mg, 50 mg, 100 mg, and so on, or other amounts based upon the body weight of the patient). In accordance with these embodiments, one preferred superoxide dismutase mimetic is the dichloro complex form of Formula (GC4419).

In one embodiment, for example, an amount of the superoxide dismutase mimetic corresponding to Formula (GC4419) is administered to the patient within a 15 minute time period. In accordance with this embodiment, for example, the amount administered may be at least 25 mg, at least 50 mg, at least 75 mg, at least 100 mg, at least 125 mg, at least 150 mg, at least 175 mg, at least 200 mg, at least 225 mg, at least 250 mg, at least 275 mg, or at least 300 mg of the superoxide dismutase mimetic corresponding to Formula (GC4419). Thus, for example, at least 25 mg can be administered to the patient within the 15 minute time period; at least 50 mg can be administered to the patient within the 15 minute time period; at least 75 mg can be administered to the patient within the 15 minute time period; at least 100 mg can be administered to the patient within the 15 minute time period; at least 125 mg can be administered to the patient within the 15 minute time period; or at least 150 mg can be administered to the patient within the 15 minute time period. In accordance with these embodiments, one preferred superoxide dismutase mimetic is the dichloro complex form of Formula (GC4419).

In another embodiment, for example, an amount of the superoxide dismutase mimetic corresponding to Formula (GC4419) is administered to the patient within a 30 minute period. In accordance with this embodiment, for example, the amount administered may be at least 50 mg, at least 75 mg, at least 100 mg, at least 125 mg, at least 150 mg, at least 175 mg, at least 200 mg, at least 225 mg, at least 250 mg, at least 275 mg, or at least 300 mg of the superoxide dismutase mimetic corresponding to Formula (GC4419). Thus, for example, at least 50 mg can be administered to the patient within the 30 minute time period; at least 75 mg can be administered to the patient within the 30 minute time period; at least 100 mg can be administered to the patient within the 30 minute time period; at least 125 mg can be administered to the patient within the 30 minute time period; at least 125 mg can be administered to the patient within the 30 minute time period; at least 150 mg can be administered to the patient within the 30 minute time period; at least 175 mg can be administered to the patient within the 30 minute time period; at least 200 mg can be administered to the patient within the 30 minute time period; at least 225 mg can be administered to the patient within the 30 minute time period; at least 250 mg can be administered to the patient within the 30 minute time period; at least 275 mg can be administered to the patient within the 30 minute time period; or at least 300 mg can be administered to the patient within the 30 minute time period. In accordance with these embodiments, one preferred superoxide dismutase mimetic is the dichloro complex form of Formula (GC4419).

In another embodiment, for example, an amount of the superoxide dismutase mimetic corresponding to Formula (GC4419) is administered to the patient within a 45 minute period. In accordance with this embodiment, for example, the amount administered may be at least 50 mg, at least 75 mg, at least 100 mg, at least 125 mg, at least 150 mg, at least 175 mg, at least 200 mg, at least 225 mg, at least 250 mg, at least 275 mg, at least 300 mg, at least 325 mg, at least 350 mg, at least 375 mg, at least 400 mg, at least 425 mg, or at least 450 mg of the superoxide dismutase mimetic corresponding to Formula (GC4419). Thus, for example, at least 50 mg can be administered to the patient within the 45 minute time period; at least 75 mg can be administered to the patient within the 45 minute time period; at least 100 mg can be administered to the patient within the 45 minute time period; at least 125 mg can be administered to the patient within the 45 minute time period; at least 125 mg can be administered to the patient within the 45 minute time period; at least 150 mg can be administered to the patient within the 45 minute time period; at least 175 mg can be administered to the patient within the 45 minute time period; at least 200 mg can be administered to the patient within the 45 minute time period; at least 225 mg can be administered to the patient within the 45 minute time period; at least 250 mg can be administered to the patient within the 45 minute time period; at least 275 mg can be administered to the patient within the 45 minute time period; at least 300 mg can be administered to the patient within the 45 minute time period; at least 325 mg can be administered to the patient within the 45 minute time period; at least 350 mg can be administered to the patient within the 45 minute time period; at least 375 mg can be administered to the patient within the 45 minute time period; at least 400 mg can be administered to the patient within the 45 minute time period; at least 425 mg can be administered to the patient within the 45 minute time period; or at least 450 mg can be administered to the patient within the 45 minute time period. In accordance with these embodiments, one preferred superoxide dismutase mimetic is the dichloro complex form of Formula (GC4419).

In another embodiment, for example, an amount of the superoxide dismutase mimetic corresponding to Formula (GC4419) is administered to the patient within a 60 minute period. In accordance with this embodiment, for example, the amount administered may be at least 50 mg, at least 75 mg, at least 100 mg, at least 125 mg, at least 150 mg, at least 175 mg, at least 200 mg, at least 225 mg, at least 250 mg, at least 275 mg, at least 300 mg, at least 325 mg, at least 350 mg, at least 375 mg, at least 400 mg, at least 425 mg, at least 450 mg, at least 475 mg, at least 500 mg, at least 525 mg, at least 550 mg, at least 575 mg; or at least 600 mg of the superoxide dismutase mimetic corresponding to Formula (GC4419). Thus, for example, at least 50 mg can be administered to the patient within the 60 minute time period; at least 75 mg can be administered to the patient within the 60 minute time period; at least 100 mg can be administered to the patient within the 60 minute time period; at least 125 mg can be administered to the patient within the 60 minute time period; at least 125 mg can be administered to the patient within the 60 minute time period; at least 150 mg can be administered to the patient within the 60 minute time period; at least 175 mg can be administered to the patient within the 60 minute time period; at least 200 mg can be administered to the patient within the 60 minute time period; at least 225 mg can be administered to the patient within the 60 minute time period; at least 250 mg can be administered to the patient within the 60 minute time period; at least 275 mg can be administered to the patient within the 60 minute time period; at least 300 mg can be administered to the patient within the 60 minute time period; at least 325 mg can be administered to the patient within the 60 minute time period; at least 350 mg can be administered to the patient within the 60 minute time period; at least 375 mg can be administered to the patient within the 60 minute time period; at least 400 mg can be administered to the patient within the 60 minute time period; at least 425 mg can be administered to the patient within the 60 minute time period; at least 450 mg can be administered to the patient within the 60 minute time period; at least 475 mg can be administered to the patient within the 60 minute time period; at least 500 mg can be administered to the patient within the 60 minute time period; at least 525 mg can be administered to the patient within the 60 minute time period; at least 550 mg can be administered to the patient within the 60 minute time period; at least 575 mg can be administered to the patient within the 60 minute time period; or at least 600 mg can be administered to the patient within the 60 minute time period. In accordance with these embodiments, one preferred superoxide dismutase mimetic is the dichloro complex form of Formula (GC4419).

In other embodiments, for example, at least 0.67 mg/kg of patient body weight; at least 1.0 mg/kg of patient body weight; at least 1.5 mg/kg of patient body weight; at least 2.0 mg/kg of patient body weight; at least 2.5 mg/kg of patient body weight; at least 3.0 mg/kg of patient body weight; at least 3.5 mg/kg of patient body weight; at least 4.0 mg/kg of patient body weight; at least 5.0 mg/kg of patient body weight; at least 6.0 mg/kg of patient body weight; at least 7.5 mg/kg of patient body weight; or at least 10.0 mg/kg of patient body weight of the superoxide dismutase mimetic corresponding to Formula (GC4419) is administered to the patient within a particular time period (e.g., a 15 minute time period, a 30 minute time period, a 45 minute time period, or a 60 minute time period). Thus, for example, at least 0.67 mg/kg of patient body weight can be administered to the patient within a 15 minute time period; at least 1.0 mg/kg of patient body weight can be administered to the patient within a 15 minute time period; at least 1.5 mg/kg of patient body weight can be administered to the patient within a 15 minute time period; at least 2.0 mg/kg of patient body weight can be administered to the patient within a 15 minute time period; at least 2.5 mg/kg of patient body weight can be administered to the patient within a 15 minute time period; at least 0.67 mg/kg of patient body weight can be administered to the patient within a 30 minute time period; at least 1.0 mg/kg of patient body weight can be administered to the patient within a 30 minute time period; at least 1.5 mg/kg of patient body weight can be administered to the patient within a 30 minute time period; at least 2.0 mg/kg of patient body weight can be administered to the patient within a 30 minute time period; at least 2.5 mg/kg of patient body weight can be administered to the patient within a 30 minute time period; at least 3.0 mg/kg of patient body weight can be administered to the patient within a 30 minute time period; at least 3.5 mg/kg of patient body weight can be administered to the patient within a 30 minute time period; at least 4.0 mg/kg of patient body weight can be administered to the patient within a 30 minute time period; at least 5.0 mg/kg of patient body weight can be administered to the patient within a 30 minute time period; at least 6.0 mg/kg of patient body weight can be administered to the patient within a 30 minute time period; at least 7.5 mg/kg of patient body weight can be administered to the patient within a 30 minute time period; at least 0.67 mg/kg of patient body weight can be administered to the patient within a 45 minute time period; at least 1.0 mg/kg of patient body weight can be administered to the patient within a 45 minute time period; at least 1.5 mg/kg of patient body weight can be administered to the patient within a 45 minute time period; at least 2.0 mg/kg of patient body weight can be administered to the patient within a 45 minute time period; at least 2.5 mg/kg of patient body weight can be administered to the patient within a 45 minute time period; at least 3.0 mg/kg of patient body weight can be administered to the patient within a 45 minute time period; at least 3.5 mg/kg of patient body weight can be administered to the patient within a 45 minute time period; at least 4.0 mg/kg of patient body weight can be administered to the patient within a 45 minute time period; at least 5.0 mg/kg of patient body weight can be administered to the patient within a 45 minute time period; at least 6.0 mg/kg of patient body weight can be administered to the patient within a 45 minute time period; at least 7.5 mg/kg of patient body weight can be administered to the patient within a 45 minute time period; at least 0.67 mg/kg of patient body weight can be administered to the patient within a 60 minute time period; at least 1.0 mg/kg of patient body weight can be administered to the patient within a 60 minute time period; at least 1.5 mg/kg of patient body weight can be administered to the patient within a 60 minute time period; at least 2.0 mg/kg of patient body weight can be administered to the patient within a 60 minute time period; at least 2.5 mg/kg of patient body weight can be administered to the patient within a 60 minute time period; at least 3.0 mg/kg of patient body weight can be administered to the patient within a 60 minute time period; at least 3.5 mg/kg of patient body weight can be administered to the patient within a 60 minute time period; at least 4.0 mg/kg of patient body weight can be administered to the patient within a 60 minute time period; at least 5.0 mg/kg of patient body weight can be administered to the patient within a 60 minute time period; at least 6.0 mg/kg of patient body weight can be administered to the patient within a 60 minute time period; at least 7.5 mg/kg of patient body weight can be administered to the patient within a 60 minute time period; or at least 10.0 mg/kg of patient body weight can be administered to the patient within a 60 minute time period. In accordance with these embodiments, one preferred superoxide dismutase mimetic is the dichloro complex form of Formula (GC4419).

In other embodiments, for example, the amount administered is at least 25 mg, at least 50 mg, at least 75 mg, at least 100 mg, at least 125 mg, at least 150 mg, at least 175 mg, at least 200 mg, at least 225 mg, at least 250 mg, at least 275 mg, at least 300 mg, at least 325 mg, at least 350 mg, at least 375 mg, at least 400 mg, at least 425 mg, at least 450 mg, at least 475 mg, at least 500 mg, at least 525 mg, at least 550 mg, at least 575 mg, or at least 600 mg of the superoxide dismutase mimetic corresponding to Formula (GC4419) (i.e., without regard to the time period for administration). In other embodiments, for example, the amount administered is at least 0.67 mg/kg of patient body weight; at least 1.0 mg/kg of patient body weight; at least 1.5 mg/kg of patient body weight; at least 2.0 mg/kg of patient body weight; at least 2.5 mg/kg of patient body weight; at least 3.0 mg/kg of patient body weight; at least 3.5 mg/kg of patient body weight; at least 4.0 mg/kg of patient body weight; at least 5.0 mg/kg of patient body weight; at least 6.0 mg/kg of patient body weight; at least 7.5 mg/kg of patient body weight; or at least 10.0 mg/kg of patient body weight; or at least 10.0 mg/kg of patient body weight (i.e., without regard to the time period for administration).

If desired, the effective dose can be divided into multiple doses for purposes of administration; consequently, single dose compositions may contain such amounts or submultiples thereof to make up the dose.

Also, some aspects of the disclosure relate to improved pharmacokinetic profiles for the superoxide dismutase mimetics described herein when administered to a subject. Due, at least in part, to the improved safety profile of the superoxide dismutase mimetics corresponding to Formula (GC4419) (e.g., GC4419), for example, administration of these compounds result in a patient exposure as measured by AUC (i.e., the area under the curve in a graph of the concentration of a compound in blood plasma over time) that is greater than that of related superoxide dismutase mimetics (such as the mirror image compound GC4403, discussed above).

In one embodiment, for example, the methods described herein comprise administering to a patient a superoxide dismutase mimetic corresponding to Formula (GC4419) to provide an exposure as measured by an area under the curve (AUC) of at least 4,000 ng-h/mL, as calculated from the measurement of the superoxide dismutase mimetic concentration in the patient's plasma. Thus, for example, the AUC may be at least 5,000 ng-h/mL; at least 7,500 ng-h/mL; at least 10,000 ng-h/mL; at least 12,500 ng-h/mL; at least 15,000 ng-h/mL; at least 17,500 ng-h/mL; at least 20,000 ng-h/mL; at least 22,500 ng-h/mL; at least 25,000 ng-h/mL; at least 27,500 ng-h/mL; at least 30,000 ng-h/mL; at least 32,500 ng-h/mL; at least 35,000 ng-h/mL; at least 37,500 ng-h/mL; at least 40,000 ng-h/mL; at least 42,500 ng-h/mL; at least 45,000 ng-h/mL; at least 47,500 ng-h/mL; or at least 50,000 ng-h/mL; as calculated from the measurement of the superoxide dismutase mimetic concentration in the patient's plasma. In accordance with these embodiments, one preferred superoxide dismutase mimetic is the dichloro complex form of Formula (GC4419).

In general, the temporal aspects of the administration of the superoxide dismutase mimetic may depend for example, on the particular compound, radiation therapy, or chemotherapy that is selected, or the type, nature, and/or duration of the radiation exposure. Other considerations may include the disease or disorder being treated and the severity of the disease or disorder; activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed; and like factors. For example, the superoxide dismutase mimetic may be administered in various embodiments before, during, and/or after the administration of the cancer therapy (e.g., radiation therapy or chemotherapy). By way of another example, the superoxide dismutase mimetic may be administered in various embodiments before, during, and/or after an exposure to radiation.

In one embodiment, for example, the superoxide dismutase mimetic is administered to the patient prior to or simultaneous with the cancer therapy. In another embodiment, for example, the superoxide dismutase mimetic is administered to the patient prior to, but not after, the cancer therapy. In yet another embodiment, the superoxide dismutase mimetic is administered to the patient at least 15 minutes, 30 minutes, 45 minutes, 60 minutes, 90 minutes, 180 minutes, 0.5 days, 1 day, 3 days, 5 days, one week, two weeks, three weeks, four weeks, five weeks, six weeks, seven weeks, eight weeks, nine weeks, ten weeks, eleven weeks, twelve weeks, or longer, prior to the cancer therapy. In still other embodiments, for example, the superoxide dismutase mimetic is administered to the patient after the cancer therapy; thus, for example, the superoxide dismutase mimetic may be administered up to 15 minutes, 30 minutes, 45 minutes, 60 minutes, 90 minutes, or 180 minutes, 0.5 days, 1 day, 3 days, 5 days, one week, two weeks, three weeks, four weeks, five weeks, six weeks, seven weeks, eight weeks, nine weeks, ten weeks, eleven weeks, twelve weeks, or longer, after the cancer treatment. In accordance with these embodiments, one preferred superoxide dismutase mimetic is the dichloro complex form of Formula (GC4419).

In another embodiment, for example, the superoxide dismutase mimetic is administered to the patient prior to or simultaneous with the radiation exposure. In another embodiment, for example, the superoxide dismutase mimetic is administered to the patient prior to, but not after, the radiation exposure. In yet another embodiment, the superoxide dismutase mimetic is administered to the patient at least 15 minutes, 30 minutes, 45 minutes, 60 minutes, 90 minutes, 180 minutes, 0.5 days, 1 day, 3 days, 5 days, one week, two weeks, three weeks, four weeks, five weeks, six weeks, seven weeks, eight weeks, nine weeks, ten weeks, eleven weeks, twelve weeks, or longer, prior to the radiation exposure. In still other embodiments, for example, the superoxide dismutase mimetic is administered to the patient after the radiation exposure; thus, for example, the superoxide dismutase mimetic may be administered up to 15 minutes, 30 minutes, 45 minutes, 60 minutes, 90 minutes, or 180 minutes, 0.5 days, 1 day, 3 days, 5 days, one week, two weeks, three weeks, four weeks, five weeks, six weeks, seven weeks, eight weeks, nine weeks, ten weeks, eleven weeks, twelve weeks, or longer, after the radiation exposure. In accordance with these embodiments, one preferred superoxide dismutase mimetic is the dichloro complex form of Formula (GC4419).

In one embodiment, for example, the cancer treatment comprises the administration of radiation therapy; for example, an intentional exposure to radiation. In accordance with this embodiment, the method provides a safe and effective method of treating radiation damage and inhibiting or ameliorating radiation-related cancers or radiation-related tissue damage in a patient in need thereof by administering to the patient a therapeutically effective amount of a superoxide dismutase mimetic corresponding to Formula (GC4419).

In another embodiment, the exposure to radiation is an accidental or unintentional exposure. For example, the radiation exposure may result from a wide variety of commercial and non-commercial activities including, but not limited to activities in industries such as utility and power, oil/gas petrochemical, chemical/plastics, automatic ventilation control (cooking, smoking, etc.), heavy industrial manufacturing, environmental toxicology and remediation, biomedicine, cosmetic/perfume, pharmaceutical, transportation, emergency response and law enforcement, military or terrorist activities, and detection (e.g., hazardous leaks or spills). In one embodiment, for example, the exposure to radiation may result from the excavation and/or clean-up of radioactive material from air, groundwater, surface water, sediment and/or soil.

In various embodiments, the source of radiation may be electromagnetic, including visible or ultraviolet light, or nuclear, including alpha, beta, gamma, or cosmic radiation. The types of damage may include, but is not limited to, various forms of dermatological or mucosal damage, such as mucositis, esophagitis, and the like, as well as internal cell loss, fibrosis, cyst formation, neuropathies and various types of benign and malignant tumors.

Additionally, or alternatively, in another embodiment the cancer treatment comprises administration of a chemotherapeutic agent. In accordance with this embodiment, the method provides a safe and effective method of treating, ameliorating, or inhibiting toxicity to normal tissues from chemotherapy in a patient in need thereof, or receiving inadvertent or intentional administration of chemical agents having a free radical toxicological component, by administering to the patient a therapeutically effective amount of a superoxide dismutase mimetic corresponding to Formula (GC4419). The methods described herein are useful for reducing the toxicity of chemical agents having a free radical component including fluoropyrimidines, pyrimidine nucleosides, purines, platinum analogues, anthracyclines, podophyllotoxins, camptothecins, hormones and hormone analogues, enzymes, proteins and antibodies, vinca alkaloids, taxanes, and the like, among other agents. While the present methods for reducing toxicity are applicable for any chemotherapeutic agent, representative examples include irinotecan, FU, paclitael, docetaxel, cisplatin, doxorubicin, oxaliplatin, cyclophasphamide, EGF and VGF inhibitors, acemannan, acetaminophen, aclarubicin, aldesleukin, alemtuzumab, alitretinoin, altretamine, amifostine, aminolevulinic acid, amrubicin, amsacrine, anagrelide, anastrozole, ANGER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, tretinoin, edelfosine, edrecolomab, eflornithine, emitefiur, epirubicin, epoetin beta, etoposide phosphate, exemestane, exisulind, fadrozole, filgrastim, finasteride, fludarabine phosphate, formestane, fotemustine, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, IL-2, imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofuran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200

(Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), SU 6668 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Treatment of Diseases and Conditions in accordance with another aspect of the present disclosure, methods are described herein for treating a range of diseases and conditions modulated by superoxide in a subject in need thereof. As noted above, treatment of diseases and conditions as described herein may include both inhibition (i.e., prophylaxis) and amelioration of such disease or condition. In general, the methods involve administering to the subject a therapeutically effective amount of a superoxide dismutase mimetic corresponding to Formula (GC4419). In one preferred embodiment, the superoxide dismutase mimetic is the dichloro complex of Formula (GC4419).

Treatment of diseases and conditions in accordance with the methods described herein involves the administration of the superoxide dismutase mimetic corresponding to Formula (GC4419), at relatively high doses and/or relatively rapid time intervals. In accordance with the treatment methods described herein for tissue damage resulting from a cancer treatment or other radiation exposure, the superoxide dismutase mimetic may also be administered within a particular time period, e.g., a 15 minute time period, a 30 minute time period, a 45 minute time period, or a 60 minute time period, or longer, in various amounts (e.g., at least 25 mg, 50 mg, 100 mg, and so on, or other amounts based upon the body weight of the patient).

In one embodiment, for example, an amount of the superoxide dismutase mimetic corresponding to Formula (GC4419) is administered to the patient within a 15 minute time period. In accordance with this embodiment, for example, the amount administered may be at least 25 mg, at least 50 mg, at least 75 mg, at least 100 mg, at least 125 mg, at least 150 mg, at least 175 mg, at least 200 mg, at least 225 mg, at least 250 mg, at least 275 mg, or at least 300 mg of the superoxide dismutase mimetic corresponding to Formula (GC4419). Thus, for example, at least 25 mg can be administered to the patient within the 15 minute time period; at least 50 mg can be administered to the patient within the 15 minute time period; at least 75 mg can be administered to the patient within the 15 minute time period; at least 100 mg can be administered to the patient within the 15 minute time period; at least 125 mg can be administered to the patient within the 15 minute time period; or at least 150 mg can be administered to the patient within the 15 minute time period. In accordance with these embodiments, one preferred superoxide dismutase mimetic is the dichloro complex form of Formula (GC4419).

In another embodiment, for example, an amount of the superoxide dismutase mimetic corresponding to Formula (GC4419) is administered to the patient within a 30 minute period. In accordance with this embodiment, for example, the amount administered may be at least 50 mg, at least 75 mg, at least 100 mg, at least 125 mg, at least 150 mg, at least 175 mg, at least 200 mg, at least 225 mg, at least 250 mg, at least 275 mg, or at least 300 mg of the superoxide dismutase mimetic corresponding to Formula (GC4419). Thus, for example, at least 50 mg can be administered to the patient within the 30 minute time period; at least 75 mg can be administered to the patient within the 30 minute time period; at least 100 mg can be administered to the patient within the 30 minute time period; at least 125 mg can be administered to the patient within the 30 minute time period; at least 125 mg can be administered to the patient within the 30 minute time period; at least 150 mg can be administered to the patient within the 30 minute time period; at least 175 mg can be administered to the patient within the 30 minute time period; at least 200 mg can be administered to the patient within the 30 minute time period; at least 225 mg can be administered to the patient within the 30 minute time period; at least 250 mg can be administered to the patient within the 30 minute time period; at least 275 mg can be administered to the patient within the 30 minute time period; or at least 300 mg can be administered to the patient within the 30 minute time period. In accordance with these embodiments, one preferred superoxide dismutase mimetic is the dichloro complex form of Formula (GC4419).

In another embodiment, for example, an amount of the superoxide dismutase mimetic corresponding to Formula (GC4419) is administered to the patient within a 45 minute period. In accordance with this embodiment, for example, the amount administered may be at least 50 mg, at least 75 mg, at least 100 mg, at least 125 mg, at least 150 mg, at least 175 mg, at least 200 mg, at least 225 mg, at least 250 mg, at least 275 mg, at least 300 mg, at least 325 mg, at least 350 mg, at least 375 mg, at least 400 mg, at least 425 mg, or at least 450 mg of the superoxide dismutase mimetic corresponding to Formula (GC4419). Thus, for example, at least 50 mg can be administered to the patient within the 45 minute time period; at least 75 mg can be administered to the patient within the 45 minute time period; at least 100 mg can be administered to the patient within the 45 minute time period; at least 125 mg can be administered to the patient within the 45 minute time period; at least 125 mg can be administered to the patient within the 45 minute time period; at least 150 mg can be administered to the patient within the 45 minute time period; at least 175 mg can be administered to the patient within the 45 minute time period; at least 200 mg can be administered to the patient within the 45 minute time period; at least 225 mg can be administered to the patient within the 45 minute time period; at least 250 mg can be administered to the patient within the 45 minute time period; at least 275 mg can be administered to the patient within the 45 minute time period; at least 300 mg can be administered to the patient within the 45 minute time period; at least 325 mg can be administered to the patient within the 45 minute time period; at least 350 mg can be administered to the patient within the 45 minute time period; at least 375 mg can be administered to the patient within the 45 minute time period; at least 400 mg can be administered to the patient within the 45 minute time period; at least 425 mg can be administered to the patient within the 45 minute time period; or at least 450 mg can be administered to the patient within the 45 minute time period. In accordance with these embodiments, one preferred superoxide dismutase mimetic is the dichloro complex form of Formula (GC4419).

In another embodiment, for example, an amount of the superoxide dismutase mimetic corresponding to Formula (GC4419) is administered to the patient within a 60 minute period. In accordance with this embodiment, for example, the amount administered may be at least 50 mg, at least 75 mg, at least 100 mg, at least 125 mg, at least 150 mg, at least 175 mg, at least 200 mg, at least 225 mg, at least 250 mg, at least 275 mg, at least 300 mg, at least 325 mg, at least 350 mg, at least 375 mg, at least 400 mg, at least 425 mg, at least 450 mg, at least 475 mg, at least 500 mg, at least 525 mg, at least 550 mg, at least 575 mg; or at least 600 mg of the superoxide dismutase mimetic corresponding to Formula (GC4419). Thus, for example, at least 50 mg can be administered to the patient within the 60 minute time period; at least 75 mg can be administered to the patient within the 60 minute time period; at least 100 mg can be administered to the patient within the 60 minute time period; at least 125 mg can be administered to the patient within the 60 minute time period; at least 125 mg can be administered to the patient within the 60 minute time period; at least 150 mg can be administered to the patient within the 60 minute time period; at least 175 mg can be administered to the patient within the 60 minute time period; at least 200 mg can be administered to the patient within the 60 minute time period; at least 225 mg can be administered to the patient within the 60 minute time period; at least 250 mg can be administered to the patient within the 60 minute time period; at least 275 mg can be administered to the patient within the 60 minute time period; at least 300 mg can be administered to the patient within the 60 minute time period; at least 325 mg can be administered to the patient within the 60 minute time period; at least 350 mg can be administered to the patient within the 60 minute time period; at least 375 mg can be administered to the patient within the 60 minute time period; at least 400 mg can be administered to the patient within the 60 minute time period; at least 425 mg can be administered to the patient within the 60 minute time period; at least 450 mg can be administered to the patient within the 60 minute time period; at least 475 mg can be administered to the patient within the 60 minute time period; at least 500 mg can be administered to the patient within the 60 minute time period; at least 525 mg can be administered to the patient within the 60 minute time period; at least 550 mg can be administered to the patient within the 60 minute time period; at least 575 mg can be administered to the patient within the 60 minute time period; or at least 600 mg can be administered to the patient within the 60 minute time period. In accordance with these embodiments, one preferred superoxide dismutase mimetic is the dichloro complex form of Formula (GC4419).

In other embodiments, for example, at least 0.67 mg/kg of patient body weight; at least 1.0 mg/kg of patient body weight; at least 1.5 mg/kg of patient body weight; at least 2.0 mg/kg of patient body weight; at least 2.5 mg/kg of patient body weight; at least 3.0 mg/kg of patient body weight; at least 3.5 mg/kg of patient body weight; at least 4.0 mg/kg of patient body weight; at least 5.0 mg/kg of patient body weight; at least 6.0 mg/kg of patient body weight; at least 7.5 mg/kg of patient body weight; or at least 10.0 mg/kg of patient body weight of the superoxide dismutase mimetic corresponding to Formula (GC4419) is administered to the patient within a particular time period (e.g., a 15 minute time period, a 30 minute time period, a 45 minute time period, or a 60 minute time period). Thus, for example, at least 0.67 mg/kg of patient body weight can be administered to the patient within a 15 minute time period; at least 1.0 mg/kg of patient body weight can be administered to the patient within a 15 minute time period; at least 1.5 mg/kg of patient body weight can be administered to the patient within a 15 minute time period; at least 2.0 mg/kg of patient body weight can be administered to the patient within a 15 minute time period; at least 2.5 mg/kg of patient body weight can be administered to the patient within a 15 minute time period; at least 0.67 mg/kg of patient body weight can be administered to the patient within a 30 minute time period; at least 1.0 mg/kg of patient body weight can be administered to the patient within a 30 minute time period; at least 1.5 mg/kg of patient body weight can be administered to the patient within a 30 minute time period; at least 2.0 mg/kg of patient body weight can be administered to the patient within a 30 minute time period; at least 2.5 mg/kg of patient body weight can be administered to the patient within a 30 minute time period; at least 3.0 mg/kg of patient body weight can be administered to the patient within a 30 minute time period; at least 3.5 mg/kg of patient body weight can be administered to the patient within a 30 minute time period; at least 4.0 mg/kg of patient body weight can be administered to the patient within a 30 minute time period; at least 5.0 mg/kg of patient body weight can be administered to the patient within a 30 minute time period; at least 6.0 mg/kg of patient body weight can be administered to the patient within a 30 minute time period; at least 7.5 mg/kg of patient body weight can be administered to the patient within a 30 minute time period; at least 0.67 mg/kg of patient body weight can be administered to the patient within a 45 minute time period; at least 1.0 mg/kg of patient body weight can be administered to the patient within a 45 minute time period; at least 1.5 mg/kg of patient body weight can be administered to the patient within a 45 minute time period; at least 2.0 mg/kg of patient body weight can be administered to the patient within a 45 minute time period; at least 2.5 mg/kg of patient body weight can be administered to the patient within a 45 minute time period; at least 3.0 mg/kg of patient body weight can be administered to the patient within a 45 minute time period; at least 3.5 mg/kg of patient body weight can be administered to the patient within a 45 minute time period; at least 4.0 mg/kg of patient body weight can be administered to the patient within a 45 minute time period; at least 5.0 mg/kg of patient body weight can be administered to the patient within a 45 minute time period; at least 6.0 mg/kg of patient body weight can be administered to the patient within a 45 minute time period; at least 7.5 mg/kg of patient body weight can be administered to the patient within a 45 minute time period; at least 0.67 mg/kg of patient body weight can be administered to the patient within a 60 minute time period; at least 1.0 mg/kg of patient body weight can be administered to the patient within a 60 minute time period; at least 1.5 mg/kg of patient body weight can be administered to the patient within a 60 minute time period; at least 2.0 mg/kg of patient body weight can be administered to the patient within a 60 minute time period; at least 2.5 mg/kg of patient body weight can be administered to the patient within a 60 minute time period; at least 3.0 mg/kg of patient body weight can be administered to the patient within a 60 minute time period; at least 3.5 mg/kg of patient body weight can be administered to the patient within a 60 minute time period; at least 4.0 mg/kg of patient body weight can be administered to the patient within a 60 minute time period; at least 5.0 mg/kg of patient body weight can be administered to the patient within a 60 minute time period; at least 6.0 mg/kg of patient body weight can be administered to the patient within a 60 minute time period; at least 7.5 mg/kg of patient body weight can be administered to the patient within a 60 minute time period; or at least 10.0 mg/kg of patient body weight can be administered to the patient within a 60 minute time period. In accordance with these embodiments, one preferred superoxide dismutase mimetic is the dichloro complex form of Formula (GC4419).

In other embodiments, for example, the amount administered is at least 25 mg, at least 50 mg, at least 75 mg, at least 100 mg, at least 125 mg, at least 150 mg, at least 175 mg, at least 200 mg, at least 225 mg, at least 250 mg, at least 275 mg, at least 300 mg, at least 325 mg, at least 350 mg, at least 375 mg, at least 400 mg, at least 425 mg, at least 450 mg, at least 475 mg, at least 500 mg, at least 525 mg, at least 550 mg, at least 575 mg, or at least 600 mg of the superoxide dismutase mimetic corresponding to Formula (GC4419) (i.e., without regard to the time period for administration). In other embodiments, for example, the amount administered is at least 0.67 mg/kg of patient body weight; at least 1.0 mg/kg of patient body weight; at least 1.5 mg/kg of patient body weight; at least 2.0 mg/kg of patient body weight; at least 2.5 mg/kg of patient body weight; at least 3.0 mg/kg of patient body weight; at least 3.5 mg/kg of patient body weight; at least 4.0 mg/kg of patient body weight; at least 5.0 mg/kg of patient body weight; at least 6.0 mg/kg of patient body weight; at least 7.5 mg/kg of patient body weight; or at least 10.0 mg/kg of patient body weight; or at least 10.0 mg/kg of patient body weight (i.e., without regard to the time period for administration).

If desired, the effective dose can be divided into multiple doses for purposes of administration; consequently, single dose compositions may contain such amounts or submultiples thereof to make up the dose.

Also, some aspects of the disclosure relate to improved pharmacokinetic profiles for the superoxide dismutase mimetics described herein when administered to a subject. Due, at least in part, to the improved safety profile of the superoxide dismutase mimetics corresponding to Formula (GC4419) (e.g., the dichloro complex of Formula (GC4419)), for example, administration of these compounds result in a patient exposure as measured by AUC (i.e., the area under the curve in a graph of the concentration of a compound in blood plasma over time) that is greater than that of related superoxide dismutase mimetics (such as the mirror image compound GC4403, discussed above).

In one embodiment, for example, the methods described herein comprise administering to a patient a superoxide dismutase mimetic corresponding to Formula (GC4419) to provide an exposure as measured by an area under the curve (AUC) of at least 4,000 ng-h/mL, as calculated from the measurement of the superoxide dismutase mimetic concentration in the patient's plasma. Thus, for example, the AUC may be at least 5,000 ng-h/mL; at least 7,500 ng-h/mL; at least 10,000 ng-h/mL; at least 12,500 ng-h/mL; at least 15,000 ng-h/mL; at least 17,500 ng-h/mL; at least 20,000 ng-h/mL; at least 22,500 ng-h/mL; at least 25,000 ng-h/mL; at least 27,500 ng-h/mL; at least 30,000 ng-h/mL; at least 32,500 ng-h/mL; at least 35,000 ng-h/mL; at least 37,500 ng-h/mL; at least 40,000 ng-h/mL; at least 42,500 ng-h/mL; at least 45,000 ng-h/mL; at least 47,500 ng-h/mL; or at least 50,000 ng-h/mL; as calculated from the measurement of the superoxide dismutase mimetic concentration in the patient's plasma. In accordance with these embodiments, one preferred superoxide dismutase mimetic is the dichloro complex form of Formula (GC4419).

In general, the temporal aspects of the administration of the superoxide dismutase mimetic may depend for example, on the particular compound, or the disease or condition being treated. Other considerations may include the severity of the disease or condition; activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed; and like factors.

As noted above, the diseases or conditions treated in accordance with the methods described herein may be any disease or condition that is/are modulated by superoxide. In one embodiment, for example, the disease or condition is selected from cancer, a cardiovascular disorder, a cerebrovascular disorder, a dermatological disorder, a fibrotic disorder, a gastrointestinal disorder, an immunological disorder, an inflammatory disorder, a metabolic disorder, a neurological disorder, an ophthalmic disorder, a pulmonary disorder, an infectious disease, and combinations thereof. By way of example, uses include the treatment of inflammatory and hyperproliferative skin diseases and cutaneous manifestations of immunologically-mediated illnesses, such as psoriasis, atopic dermatitis, contact dermatitis and further eczematous dermatitises, seborrhoeis dermatitis, lichen planus, pemphigus, bullous pemphigoid, epidermolysis bullosa, urticaria, angioedemas, vasculitides, erythemas, cutaneous eosinophilias, lupus erythematosus, acne and alopecia greata; various eye diseases (autoimmune and otherwise) such as keratoconjunctivitis, vernal conjunctivitis, uveitis associated with Behcet's disease, keratitis, herpetic keratitis, conical cornea, dystrophia epithelialis corneae, corneal leukoma, and ocular pemphigus. In addition, reversible obstructive airway disease, which includes conditions such as asthma (for example, bronchial asthma, allergic asthma, intrinsic asthma, extrinsic asthma and dust asthma), particularly chronic or inveterate asthma (for example, late asthma and airway hyper-responsiveness), bronchitis, allergic rhinitis, and the like, can be treated, prevented, and/or ameliorated in accordance with the methods described herein. Other treatable diseases and conditions include inflammation of mucosa and blood vessels such as gastric ulcers, vascular damage caused by ischemic diseases and thrombosis. Moreover, hyperproliferative vascular diseases such as intimal smooth muscle cell hyperplasia, restenosis and vascular occlusion, particularly following biologically- or mechanically-mediated vascular injury, could be treated by the compounds described herein.

Still other treatable diseases and conditions include, but are not limited to, cardiac diseases such as post myocardial infarction, pulmonary diseases such as pulmonary muscle changes or remodeling and chronic obstructive pulmonary disease (COPD); ischemic bowel diseases, inflammatory bowel diseases, necrotizing enterocolitis, intestinal inflammations/allergies such as Coeliac diseases, proctitis, eosinophilic gastroenteritis, mastocytosis, Crohn's disease and ulcerative colitis; nervous diseases such as multiple myositis, Guillain-Barre syndrome, Meniere's disease, polyneuritis, multiple neuritis, mononeuritis and radiculopathy; septic shock and related refractory hypotension; endocrine diseases such as hyperthyroidism and Basedow's disease; arthritis (for example rheumatoid arthritis, arthritis chronica progrediente and arthritis deformans) and rheumatic diseases; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergic sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Sjogren's syndrome; adiposis; eosinophilic fasciitis; periodontal disease such as lesions of gingiva, periodontium, alveolar bone and substantia ossea dentis; nephrotic syndrome such as glomerulonephritis; male pattern aleopecia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury such as ischemia-reperfusion injury of organs (such as heart, liver, kidney and digestive tract) which occurs upon preservation, transplantation, organ failure (single or multi-), or ischemic disease (for example, thrombosis and cardiac infarction); dyskinetic disorders such as Parkinson's disease, neuroleptic-induced parkinsonism and tardive dyskinesias; intestinal diseases such as endotoxin-shock, pseudomembranous colitis and colitis caused by drug or radiation; renal diseases such as ischemic acute renal insufficiency and chronic renal insufficiency; pulmonary diseases such as toxinosis caused by lung-oxygen or drug (for example, paracort and bleomycins), lung cancer and pulmonary emphysema; ocular diseases such as cataracta, siderosis, retinitis, pigmentosa, senile macular degeneration, vitreal scarring and corneal alkali burn; dermatitis such as erythema multiforme, linear IgA ballous dermatitis and cement dermatitis; and others such as gingivitis, periodontitis, sepsis, pancreatitis, diseases caused by environmental pollution (for example, air pollution), aging, carcinogenesis, metastasis of carcinoma and hypobaropathy; diseases caused by histamine or leukotriene-C4 release; Behcet's disease such as intestinal-, vasculo- or neuro-Behcet's disease, and also Behcet's which affects the oral cavity, skin, eye, vulva, articulation, epididymis, lung, kidney and so on. Furthermore, the compounds of the invention are useful for the treatment and prevention of hepatic disease such as immunogenic diseases (for example, chronic autoimmune liver diseases such as autoimmune hepatitis, primary biliary cirrhosis and sclerosing cholangitis), partial liver resection, acute liver necrosis (e.g., necrosis caused by toxin, viral hepatitis, shock or anoxia), B-virus hepatitis, non-A/non-B hepatitis, cirrhosis (such as alcoholic cirrhosis) and hepatic failure such as fulminant hepatic failure, late-onset hepatic failure and "acute-on-chronic" liver failure (acute liver failure on chronic liver diseases), and for treatment of bacterial or viral infections such as influenza or HIV infection, and moreover are useful for various diseases because of their useful activity such as augmentation of chemotherapeutic effect, cytomegalovirus infection, particularly HCMV infection, anti-inflammatory activity, sclerosing and fibrotic diseases such as nephrosis, scleroderma, fibrosis (e.g., pulmonary fibrosis and lung fibrosis, including cryptogenic fibrosing alveolitis, idiopathic interstitial pneumonias, ideopathic pulmonary fibrosis, ideopathic mediastinal fibrosis, fibrosis complicating anti-neoplastic therapy, radiation therapy, and chronic infection, including tuberculosis and aspergillosis and other fungal infections), arteriosclerosis, congestive heart failure, ventricular hypertrophy, post-surgical adhesions and scarring, stroke, myocardial infarction and injury associated with ischemia and reperfusion, and the like.

Routes of Administration

The superoxide dismutase mimetics described herein (or pharmaceutical compositions including the superoxide dismutase mimetics) can be administered to subjects (e.g., humans and other mammals) in accordance with a number of suitable routes of administration including, but are not limited to, oral, parenteral (e.g., intravenous, intraorbital, subcutaneous, intramuscular, intraorbital, intracapsular, intraspinal, intraperitoneal, or intrasternal), topical (nasal, transdermal, buccal, ophthalmic), intravesical, intrathecal, enteral, pulmonary, intralymphatic, intracavital, vaginal, rectal, transurethral, intradermal, intraocular, aural, intramammary, orthotopic, intratracheal, intralesional, percutaneous, endoscopical, transmucosal, sublingual and intestinal administration. In one embodiment, the superoxide dismutase mimetic is introduced to the patient via oral administration, or by injection, including by intravenous, subcutaneous, intramuscular, intraperitoneal, intra-arterial, and intradermal injection. Additionally or alternatively, the superoxide dismutase mimetics described herein (or pharmaceutical compositions including the superoxide dismutase mimetics) described herein can be administered to subjects topically (as by patches (e.g., transdermal patches), powders, lotions, ointments or drops applied to the skin), buccally, or inhaled, as an oral or nasal spray. The superoxide dismutase mimetics described herein (or pharmaceutical compositions including the superoxide dismutase mimetics) can also be administered to humans and other mammals intrarectally or intravaginally. In one embodiment, the superoxide dismutase mimetic (or a pharmaceutical composition or unit dose formulation including the superoxide dismutase mimetic) is administered to the subject parenterally. It will generally be understood that parental administration refers to modes of administration which include intravenous, intramuscular, intraperitoneal, subcutaneous and intraarticular. In one preferred embodiment, the superoxide dismutase mimetic (or a pharmaceutical composition or unit dose formulation including the superoxide dismutase mimetic) is administered intravenously.

Unit Dose Formulations and Pharmaceutical Compositions

Another aspect of the present disclosure relates to the unit dose formulations and pharmaceutical compositions comprising the compounds described herein, typically together with a pharmaceutically acceptable carrier or excipient, and optionally in combination with another pharmaceutically active compound or compounds. The pharmaceutical compositions include the superoxide dismutase mimetic corresponding to Formula (GC4419), typically formulated as a pharmaceutical dosage form, optionally in combination with a pharmaceutically acceptable carrier, additive or excipient. In one embodiment, for example, the pharmaceutical composition comprises the compound of Formula (GC4419) and a pharmaceutically acceptable carrier or excipient. Unit dose formulations and pharmaceutical compositions according to the present disclosure may be used, for example, in the treatment of various cancers, cardiovascular disorders, cerebrovascular disorders, dermatological disorders, fibrotic disorders, gastrointestinal disorders, immunological disorders, inflammatory disorders, metabolic disorders, neurological disorders, ophthalmic disorders, pulmonary disorders, infectious diseases, tissue damage, and combinations thereof. Particular diseases and conditions include cancers, fibrosis, inflammatory diseases and conditions (including, for example, inflammatory bowel disease, rheumatoid arthritis, asthma, COPD, pancreatitis, and the like), dermatitis, psoriasis, and the like, as well as for protecting tissue against damage resulting from a cancer treatment or other exposure to radiation.

One particular aspect of the present disclosure is directed to a unit dose formulation comprising the superoxide dismutase mimetic in a container as described herein. In one embodiment, the superoxide dismutase mimetic corresponds to Formula (GC4419). In one preferred embodiment, the superoxide dismutase mimetic is the dichloro complex form of Formula (GC4419).

Preferably, the unit dose formulations in accordance with the present disclosure include at least 50 mg of the superoxide dismutase mimetic corresponding to Formula (GC4419). In various embodiments, for example, the unit dose formulation includes at least 50 mg, at least 75 mg, at least 100 mg, at least 125 mg, at least 150 mg, at least 175 mg, at least 200 mg, at least 225 mg, at least 250 mg, at least 275 mg, at least 300 mg, at least 325 mg, at least 350 mg, at least 375 mg, at least 400 mg, at least 425 mg, at least 450 mg, at least 475 mg, at least 500 mg, at least 525 mg, at least 550 mg, at least 575 mg, or at least 600 mg of the superoxide dismutase mimetic corresponding to Formula (GC4419). In certain of these embodiments, the superoxide dismutase mimetic is the dichloro complex form of Formula (GC4419).

Another particular aspect of the present disclosure is directed to a pharmaceutical composition in solution form, the composition being in unit dose form for intravenous administration. In accordance with this aspect, for example, the pharmaceutical composition may comprise the superoxide dismutase mimetic and a pharmaceutically acceptable carrier, contained in an IV bag or bottle for administration to a patient. Typical unit dosage IV bags are conventional glass or plastic containers having inlet and outlet means and having standard (e.g., 50 mL, 100 mL and 150 mL) capacities. Typically, a concentrated solution of reconstituted lyophilized superoxide dismutase mimetic (described in further detail below), is added to an IV (intravenous) container containing a suitable aqueous carrier. Useful carriers are described herein (e.g., sterile water, sterile saline, etc.). In general, the pharmaceutical composition may comprise from about 0.25 mg/mL to about 3.5 mg/mL of the superoxide dismutase mimetic described herein (e.g., the superoxide dismutase mimetic corresponding to Formula (GC4419). Alternatively, higher or lower concentrations of superoxide dismutase mimetic may be present depending on the intended use, packaging and shipping considerations, use of a single or multiple IV bags, etc. In one embodiment, a concentrated solution of lyophilized superoxide dismutase mimetic added to the an IV bag in an amount to form a pharmaceutical composition in solution form comprising about 0.25 mg/mL, about 0.5 mg/mL, about 0.75 mg/mL, about 1.0 mg/mL, about 1.25 mg/mL, about 1.5 mg/mL, about 1.75 mg/mL, about 2.0 mg/mL, about 2.25 mg/mL, about 2.5 mg/mL, about 2.75 mg/mL, about 3.0 mg/mL, about 3.25 mg/mL, or about 3.5 mg/mL of the superoxide dismutase mimetic.

The above-described superoxide dismutase mimetics may be dispersed in a pharmaceutically acceptable carrier prior to administration to the mammal. The carrier, also known in the art as an excipient, vehicle, auxiliary, adjuvant, or diluent, is typically a substance which is pharmaceutically inert, confers a suitable consistency or form to the composition, and does not diminish the efficacy of the compound. The carrier is generally considered to be "pharmaceutically or pharmacologically acceptable" if it does not produce an unacceptably adverse, allergic or other untoward reaction when administered to a mammal, especially a human.

The selection of a pharmaceutically acceptable carrier will also, in part, be a function of the route of administration. In general, the compositions of the described herein can be formulated for any route of administration so long as the blood circulation system is available via that route, and in accordance with the conventional route of administration of the component (e.g., the superoxide dismutase mimetic compound). For example, suitable routes of administration include, but are not limited to, oral, parenteral (e.g., intravenous, intraarterial, subcutaneous, intramuscular, intraorbital, intracapsular, intraspinal, intraperitoneal, or intrasternal), topical (nasal, transdermal, buccal, ophthalmic), intravesical, intrathecal, enteral, pulmonary, intralymphatic, intracavital, vaginal, rectal, transurethral, intradermal, intraocular, aural, intramammary, orthotopic, intratracheal, intralesional, percutaneous, endoscopical, transmucosal, sublingual and intestinal administration.

Pharmaceutically acceptable carriers for use in combination with the compounds and compositions of the present disclosure are well known to those of ordinary skill in the art and are selected based upon a number of factors: the particular compound(s) and agent(s) used, and its/their concentration, stability and intended bioavailability; safety; the subject, its age, size and general condition; and the route of administration. Suitable nonaqueous, pharmaceutically-acceptable polar solvents include, but are not limited to, water, alcohols having 2 to 30 carbon atoms; fatty acid esters of alcohols; amides; esters; ketones; sulfoxides; aliphatic, cycloaliphatic or aromatic hydrocarbons having 4 to 30 carbon atoms; and oils of mineral, vegetable, animal, essential or synthetic origin.

In one embodiment, the pharmaceutically acceptable carrier is in the form of a solution. For example, the solution may comprise water. By way of another example, the solution may comprise saline. Suitable carriers used in formulating liquid dosage forms for parenteral administration, for example, include nonaqueous, pharmaceutically-acceptable polar solvents such as oils, alcohols, amides, esters, ethers, ketones, hydrocarbons and mixtures thereof, as well as water, saline solutions (e.g., U.S.P. and isotonic sodium chloride solutions), dextrose solutions (e.g., D5W), electrolyte solutions, or any other aqueous, pharmaceutically acceptable liquid. In certain preferred embodiments, the pharmaceutical composition is in the form of an aqueous solution comprising the superoxide dismutase mimetic corresponding to Formula (GC4419) and saline (e.g., normal saline, that is, a sterile solution of 0.9% w/v of NaCl in water). In these and other embodiments, for example, the saline is preferably a physiologically buffered saline solution (i.e., buffered saline). The buffering agent may provide suitable buffering capacity around pH 7-8.5, or around pH 7.8, or within the range of pH 7.3-8. The buffering agent is preferably chemically inert and physiologically and pharmaceutically acceptable. Exemplary buffers include phosphate-based buffers, carbonate-based buffers, tris-based buffers, amino acid-based buffers (e.g., arginine, lysine, and other natural amino acids), and citrate-based buffers. Carbonate buffers (such as sodium or calcium carbonate or bicarbonate buffers) may be particularly useful in some embodiments due to their ready supply, strong buffering capacity, and compatibility. One particularly preferred buffering agent is sodium bicarbonate. In one preferred embodiment, for example, the pharmaceutically acceptable carrier comprises a buffered saline solution; more preferably in this embodiment, the buffered saline solution is a bicarbonate-buffered saline solution. In one particularly preferred embodiment, the solution is formulated with 10 mg/mL of GC4419 in an aqueous solution containing 0.9% NaCl (wt.) which contains 26 mM sodium bicarbonate with a solution pH in the range of 7.6-8.3. In one preferred embodiment, the superoxide dismutase mimetic is the dichloro complex of Formula (GC4419). As noted above, it will be understood that in solution the chloro (or other) ligands of the superoxide dismutase mimetic may dissociate with the axial coordination sites being occupied by the solvent water molecules forming both mono-aquo (monocationic) and bis-aquo (dicationic) complexes. That is, the ligands can be exchanged off and occupied by other molecules present in solution, such as solvent water molecules.

The pharmaceutical formulations are also preferably sterile. The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use. The compositions can be provided, prepared, stored, or transported in any container suitable for maintaining sterility. The container can incorporate means for dispensing an aqueous composition such as, for example, a pierceable or removable seal. The compositions can be dispensed, for example, by extraction with a syringe or by pouring the composition directly into a device (e.g., a syringe, intravenous (IV) bag, or machine) for administration to a patient. Other means for providing, preparing, storing, transporting, and dispensing sterile pharmaceutical compositions are known to those skilled in the art.

In another embodiment, the superoxide dismutase mimetic may be used or, more typically, stored, as a lyophilized powder. Those skilled in the art will appreciate that lyophilization is a freeze-drying process in which water is sublimed from the composition after it is frozen. The particular advantage associated with the lyophilization process is that, biologicals and pharmaceuticals can be dried without elevated temperatures (thereby eliminating potentially adverse thermal effects), and then stored in a dry state where there are relatively few (or at least fewer) stability problems. Methods for providing lyophilized powders or particulates are known to those of skill in the art. Bulking or caking agents are useful in lyophilized formulations to, for example, enhance product elegance and to prevent blowout. Bulking agents provide structural strength to the lyophilized cake and include, for example, sucrose, trehalose, dextran, lactose, cyclodextrin, chitosan, mannitol, and glycine. In one embodiment, the bulking agent is dextran. Buffers may also be included in the pre-lyophilized solution, as desired, to affect the relationship between the compound and the solvent (e.g., water or saline) in the solution. Suitable buffers are described elsewhere herein and include, for example, phosphate-based buffers, carbonate-based buffers, tris-based buffers, amino acid-based buffers (e.g., arginine, lysine, and other natural amino acids), and citrate-based buffers. Thus, by way of example, lyophilized forms as described herein may include the superoxide dismutase mimetic, bulking agent, and buffer, or may include only the superoxide dismutase mimetic and the bulking agent. In one particular example, the lyophilized form comprises the superoxide dismutase mimetic and dextran. In another particular example, the lyophilized form comprises the superoxide dismutase mimetic, dextran, and arginine (as a buffer). In another particular example, the lyophilized form comprises the superoxide dismutase mimetic, dextran, and lysine (as a buffer). In another particular example, the lyophilized form comprises the superoxide dismutase mimetic, dextran, and TRIS (tris(hydroxymethyl)-aminomethane)) (as a buffer).

Where a lyophilized form of the superoxide dismutase mimetics described herein are employed (e.g., for storage or shipping), these lyophilized forms must typically be reconstituted prior to administration to the patient. The lyophilized cakes may be reconstituted with any pharmaceutically acceptable carrier solution described herein, such as, for example, water or saline. If a buffer was included in the pre-lyophilized solution, it may not be necessary to include a buffer in the reconstitution solution. Where a buffer was not included in the pre-lyophilized solution, on the other hand, the reconstitution solution preferably includes a buffer for the reasons discussed above.

In some embodiments, oils or non-aqueous solvents may be employed in the formulations, e.g., to bring one or more of the compounds into solution, due to, for example, the presence of large lipophilic moieties. Alternatively, emulsions, suspensions, or other preparations, for example, liposomal preparations, may be used. With respect to liposomal preparations, for example, any known methods for preparing liposomes may be used. See, for example, Bangham et al., J. Mol. Biol, 23: 238-252 (1965) and Szoka et al., Proc. Natl. Acad. Sci. 75: 4194-4198 (1978), incorporated herein by reference. Thus, in one embodiment, one or more of the compounds are administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines. Ligands may also be attached to the liposomes, for instance, to direct these compositions to particular sites of action.

Other pharmaceutically acceptable solvents for use in the pharmaceutical compositions described herein are well known to those of ordinary skill in the art, and are identified in The Chemotherapy Source Book (Williams & Wilkens Publishing), The Handbook of Pharmaceutical Excipients, (American Pharmaceutical Association, Washington, D.C., and The Pharmaceutical Society of Great Britain, London, England, 1968), Modern Pharmaceutics, (G. Banker et al., eds., 3d ed.) (Marcel Dekker, Inc., New York, N.Y., 1995), The Pharmacological Basis of Therapeutics, (Goodman & Gilman, McGraw Hill Publishing), Pharmaceutical Dosage Forms, (H. Lieberman et al., eds.) (Marcel Dekker, Inc., New York, N.Y., 1980), Remington's Pharmaceutical Sciences (A. Gennaro, ed., 19th ed.) (Mack Publishing, Easton, Pa., 1995), The United States Pharmacopeia 24, The National Formulary 19, (National Publishing, Philadelphia, Pa., 2000), and A. J. Spiegel et al., Use of Nonaqueous Solvents in Parenteral Products, Journal of Pharmaceutical Sciences, Vol. 52, No. 10, pp. 917-927 (1963).

Formulations containing the superoxide dismutase mimetic may take the form of solid, semi-solid, lyophilized powder, or liquid dosage forms such as, for instance, aerosols, capsules, creams, emulsions, foams, gels/jellies, lotions, ointments, pastes, powders, soaps, solutions, sprays, suppositories, suspensions, sustained-release formulations, tablets, tinctures, transdermal patches, and the like, preferably in unit dosage forms suitable for simple administration of precise dosages. If formulated as a fixed dose, such pharmaceutical compositions or formulation products preferably employ the superoxide dismutase mimetics within the dosage ranges discussed above.

In general, particular formulations for superoxide dismutase mimetics are also known in the art and are generally described, for example, in U.S. Pat. Nos. 5,610,293, 5,637, 578, 5,874,421, 5,976,498, 6,084,093, 6,180,620, 6,204,259, 6,214,817, 6,245,758, 6,395,725, and 6,525,041 (each of which is hereby incorporated herein by reference in its entirety).

In certain embodiments, the pharmaceutical composition administered to the subject in accordance with the methods described herein consists essentially of the superoxide dismutase mimetic corresponding to Formula (GC4419) and a pharmaceutically acceptable carrier. In other embodiments, the pharmaceutical composition comprises the superoxide dismutase mimetic, a pharmaceutically acceptable carrier, and one or more additional pharmaceutically active agents or compounds. In these embodiments, the pharmaceutical compositions described herein are products that result from the mixing or combining of more than one active ingredient and include both fixed and non-fixed combinations of the active ingredients. Fixed combinations are those in which the active ingredients, e.g., a superoxide dismutase mimetic and another pharmaceutically active agent or compound described herein, are both administered to a patient simultaneously in the form of a single entity or dosage. Non-fixed combinations are those in which the active ingredients, e.g., a superoxide dismutase mimetic and another pharmaceutically active agent or compound, are administered to a subject as separate entities either simultaneously, concurrently or sequentially with no specific intervening time limits, wherein such administration provides effective levels of the two compounds in the body of the patient. The latter also applies to cocktail therapy, e.g., the administration of three or more active ingredients.

It is contemplated that co-formulations of the superoxide dismutase mimetic and one or more additional pharmaceutically active agents or compounds may employ conventional formulation techniques for these components individually, or alternative formulation routes, subject to compatibility and efficacy of the various components, in combination.

Additional Pharmaceutically Active Agents

As noted above, the above-described methods and pharmaceutical compositions including the superoxide dismutase mimetic may additionally include the administration of one or more pharmaceutically active agents or components. While the superoxide dismutase mimetics described herein can be administered as the sole active pharmaceutical agent, they can also be used in combination with one or more compounds of the invention or other agents. When administered as a combination, the therapeutic agents can be formulated as separate compositions that are administered at the same time or sequentially at different times (e.g., one or several hours or days later), or the therapeutic agents can be given as a single composition. Thus, the disclosure is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Suitable pharmaceutically active agents or compounds that may be included in the methods and compositions of the present disclosure include, for instance, analgesics, anti-arthritics, anti-asthmatics, anti-emetics, anesthetics (e.g., local anesthetics), anti-glaucoma agents, anti-malarials, anti-hypertensives, anti-anxiety agents, anti-clotting agents, anti-convulsants, blood glucose-lowering agents, decongestants, anti-histamines, anti-tussives, anti-pyretics, anti-cholinergics, anti-ulcer agents, anti-neoplastics, beta blockers, beta-2 agonists, beta agonists, anti-inflammatory agents, anti-psychotic agents, cognitive enhancers, cholesterol-reducing agents, anti-obesity agents, autoimmune disorder agents, anti-impotence agents, anti-bacterial and anti-fungal agents, anti-migraine agents, anti-microbials, amoebicidals or trichomonocidal agents, hypnotic agents, anti-Parkinsonism agents, anti-Alzheimer's Disease agents, antibiotics, anti-parasitics, anti-depressants, anti-viral agents, bronchodilators, agents with effect on the central nervous system, cardiovascular agents, contraceptives, cytostatics, diuretics, germicidals, H-2 blockers, hormonal agents, hypnotic agents, inotropics, muscle relaxants, muscle contractants, physic energizers, sedatives, sympathomimetics, vasodilators, vasoconstrictors, tranquilizers, electrolyte supplements, vitamins, counterirritants, stimulants, anti-hormones, drug antagonists, lipid-regulating agents, uricosurics, cardiac glycosides, expectorants, purgatives, contrast materials, radiopharmaceuticals, imaging agents, peptides, enzymes, growth factors, and the like. As noted above, the individual components of such combinations may be administered either sequentially or simultaneously in separate or combined pharmaceutical formulations.

Specific examples of antihypertensives include prazosin, nifedipine, amlodipine besylate, trimazosin and doxazosin; specific examples of a blood glucose-lowering agent are glipizide and chlorpropamide; a specific example of an anti-impotence agent is sildenafil and sildenafil citrate; specific examples of antineoplastics include chlorambucil, lomustine and echinomycin; a specific example of an imidazole-type antineoplastic is tubulazole; a specific example of an anti-hypercholesterolemic is atorvastatin and atorvastatin calcium; specific examples of anxiolytics include hydroxyzine hydrochloride and doxepin hydrochloride; specific examples of anti-inflammatory agents include betamethasone, prednisolone, aspirin, piroxicam, valdecoxib, carprofen, celecoxib, flurbiprofen and (+)-N-{4-[3-(4-fluorophenoxy)phenoxy]-2-cyclopenten-1-yl}-N-hyroxyurea; a specific example of a barbiturate is phenobarbital; specific examples of antivirals include acyclovir, nelfinavir, and virazole; specific examples of vitamins/nutritional agents include retinol and vitamin E; specific examples of beta blockers include timolol and nadolol; a specific example of an emetic is apomorphine; specific examples of a diuretic include chlorthalidone and spironolactone; a specific example of an anticoagulant is dicumarol; specific examples of cardiotonics include digoxin and digitoxin; specific examples of androgens include 17-methyltestosterone and testosterone; a specific example of a mineral corticoid is desoxycorticosterone; a specific example of a steroidal hypnotic/anesthetic is alfaxalone; specific examples of anabolic agents include fluoxymesterone and methanstenolone; specific examples of antidepression agents include sulpiride, [3,6-dimethyl-2-(2,4,6-trimethyl-phenoxy)-pyridin-4-yl]-(1-ethylpropyl)-a-mine, 3,5-dimethyl-4-(3'-pentoxy)-2-(2',4',6'-trimethylphenoxy) pyridine, pyroxidine, fluoxetine, paroxetine, venlafaxine and sertraline; specific examples of antibiotics include carbenicillin indanylsodium, bacampicillin hydrochloride, troleandomycin, doxycyline hyclate, ampicillin, amoxicillin and penicillin G; specific examples of anti-infectives include benzalkonium chloride and chlorhexidine; specific examples of coronary vasodilators include nitroglycerin and mioflazine; a specific example of a hypnotic is etomidate; specific examples of carbonic anhydrase inhibitors include acetazolamide and chlorzolamide; specific examples of antifungals include econazole, terconazole, fluconazole, voriconazole, and griseofulvin; a specific example of an antiprotozoal is metronidazole; specific examples of anthelmintic agents include thiabendazole and oxfendazole and morantel; specific examples of antihistamines include astemizole, levocabastine, cetirizine, decarboethoxyloratadine and cinnarizine; specific examples of antipsychotics include ziprasidone, olanzepine, thiothixene hydrochloride, fluspirilene, risperidone and penfluridole; specific examples of gastrointestinal agents include loperamide and cisapride; specific examples of serotonin antagonists include ketanserin and mianserin; a specific example of an anesthetic is lidocaine; a specific example of a hypoglycemic agent is acetohexamide; a specific example of an anti-emetic is dimenhydrinate; a specific example of an antibacterial is cotrimoxazole; a specific example of a dopaminergic agent is L-DOPA; specific examples of anti-Alzheimer's Disease agents are THA and donepezil; a specific example of an anti-ulcer agent/H2 antagonist is famotidine; specific examples of sedative/hypnotic agents include chlordiazepoxide and triazolam; a specific example of a vasodilator is alprostadil; a specific example of a platelet inhibitor is prostacyclin; specific examples of ACE inhibitor/antihypertensive agents include enalaprilic acid, quinapril, and lisinopril; specific examples of tetracycline antibiotics include oxytetracycline and minocycline; specific examples of macrolide antibiotics include erythromycin, clarithromycin, and spiramycin; a specific example of an azalide antibiotic is azithromycin; specific examples of glycogen phosphorylase inhibitors include [R—

(R'S')]-5-chloro-N-[2-hydroxy-3-{methoxymethylamino}3-oxo-1-(phenylme-thyl)propyl-1H-indole-2-carboxamide and 5-chloro-1H-indole-2-carboxylic acid [(1S)-benzyl-(2R)-hydroxy-3-((3R,4S)-dihydroxy-pyrrolidin-1-yl-)-3-oxypropyl]amide; and specific examples of cholesterol ester transfer protein inhibitors include [2R,4S]-4-[acetyl-(3,5-bis-trifluoromethyl-benzyl)-amino]-2-ethyl-6-trifl-uoromethyl-3,4-dihydro-2H-quinoline-1-carboxylic acid isopropyl ester, [2R,4S]-4-[3,5-bis-trifluoromethyl-benzyl)-methoxycarbonyl-amino]-2-ethyl-6-trifluoromethyl-3,4-dihydro-2H-quinoline-1-carboxylic acid ethyl ester, and [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester.

Other specific examples include, for example, anti-inflammatory drugs such as, e.g., ibuprofen, indometacin, naproxen, nalophine, and the like; anti-Parkinsonism agents such as, e.g., bromocriptine, piperidin, benzhexyl, benztropine, and the like; anti-depressants such as, e.g., imipramine, nortriptyline, pritiptyline, and the like; anti-biotics such as, e.g., clindamycin, erythomycin, fusidic acid, gentamicin, mupirocine, amfomycin, neomycin, metronidazol, sulphamethizole, bacitracin, framycetin, polymyxin B, acitromycin, and the like; anti-fungal agents such as, e.g., miconazol, ketoconaxole, clotrimazole, amphotericin B, nystatin, mepyramin, econazol, fluconazol, flucytocine, griseofulvin, bifonazole, amorofine, mycostatin, itrconazole, terbenafine, terconazole, tolnaftate, and the like; anti-microbial agents such as, e.g., metronidazole, tetracyclines, oxytetracylines, penicillins, and the like; anti-emetics such as, e.g., metoclopramide, droperidol, haloperidol, promethazine, and the like; anti-histamines such as, e.g., chlorpheniramine, terfenadine, triprolidine, and the like; anti-migraine agents such as, e.g., dihydroergotamine, ergotamine, pizofylline, and the like; coronary, cerebral or peripheral vasodilators such as, e.g., nifedipine, diltiazem, and the like; anti-anginals such as, e.g., glyceryl nitrate, isosorbide dinitrate, molsidomine, verapamil, and the like; calcium channel blockers such as, e.g., verapamil, nifedipine, diltiazem, nicardipine, and the like; hormonal agents such as, e.g., estradiol, estron, estriol, polyestradiol, polyestriol, dienestrol, diethylstilbestrol, progesterone, dihydroprogesterone, cyprosterone, danazol, testosterone, and the like; contraceptive agents such as, e.g., ethinyl estradiol, lynestrenol, etynodiol, norethisterone, mestranol, norgestrel, levonorgestrel, desodestrel, medroxyprogesterone, and the like; anti-thrombotic agents such as, e.g., heparin, warfarin, and the like; diuretics such as, e.g., hydrochlorothiazide, flunarizine, minoxidil, and the like; anti-hypertensive agents such as, e.g., propanolol, metoprolol, clonidine, pindolol, and the like; corticosteroids such as, e.g., beclomethasone, betamethasone, betamethasone-17-valerate, betamethasone-dipropionate, clobetasol, clobetasol-17-butyrate, clobetasol-propionate, desonide, desoxymethasone, dexamethasone, diflucortolone, flumethasone, flumethasone-pivalte, fluocinolone acetonide, fluocinoide, hydrocortisone, hydrocortisone-17-butyrate, hydrocortisonebuteprate, methylprednisolone, triamcinolone acetonide, hacinonide, fluprednide acetate, alklometasone-dipropionate, fluocortolone, fluticason-propionte, mometasone-furate, desoxymethasone, diflurason-diacetate, halquinol, cliochinol, chlorchinaldol, fluocinolone-acetonide, and the like; dermatological agents such as, e.g., nitrofurantoin, dithranol, clioquinol, hydroxyquinoline, isotretionin, methoxsalen, methotrexate, tretionin, trioxalen, salicylic acid, penicillamine, and the like; steroids such as, e.g., estradiol, progesterone, norethindrone, levonorgestrel, ethynodiol, levonorgestrol, norgestimate, gestanin, desogestrel, 3-keton-desogesterel, demegestone, promethoestrol, testosterone, spironolactone, esters thereof, and the like; nitro compounds such as, e.g., amyl nitrates, nitroglycerine, isosorbide nitrate, and the like; opioids such as, e.g., morphine, buprenorphine, oxymorphone, hydromorphone, codeine, tramadol, and the like; prostaglandins such as, e.g., a member of the PGA, PGB, PGE or PGF series such as, e.g. minoprostol, dinoproston, carboprost, eneprostil, and the like; and peptides such as, e.g., growth hormone releasing factors, growth factors (e.g. epidermal growth factor (EGF), nerve growth factor (NGF), TGF, PDGF, insulin growth factor (IGF), fibroblast growth factor (aFGF, bFGF etc.), somatostatin, calcitonin, insulin, vasopressin, interferons, IL-2 etc., urokinase, serratiopeptidase, superoxide dismutase, thyrotropin releasing hormone, lutenizing hormone releasing hormone (LH-RH), corticotrophin releasing hormone; growth hormone releasing hormone (GHRH), oxytodin, erythropoietin (EPO), colony stimulating factor (CSF), and the like.

Further Forms of Compounds

With respect to the compounds described herein, for example, the superoxide dismutase mimetics corresponding to Formula (GC4419) and any other pharmaceutically active agent or compound that may be included in the pharmaceutical composition, such compounds may exist in a variety of different forms, each of which and others are contemplated in the instant disclosure.

Diasteromeric mixtures can be separated into their individual diastereomers on the basis of their physical chemical differences by methods known, for example, by chromatography and/or fractional crystallization. In one embodiment, enantiomers can be separated by chiral chromatographic columns. In other embodiments, enantiomers can be separated by converting the enantiomeric mixture into a diastereomeric mixture by reaction with an appropriate optically active compound (e.g., a salt), separating the diastereomers and converting (e.g., hydrolyzing) the individual diastereomers to the corresponding pure enantiomers. As noted above, all such isomers, including diastereomers, enantiomers, and mixtures thereof, are considered as part of the compounds and compositions described herein.

It will also be understood that the methods and formulations described herein may also include the use of crystalline forms (also known as polymorphs), or pharmaceutically acceptable salts of compounds described herein, as well as active metabolites of these compounds having the same or similar type of activity. In addition, the compounds described herein can exist in unsolvated as well as solvated forms with pharmaceutically acceptable solvents such as water, ethanol, and the like. The solvated forms of the compounds presented herein are also considered to be disclosed herein.

Compounds described herein also include isotopically-labeled compounds, which are identical to those recited in the various compounds, structures, and formulae herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as $^2$H, $^3$H, $^{13}$C, $^{14}$C, $^{15}$N, and $^{54}$Mn, respectively. Certain isotopically-labeled compounds described herein, for example those into which radioactive isotopes such as $^3$H and $^{14}$C are incorporated, may be useful in drug and/or substrate tissue distribution assays. Further, substitution with isotopes such as deuterium, i.e., $^2$H, can afford certain therapeutic advantages resulting from greater metabolic stability, for example increased in vivo half-life or reduced dosage requirements.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

Compounds described herein may also be in various forms, including but not limited to, amorphous forms, milled forms and nano-particulate forms.

Kits/Articles of Manufacture

For use in the therapeutic applications described herein, kits and articles of manufacture are also described. Such kits can include a carrier, package, or container that is compartmentalized to receive one or more containers such as vials, tubes, and the like, each of the container(s) including one of the separate elements to be used in a method described herein (such as, for example, the superoxide dismutase mimetics, pharmaceutically acceptable carrier, or additional pharmaceutically active agent or compound, whether alone or in combination). Suitable containers include, for example, bottles, vials, syringes, and test tubes. The containers can be formed from a variety of materials such as glass or plastic.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252 (each of which is hereby incorporated by reference herein). Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. As noted above, a wide array of formulations of the compounds and compositions provided herein are contemplated, as are a variety of treatments for any disease, disorder, or condition that would benefit by treatment with the superoxide dismutase mimetics described herein.

Thus, for example, the container(s) can include one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits may, in one embodiment, comprise a compound (e.g., a superoxide dismutase mimetic) with an identifying description or label or instructions relating to its use in the methods described herein. The kit may further include a pharmaceutically acceptable carrier or diluent for combining with the active compound. In one embodiment, for example, the kit includes a sterile solution comprising a superoxide dismutase mimetic corresponding to Formula (GC4419). In another embodiment, for example, the kit includes a superoxide dismutase mimetic corresponding to Formula (GC4419) in the form of a lyophilized powder. In these and other embodiments, the kit may further include a solution (e.g., a sterile saline solution) for diluting the superoxide dismutase mimetic, for example in an infusion bag (which itself may be optionally included in the kit).

A kit will typically include one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carriers, packages, containers, vials, bags, and/or tube labels listing contents and/or instructions for use; and package inserts with instructions for use. A set of instructions will typically be included in various embodiments, which may be a separate sheet or brochure, or may be printed on one or more of the packages, containers, or vials (directly or on a label (such as described below)).

A label can be on or associated with the kit or one or more containers included with the kit. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions or instructions for use of the contents, such as in accordance with the methods described herein.

In certain embodiments, the pharmaceutical compositions can be presented in a pack or dispenser device which can contain one or more unit dosage forms containing one or more of the compounds and agents provided herein. The pack can, for example, contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration (FDA) or the European Medicines Agency (EMEA) for prescription drugs, or the approved product insert.

Compositions containing one or more compounds provided herein (e.g., the superoxide dismutase mimetic or other, additional pharmaceutically active agent or compound) formulated in a compatible pharmaceutical carrier can also be prepared, placed in an appropriate container, and labeled for treatment of an indicated condition.

In accordance with one aspect, the article of manufacture comprises packaging material and contained within said packaging material is a parenteral formulation for treating a disease or condition or for protecting tissue against damage resulting from exposure to a cancer treatment in a patient in need thereof, as described herein. In accordance with this embodiment, the parenteral formulation comprises a unit dose formulation as described herein, and the packaging material comprises a label or package insert with instructions for parenterally administering the dose to the patient. For example, the parenteral formulation may be in solution form and contained in a suitable vial or container.

In general, the parenteral solution may comprise from about 5 mg/mL to about 20 mg/mL of the superoxide dismutase mimetic described herein in unit dose form in a suitable container. Alternatively, higher or lower concentrations of superoxide dismutase mimetic may be present depending on the intended use, packaging and shipping considerations, use of a single or multiple vials, etc. In one embodiment, the parenteral formulation is a solution comprising about 20 mg/mL, about 17.5 mg/mL, about 15 mg/mL, about 12.5 mg/mL, about 10 mg/mL, about 7.5 mg/mL, or about 5 mg/mL of the superoxide dismutase mimetic in a single container. In another embodiment, the parenteral formulation is a solution comprising about 20 mg/mL, about 17.5 mg/mL, about 15 mg/mL, about 12.5 mg/mL, about 10 mg/mL, about 7.5 mg/mL, or about 5 mg/mL of the superoxide dismutase mimetic in multiple containers (e.g., 2 or more, 3 or more, 4 or more, etc.).

The following enumerated embodiments are presented to illustrate certain aspects of the present invention, and are not intended to limit its scope:

1. A unit dose formulation comprising at least 50 mg of a superoxide dismutase mimetic in a container, the superoxide dismutase mimetic corresponding to Formula (GC4419):

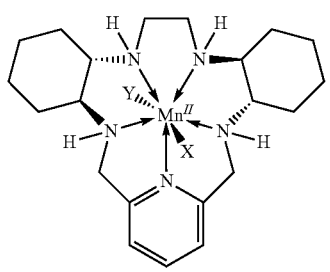

(GC4419)

wherein X and Y are independently neutral or negatively-charged ligands.

2. The unit dose formulation of embodiment 1, which comprises at least 75 mg of the superoxide dismutase mimetic.

3. The unit dose formulation of embodiment 1, which comprises at least 100 mg of the superoxide dismutase mimetic.

4. The unit dose formulation of embodiment 1, which comprises at least 125 mg of the superoxide dismutase mimetic.

5. The unit dose formulation of embodiment 1, which comprises at least 150 mg of the superoxide dismutase mimetic.

6. The unit dose formulation of embodiment 1, which comprises at least 175 mg of the superoxide dismutase mimetic.

7. The unit dose formulation of embodiment 1, which comprises at least 200 mg of the superoxide dismutase mimetic.

8. The unit dose formulation of embodiment 1, which comprises at least 225 mg of the superoxide dismutase mimetic.

9. The unit dose formulation of embodiment 1, which comprises at least 250 mg of the superoxide dismutase mimetic.

10. The unit dose formulation of embodiment 1, which comprises at least 275 mg of the superoxide dismutase mimetic.

11. The unit dose formulation of embodiment 1, which comprises at least 300 mg of the superoxide dismutase mimetic.

12. The unit dose formulation of embodiment 1, which comprises at least 325 mg of the superoxide dismutase mimetic.

13. The unit dose formulation of embodiment 1, which comprises at least 350 mg of the superoxide dismutase mimetic.

14. The unit dose formulation of embodiment 1, which comprises at least 375 mg of the superoxide dismutase mimetic.

15. The unit dose formulation of embodiment 1, which comprises at least 400 mg of the superoxide dismutase mimetic.

16. The unit dose formulation of embodiment 1, which comprises at least 425 mg of the superoxide dismutase mimetic.

17. The unit dose formulation of embodiment 1, which comprises at least 450 mg of the superoxide dismutase mimetic.

18. The unit dose formulation of embodiment 1, which comprises at least 475 mg of the superoxide dismutase mimetic.

19. The unit dose formulation of embodiment 1, which comprises at least 500 mg of the superoxide dismutase mimetic.

20. The unit dose formulation of embodiment 1, which comprises at least 525 mg of the superoxide dismutase mimetic.

21. The unit dose formulation of embodiment 1, which comprises at least 550 mg of the superoxide dismutase mimetic.

22. The unit dose formulation of embodiment 1, which comprises at least 575 mg of the superoxide dismutase mimetic.

23. The unit dose formulation of embodiment 1, which comprises at least 600 mg of the superoxide dismutase mimetic.

24. The unit dose formulation of any of embodiments 1-23, wherein the superoxide dismutase mimetic is in the form of a lyophilized powder.

25. The unit dose formulation of any of embodiments 1-24, wherein the container further includes a pharmaceutically acceptable carrier.

26. The unit dose formulation of embodiment 25, wherein the pharmaceutically acceptable carrier is in the form of a solution 27. The unit dose formulation embodiment 25, wherein the pharmaceutically acceptable carrier is a solution comprising water.

28. The unit dose formulation of embodiment 25, wherein the pharmaceutically acceptable carrier is a solution comprising saline.

29. The unit dose formulation of any of embodiments 25-28, wherein the pharmaceutically acceptable carrier comprises a buffered saline solution.

30. The unit dose formulation of any of embodiments 25-28, wherein the pharmaceutically acceptable carrier comprises a bicarbonate-buffered saline solution.

31. The unit dose formulation of any of embodiments 1-30, wherein X and Y are independently selected from monodentate ligands.

32. The unit dose formulation of any of embodiments 1-31, wherein X and Y are independently selected from the group consisting of aquo ligands, halo ligands, carboxylato ligands, and bicarbonato ligands.

33. The unit dose formulation of any of embodiments 1-32, wherein X and Y are independently selected from aquo ligands and halo ligands.

34. The unit dose formulation of any of embodiments 1-33, wherein X and Y are independently halo ligands.

35. The unit dose formulation of any of embodiments 1-34, wherein X and Y are chloro ligands.

36. The unit dose formulation of any of embodiments 1-35, wherein the superoxide dismutase mimetic corresponds to the dichloro complex form of Formula (GC4419):

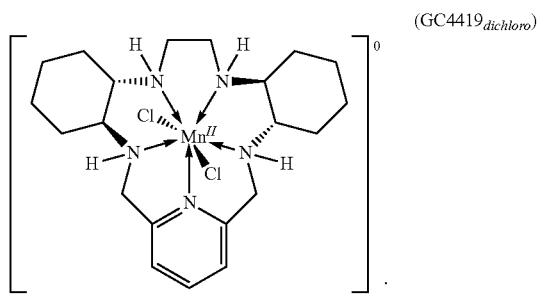

(GC4419$_{dichloro}$)

37. The unit dose formulation of any of embodiments 1-36, wherein the formulation is stored in a container for storage or for administration to a patient.

38. The unit dose formulation of embodiment 1-37, wherein the container is a vial, a syringe, or an IV bag or bottle.

39. A method for treating a human patient for tissue damage resulting from the administration of radiation therapy or chemotherapy to the patient, the method comprising administering to the patient a therapeutically effective amount of a superoxide dismutase mimetic corresponding to Formula (GC4419):

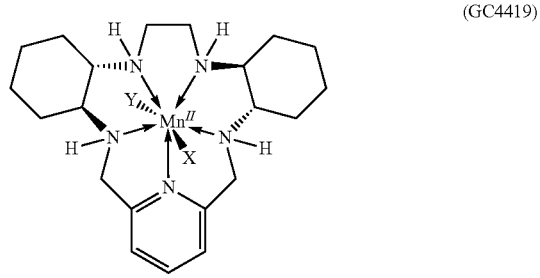

(GC4419)

wherein X and Y are independently neutral or negatively-charged ligands.

40. The method of embodiment 39, wherein the therapeutically effective amount is at least 0.67 mg/kg of patient body weight.

41. The method of embodiment 39, wherein the therapeutically effective amount is at least 1.0 mg/kg of patient body weight.

42. The method of embodiment 39, wherein the therapeutically effective amount is at least 1.5 mg/kg of patient body weight.

43. The method of embodiment 39, wherein the therapeutically effective amount is at least 2.0 mg/kg of patient body weight.

44. The method of embodiment 39, wherein the therapeutically effective amount is at least 2.5 mg/kg of patient body weight.

45. The method of embodiment 39, wherein the therapeutically effective amount is at least 3.0 mg/kg of patient body weight.

46. The method of embodiment 39, wherein the therapeutically effective amount is at least 3.5 mg/kg of patient body weight.

47. The method of embodiment 39, wherein the therapeutically effective amount is at least 4.0 mg/kg of patient body weight.

48. The method of embodiment 39, wherein the therapeutically effective amount is at least 5.0 mg/kg of patient body weight.

49. The method of embodiment 39, wherein the therapeutically effective amount is at least 6.0 mg/kg of patient body weight.

50. The method of embodiment 39, wherein the therapeutically effective amount is at least 7.5 mg/kg of patient body weight.

51. The method of embodiment 39, wherein the therapeutically effective amount is at least 10.0 mg/kg of patient body weight.

52. The method of embodiment 39, wherein the therapeutically effective amount is at least 50 mg.

53. The method of embodiment 39, wherein the therapeutically effective amount is at least 75 mg.

54. The method of embodiment 39, wherein the therapeutically effective amount is at least 100 mg.

55. The method of embodiment 39, wherein the therapeutically effective amount is at least 125 mg.

56. The method of embodiment 39, wherein the therapeutically effective amount is at least 150 mg.

57. The method of embodiment 39, wherein the therapeutically effective amount is at least 175 mg.

58. The method of embodiment 39, wherein the therapeutically effective amount is at least 200 mg.

59. The method of embodiment 39, wherein the therapeutically effective amount is at least 225 mg.

60. The method of embodiment 39, wherein the therapeutically effective amount is at least 250 mg.

61. The method of embodiment 39, wherein the therapeutically effective amount is at least 275 mg.

62. The method of embodiment 39, wherein the therapeutically effective amount is at least 300 mg.

63. The method of embodiment 39, wherein the therapeutically effective amount is at least 325 mg.

64. The method of embodiment 39, wherein the therapeutically effective amount is at least 350 mg.

65. The method of embodiment 39, wherein the therapeutically effective amount is at least 400 mg.

66. The method of embodiment 39, wherein the therapeutically effective amount is at least 425 mg.

67. The method of embodiment 39, wherein the therapeutically effective amount is at least 450 mg.

68. The method of embodiment 39, wherein the therapeutically effective amount is at least 475 mg.

69. The method of embodiment 39, wherein the therapeutically effective amount is at least 500 mg.

70. The method of embodiment 39, wherein the therapeutically effective amount is at least 525 mg.

71. The method of embodiment 39, wherein the therapeutically effective amount is at least 550 mg.

72. The method of embodiment 39, wherein the therapeutically effective amount is at least 575 mg.

73. The method of embodiment 39, wherein the therapeutically effective amount is at least 600 mg.

74. The method of embodiment 39, wherein the superoxide dismutase mimetic is administered within a 15 minute period in an amount of at least 0.67 mg/kg of patient body weight.

75. The method of embodiment 39, wherein the superoxide dismutase mimetic is administered within a 15 minute period in an amount of at least 1.0 mg/kg of patient body weight.

76. The method of embodiment 39, wherein the superoxide dismutase mimetic is administered within a 15 minute period in an amount of at least 1.5 mg/kg of patient body weight.

77. The method of embodiment 39, wherein the superoxide dismutase mimetic is administered within a 15 minute period in an amount of at least 2.0 mg/kg of patient body weight.

78. The method of embodiment 39, wherein the superoxide dismutase mimetic is administered within a 15 minute period in an amount of at least 2.5 mg/kg of patient body weight.

79. The method of embodiment 39, wherein the superoxide dismutase mimetic is administered within a 15 minute period in an amount of at least 3.0 mg/kg of patient body weight.

80. The method of embodiment 39, wherein the superoxide dismutase mimetic is administered within a 30 minute period in an amount of at least 1.5 mg/kg of patient body weight.

81. The method of embodiment 39, wherein the superoxide dismutase mimetic is administered within a 30 minute period in an amount of at least 2.0 mg/kg of patient body weight.

82. The method of embodiment 39, wherein the superoxide dismutase mimetic is administered within a 30 minute period in an amount of at least 2.5 mg/kg of patient body weight.

83. The method of embodiment 39, wherein the superoxide dismutase mimetic is administered within a 30 minute period in an amount of at least 3.0 mg/kg of patient body weight.

84. The method of embodiment 39, wherein the superoxide dismutase mimetic is administered within a 60 minute period in an amount of at least 1.5 mg/kg of patient body weight.

85. The method of embodiment 39, wherein at least 25 mg of the superoxide dismutase mimetic is administered within a 15 minute period.

86. The method of embodiment 39, wherein at least 50 mg of the superoxide dismutase mimetic is administered within a 15 minute period.

87. The method of embodiment 39, wherein at least 50 mg of the superoxide dismutase mimetic is administered within a 30 minute period.

88. The method of embodiment 39, wherein at least 100 mg of the superoxide dismutase mimetic is administered within a 60 minute period.

89. The method of any of embodiments 39-88, wherein the superoxide dismutase mimetic is administered to the patient prior to or simultaneous with the radiation therapy or chemotherapy.

90. The method of any of embodiments 39-88, wherein the superoxide dismutase mimetic is administered to the patient prior to, but not after, the radiation therapy or chemotherapy.

91. The method of any of embodiments 39-88, wherein the superoxide dismutase mimetic is administered to the patient at least 30 minutes prior to the radiation therapy or chemotherapy.

92. The method of any of embodiments 39-88, wherein the superoxide dismutase mimetic is administered to the patient up to three days after the radiation therapy or chemotherapy.

93. The method of any of embodiments 39-88, wherein the superoxide dismutase mimetic is administered to the patient after the radiation therapy or chemotherapy.

94. The method of any of embodiments 39-88, wherein the superoxide dismutase mimetic is administered to the patient up to one week after the radiation therapy or chemotherapy.

95. The method of any of embodiments 39-88, wherein the superoxide dismutase mimetic is administered to the patient up to six weeks after the radiation therapy or chemotherapy.

96. The method of any of embodiments 39-88, wherein the superoxide dismutase mimetic is administered to the patient up to twelve weeks after the radiation therapy or chemotherapy.

97. The method of any of embodiments 39-96, wherein the superoxide dismutase mimetic is administered parenterally.

98. The method of any of embodiments 39-96, wherein the superoxide dismutase mimetic is administered intravenously.

99. The method of any of embodiments 39-98, wherein the superoxide dismutase mimetic is administered as a pharmaceutical composition comprising the superoxide dismutase mimetic corresponding to Formula (GC4419) and a pharmaceutically acceptable carrier.

100. The method of any of embodiments 39-99, wherein the superoxide dismutase mimetic is administered in the form of the unit dose formulation of any of embodiments 1-38.

101. The method of any of embodiments 39-99, wherein the superoxide dismutase mimetic is dissolved in a solution comprising about 0.25 mg/mL to about 3.5 mg/mL superoxide dismutase mimetic and contained in an IV bag.

102. The method of any of embodiments 39-101, wherein X and Y are independently selected from monodentate ligands.

103. The method of any of embodiments 39-102, wherein X and Y are independently selected from the group consisting of aquo ligands, halo ligands, carboxylato ligands, and bicarbonato ligands.

104. The method of any of embodiments 39-103, wherein X and Y are independently selected from aquo ligands and halo ligands.

105. The method of any of embodiments 39-104, wherein X and Y are independently halo ligands.

106. The method of any of embodiments 39-105, wherein X and Y are chloro ligands.

107. The method of any of embodiments 39-106, wherein the superoxide dismutase mimetic corresponds to the dichloro complex form of Formula (GC4419):

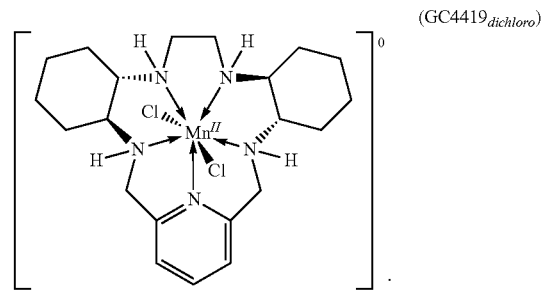

108. A method for treating a human patient for tissue damage resulting from exposure to radiation, the method comprising administering to the patient a therapeutically effective amount of a superoxide dismutase mimetic corresponding to Formula (GC4419):

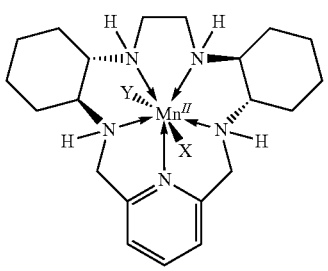

(GC4419)

wherein X and Y are independently neutral or negatively-charged ligands.

109. The method of embodiment 108, wherein the therapeutically effective amount is at least 0.67 mg/kg of patient body weight.

110. The method of embodiment 108, wherein the therapeutically effective amount is at least 1.0 mg/kg of patient body weight.

111. The method of embodiment 108, wherein the therapeutically effective amount is at least 1.5 mg/kg of patient body weight.

112. The method of embodiment 108, wherein the therapeutically effective amount is at least 2.0 mg/kg of patient body weight.

113. The method of embodiment 108, wherein the therapeutically effective amount is at least 2.5 mg/kg of patient body weight.

114. The method of embodiment 108, wherein the therapeutically effective amount is at least 3.0 mg/kg of patient body weight.

115. The method of embodiment 108, wherein the therapeutically effective amount is at least 3.5 mg/kg of patient body weight.

116. The method of embodiment 108, wherein the therapeutically effective amount is at least 4.0 mg/kg of patient body weight.

117. The method of embodiment 108, wherein the therapeutically effective amount is at least 5.0 mg/kg of patient body weight.

118. The method of embodiment 108, wherein the therapeutically effective amount is at least 6.0 mg/kg of patient body weight.

119. The method of embodiment 108, wherein the therapeutically effective amount is at least 7.5 mg/kg of patient body weight.

120. The method of embodiment 108, wherein the therapeutically effective amount is at least 10.0 mg/kg of patient body weight.

121. The method of embodiment 108, wherein the therapeutically effective amount is at least 50 mg.

122. The method of embodiment 108, wherein the therapeutically effective amount is at least 75 mg.

123. The method of embodiment 108, wherein the therapeutically effective amount is at least 100 mg.

124. The method of embodiment 108, wherein the therapeutically effective amount is at least 125 mg.

125. The method of embodiment 108, wherein the therapeutically effective amount is at least 150 mg.

126. The method of embodiment 108, wherein the therapeutically effective amount is at least 175 mg.

127. The method of embodiment 108, wherein the therapeutically effective amount is at least 200 mg.

128. The method of embodiment 108, wherein the therapeutically effective amount is at least 225 mg.

129. The method of embodiment 108, wherein the therapeutically effective amount is at least 250 mg.

130. The method of embodiment 108, wherein the therapeutically effective amount is at least 275 mg.

131. The method of embodiment 108, wherein the therapeutically effective amount is at least 300 mg.

132. The method of embodiment 108, wherein the therapeutically effective amount is at least 325 mg.

133. The method of embodiment 108, wherein the therapeutically effective amount is at least 350 mg.

134. The method of embodiment 108, wherein the therapeutically effective amount is at least 400 mg.

135. The method of embodiment 108, wherein the therapeutically effective amount is at least 425 mg.

136. The method of embodiment 108, wherein the therapeutically effective amount is at least 450 mg.

137. The method of embodiment 108, wherein the therapeutically effective amount is at least 475 mg.

138. The method of embodiment 108, wherein the therapeutically effective amount is at least 500 mg.

139. The method of embodiment 108, wherein the therapeutically effective amount is at least 525 mg.

140. The method of embodiment 108, wherein the therapeutically effective amount is at least 550 mg.

141. The method of embodiment 108, wherein the therapeutically effective amount is at least 575 mg.

142. The method of embodiment 108, wherein the therapeutically effective amount is at least 600 mg.

143. The method of embodiment 108, wherein the superoxide dismutase mimetic is administered within a 15 minute period in an amount of at least 0.67 mg/kg of patient body weight.

144. The method of embodiment 108, wherein the superoxide dismutase mimetic is administered within a 15 minute period in an amount of at least 1.0 mg/kg of patient body weight.

145. The method of embodiment 108, wherein the superoxide dismutase mimetic is administered within a 15 minute period in an amount of at least 1.5 mg/kg of patient body weight.

146. The method of embodiment 108, wherein the superoxide dismutase mimetic is administered within a 15 minute period in an amount of at least 2.0 mg/kg of patient body weight.

147. The method of embodiment 108, wherein the superoxide dismutase mimetic is administered within a 15 minute period in an amount of at least 2.5 mg/kg of patient body weight.

148. The method of embodiment 108, wherein the superoxide dismutase mimetic is administered within a 15 minute period in an amount of at least 3.0 mg/kg of patient body weight.

149. The method of embodiment 108, wherein the superoxide dismutase mimetic is administered within a 30 minute period in an amount of at least 1.5 mg/kg of patient body weight.

150. The method of embodiment 108, wherein the superoxide dismutase mimetic is administered within a 30 minute period in an amount of at least 2.0 mg/kg of patient body weight.

151. The method of embodiment 108, wherein the superoxide dismutase mimetic is administered within a 30 minute period in an amount of at least 2.5 mg/kg of patient body weight.

152. The method of embodiment 108, wherein the superoxide dismutase mimetic is administered within a 30 minute period in an amount of at least 3.0 mg/kg of patient body weight.

153. The method of embodiment 108, wherein the superoxide dismutase mimetic is administered within a 60 minute period in an amount of at least 1.5 mg/kg of patient body weight.

154. The method of embodiment 108, wherein at least 25 mg of the superoxide dismutase mimetic is administered within a 15 minute period.

155. The method of embodiment 108, wherein at least 50 mg of the superoxide dismutase mimetic is administered within a 15 minute period.

156. The method of embodiment 108, wherein at least 50 mg of the superoxide dismutase mimetic is administered within a 30 minute period.

157. The method of embodiment 108, wherein at least 100 mg of the superoxide dismutase mimetic is administered within a 60 minute period.

158. The method of any of embodiments 108-157, wherein the superoxide dismutase mimetic is administered to the patient up to three days after the exposure to radiation.

159. The method of any of embodiments 108-157, wherein the superoxide dismutase mimetic is administered to the patient after the exposure to radiation.

160. The method of any of embodiments 108-157, wherein the superoxide dismutase mimetic is administered to the patient up to one week after the exposure to radiation.

161. The method of any of embodiments 108-157, wherein the superoxide dismutase mimetic is administered to the patient up to six weeks after the exposure to radiation.

162. The method of any of embodiments 108-157, wherein the superoxide dismutase mimetic is administered to the patient up to twelve weeks after the exposure to radiation.

163. The method of any of embodiments 108-162, wherein the exposure to radiation is an accidental radiation exposure, an unintentional radiation exposure, or an intentional radiation exposure.

164. The method of any of embodiments 108-163, wherein the superoxide dismutase mimetic is administered parenterally.

165. The method of any of embodiments 108-163, wherein the superoxide dismutase mimetic is administered intravenously.

166. The method of any of embodiments 108-165, wherein the superoxide dismutase mimetic is administered as a pharmaceutical composition comprising the superoxide dismutase mimetic corresponding to Formula (GC4419) and a pharmaceutically acceptable carrier.

167. The method of any of embodiments 108-166, wherein the superoxide dismutase mimetic is administered in the form of the unit dose formulation of any of embodiments 1-38.

168. The method of any of embodiments 108-166, wherein the superoxide dismutase mimetic is dissolved in a solution comprising about 0.25 mg/mL to about 3.5 mg/mL superoxide dismutase mimetic and contained in an IV bag.

169. The method of any of embodiments 108-168, wherein X and Y are independently selected from monodentate ligands.

170. The method of any of embodiments 108-169, wherein X and Y are independently selected from the group consisting of aquo ligands, halo ligands, carboxylato ligands, and bicarbonato ligands.

171. The method of any of embodiments 108-170, wherein X and Y are independently selected from aquo ligands and halo ligands.

172. The method of any of embodiments 108-171, wherein X and Y are independently halo ligands.

173. The method of any of embodiments 108-172, wherein X and Y are chloro ligands.

174. The method of any of embodiments 108-173, wherein the superoxide dismutase mimetic corresponds to the dichloro complex form of Formula (GC4419):

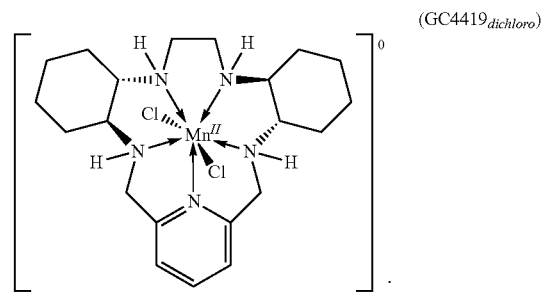

(GC4419$_{dichloro}$)

175. A method of treating a human patient for a disease or condition, the method comprising administering to the patient, within a 15 minute period, at least 25 mg of a superoxide dismutase mimetic corresponding to Formula (GC4419):

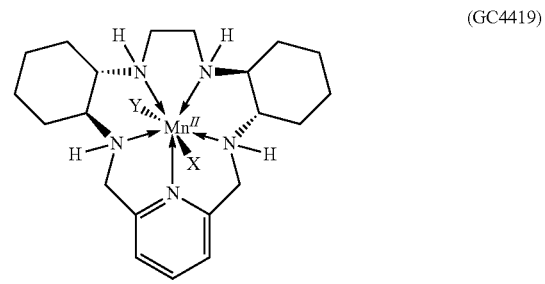

(GC4419)

wherein X and Y are independently neutral or negatively-charged ligands.

176. The method of embodiment 175, wherein at least 50 mg of the superoxide dismutase mimetic is administered within the 15 minute period.

177. The method of embodiment 175, wherein at least 75 mg of the superoxide dismutase mimetic is administered within the 15 minute period.

178. The method of embodiment 175, wherein at least 100 mg of the superoxide dismutase mimetic is administered within the 15 minute period.

179. The method of embodiment 175, wherein at least 125 mg of the superoxide dismutase mimetic is administered within the 15 minute period.

180. The method of embodiment 175, wherein at least 150 mg of the superoxide dismutase mimetic is administered within the 15 minute period.

181. The method of embodiment 175, wherein at least 175 mg of the superoxide dismutase mimetic is administered within the 15 minute period.

182. The method of embodiment 175, wherein at least 200 mg of the superoxide dismutase mimetic is administered within the 15 minute period.

183. The method of embodiment 175, wherein at least 225 mg of the superoxide dismutase mimetic is administered within the 15 minute period.

184. The method of embodiment 175, wherein at least 250 mg of the superoxide dismutase mimetic is administered within the 15 minute period.

185. The method of embodiment 175, wherein at least 275 mg of the superoxide dismutase mimetic is administered within the 15 minute period.

186. The method of embodiment 175, wherein at least 300 mg of the superoxide dismutase mimetic is administered within the 15 minute period.

187. The method of embodiment 175, wherein at least 0.67 mg/kg of body weight is administered within the 15 minute period.

188. The method of embodiment 175, wherein at least 1.0 mg/kg of body weight is administered within the 15 minute period.

189. The method of embodiment 175, wherein at least 1.5 mg/kg of body weight is administered within the 15 minute period.

190. The method of embodiment 175, wherein at least 2.0 mg/kg of body weight is administered within the 15 minute period.

191. The method of embodiment 175, wherein at least 2.5 mg/kg of body weight is administered within the 15 minute period.

192. The method of embodiment 175, wherein at least 3.0 mg/kg of body weight is administered within the 15 minute period.

193. The method of embodiment 175, wherein at least 1.5 mg/kg of body weight is administered within the 30 minute period.

194. The method of embodiment 175, wherein at least 2.0 mg/kg of body weight is administered within the 30 minute period.

195. The method of embodiment 175, wherein at least 2.5 mg/kg of body weight is administered within the 30 minute period.

196. The method of embodiment 175, wherein at least 3.0 mg/kg of body weight is administered within the 30 minute period.

197. The method of embodiment 175, wherein at least 1.5 mg/kg of body weight is administered within the 60 minute period.

198. The method of any of embodiments 175-197, wherein the superoxide dismutase mimetic is administered parenterally.

199. The method of any of embodiments 175-197, wherein the superoxide dismutase mimetic is administered intravenously.

200. The method of any of embodiments 175-199, wherein the superoxide dismutase mimetic is administered as a pharmaceutical composition comprising the superoxide dismutase mimetic corresponding to Formula (GC4419) and a pharmaceutically acceptable carrier.

201. The method of any of embodiments 175-200, wherein the disease or condition is selected from cancer, a cardiovascular disorder, a cerebrovascular disorder, a dermatological disorder, a fibrotic disorder, a gastrointestinal disorder, an immunological disorder, an inflammatory disorder, a metabolic disorder, a neurological disorder, an ophthalmic disorder, a pulmonary disorder, an infectious disease, and combinations thereof.

202. The method of any of embodiments 175-201, wherein the superoxide dismutase mimetic is administered in the form of the unit dose formulation of any of embodiments 1-38.

203. The method of any of embodiments 175-201, wherein the superoxide dismutase mimetic is dissolved in a solution comprising about 0.25 mg/mL to about 3.5 mg/mL superoxide dismutase mimetic and contained in an IV bag.

204. The method of any of embodiments 175-203, wherein X and Y are independently selected from monodentate ligands.

205. The method of any of embodiments 175-204, wherein X and Y are independently selected from the group consisting of aquo ligands, halo ligands, carboxylato ligands, and bicarbonato ligands.

206. The method of any of embodiments 175-205, wherein X and Y are independently selected from aquo ligands and halo ligands.

207. The method of any of embodiments 175-206, wherein X and Y are independently halo ligands.

208. The method of any of embodiments 175-207, wherein X and Y are chloro ligands.

209. The method of any of embodiments 175-208, wherein the superoxide dismutase mimetic corresponds to the dichloro complex form of Formula (GC4419):

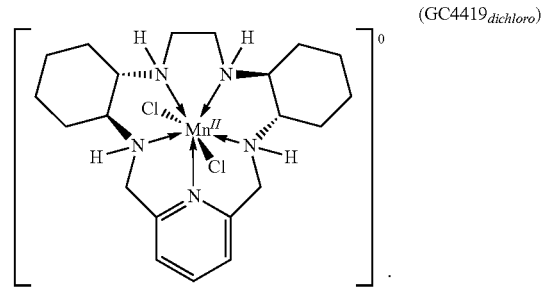

(GC4419$_{dichloro}$)

210. A method of treating a human patient for a disease or condition, the method comprising administering to the patient, within a 15 minute period, at least 50 mg of a superoxide dismutase mimetic corresponding to Formula (GC4419):

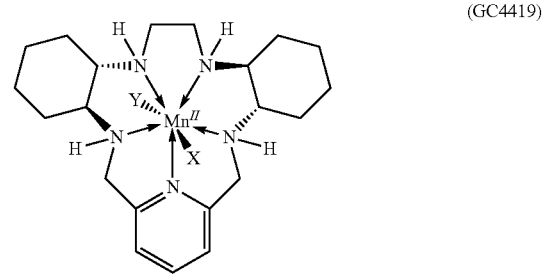

(GC4419)

wherein X and Y are independently neutral or negatively-charged ligands.

211. The method of embodiment 210, wherein at least 75 mg of the superoxide dismutase mimetic is administered within the 15 minute period.

212. The method of embodiment 210, wherein at least 100 mg of the superoxide dismutase mimetic is administered within the 15 minute period.

213. The method of embodiment 210, wherein at least 125 mg of the superoxide dismutase mimetic is administered within the 15 minute period.

214. The method of embodiment 210, wherein at least 150 mg of the superoxide dismutase mimetic is administered within the 15 minute period.

215. The method of embodiment 210, wherein at least 175 mg of the superoxide dismutase mimetic is administered within the 15 minute period.

216. The method of embodiment 210, wherein at least 200 mg of the superoxide dismutase mimetic is administered within the 15 minute period.

217. The method of embodiment 210, wherein at least 225 mg of the superoxide dismutase mimetic is administered within the 15 minute period.

218. The method of embodiment 210, wherein at least 250 mg of the superoxide dismutase mimetic is administered within the 15 minute period.

219. The method of embodiment 210, wherein at least 275 mg of the superoxide dismutase mimetic is administered within the 15 minute period.

220. The method of embodiment 210, wherein at least 300 mg of the superoxide dismutase mimetic is administered within the 15 minute period.

221. The method of embodiment 210, wherein at least 0.67 mg/kg of body weight is administered within the 15 minute period.

222. The method of embodiment 210, wherein at least 1.0 mg/kg of body weight is administered within the 15 minute period.

223. The method of embodiment 210, wherein at least 1.5 mg/kg of body weight is administered within the 15 minute period.

224. The method of embodiment 210, wherein at least 2.0 mg/kg of body weight is administered within the 15 minute period.

225. The method of embodiment 210, wherein at least 2.5 mg/kg of body weight is administered within the 15 minute period.

226. The method of embodiment 210, wherein at least 3.0 mg/kg of body weight is administered within the 15 minute period.

227. The method of any of embodiments 210-226, wherein the superoxide dismutase mimetic is administered parenterally.

228. The method of any of embodiments 210-226, wherein the superoxide dismutase mimetic is administered intravenously.

229. The method of any of embodiments 210-228, wherein the superoxide dismutase mimetic is administered as a pharmaceutical composition comprising the superoxide dismutase mimetic corresponding to Formula (GC4419) and a pharmaceutically acceptable carrier.

230. The method of any of embodiments 210-229, wherein the disease or condition is selected from cancer, a cardiovascular disorder, a cerebrovascular disorder, a dermatological disorder, a fibrotic disorder, a gastrointestinal disorder, an immunological disorder, an inflammatory disorder, a metabolic disorder, a neurological disorder, an ophthalmic disorder, a pulmonary disorder, an infectious disease, and combinations thereof.

231. The method of any of embodiments 210-230, wherein the superoxide dismutase mimetic is administered in the form of the unit dose formulation of any of embodiments 1-38.

232. The method of any of embodiments 210-230, wherein the superoxide dismutase mimetic is dissolved in a solution comprising about 0.25 mg/mL to about 3.5 mg/mL superoxide dismutase mimetic and contained in an IV bag.

233. The method of any of embodiments 210-232, wherein X and Y are independently selected from monodentate ligands.

234. The method of any of embodiments 210-233, wherein X and Y are independently selected from the group consisting of aquo ligands, halo ligands, carboxylato ligands, and bicarbonato ligands.

235. The method of any of embodiments 210-234, wherein X and Y are independently selected from aquo ligands and halo ligands.

236. The method of any of embodiments 210-235, wherein X and Y are independently halo ligands.

237. The method of any of embodiments 210-236, wherein X and Y are chloro ligands.

238. The method of any of embodiments 210-237, wherein the superoxide dismutase mimetic corresponds to the dichloro complex form of Formula (GC4419):

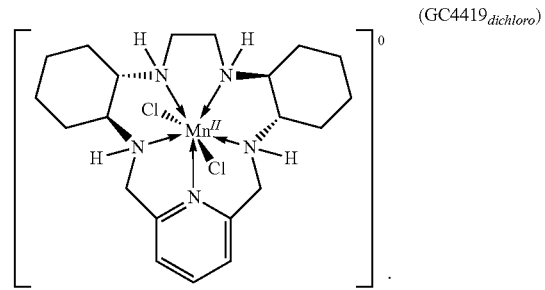

(GC4419$_{dichloro}$)

239. A method of treating a human patient for a disease or condition, the method comprising administering to the patient, within a 30 minute period, at least 50 mg of a superoxide dismutase mimetic corresponding to Formula (GC4419):

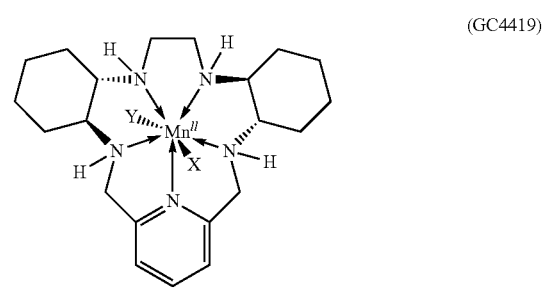

(GC4419)

wherein X and Y are independently neutral or negatively-charged ligands.

240. The method of embodiment 239, wherein at least 75 mg of the superoxide dismutase mimetic is administered within the 30 minute period.

241. The method of embodiment 239, wherein at least 100 mg of the superoxide dismutase mimetic is administered within the 30 minute period.

242. The method of embodiment 239, wherein at least 125 mg of the superoxide dismutase mimetic is administered within the 30 minute period.

243. The method of embodiment 239, wherein at least 150 mg of the superoxide dismutase mimetic is administered within the 30 minute period.

244. The method of embodiment 239, wherein at least 175 mg of the superoxide dismutase mimetic is administered within the 30 minute period.

245. The method of embodiment 239, wherein at least 200 mg of the superoxide dismutase mimetic is administered within the 30 minute period.

246. The method of embodiment 239, wherein at least 225 mg of the superoxide dismutase mimetic is administered within the 30 minute period.

247. The method of embodiment 239, wherein at least 250 mg of the superoxide dismutase mimetic is administered within the 30 minute period.

248. The method of embodiment 239, wherein at least 275 mg of the superoxide dismutase mimetic is administered within the 30 minute period.

249. The method of embodiment 239, wherein at least 300 mg of the superoxide dismutase mimetic is administered within the 30 minute period.

250. The method of embodiment 239, wherein at least 325 mg of the superoxide dismutase mimetic is administered within the 30 minute period.

251. The method of embodiment 239, wherein at least 350 mg of the superoxide dismutase mimetic is administered within the 30 minute period.

252. The method of embodiment 239, wherein at least 375 mg of the superoxide dismutase mimetic is administered within the 30 minute period.

253. The method of embodiment 239, wherein at least 400 mg of the superoxide dismutase mimetic is administered within the 30 minute period.

254. The method of embodiment 239, wherein at least 425 mg of the superoxide dismutase mimetic is administered within the 30 minute period.

255. The method of embodiment 239, wherein at least 450 mg of the superoxide dismutase mimetic is administered within the 30 minute period.

256. The method of embodiment 239, wherein at least 0.67 mg/kg of body weight is administered within the 30 minute period.

257. The method of embodiment 239, wherein at least 1.0 mg/kg of body weight is administered within the 30 minute period.

258. The method of embodiment 239, wherein at least 1.5 mg/kg of body weight is administered within the 30 minute period.

259. The method of embodiment 239, wherein at least 2.0 mg/kg of body weight is administered within the 30 minute period.

260. The method of embodiment 239, wherein at least 2.5 mg/kg of body weight is administered within the 30 minute period.

261. The method of embodiment 239, wherein at least 3.0 mg/kg of body weight is administered within the 30 minute period.

262. The method of embodiment 239, wherein at least 4.0 mg/kg of body weight is administered within the 30 minute period.

263. The method of embodiment 239, wherein at least 6.0 mg/kg of body weight is administered within the 30 minute period.

264. The method of embodiment 239, wherein at least 10.0 mg/kg of body weight is administered within the 30 minute period.

265. The method of any of embodiments 239-264, wherein the superoxide dismutase mimetic is administered parenterally.

266. The method of any of embodiments 239-264, wherein the superoxide dismutase mimetic is administered intravenously.

267. The method of any of embodiments 239-266, wherein the superoxide dismutase mimetic is administered as a pharmaceutical composition comprising the superoxide dismutase mimetic corresponding to Formula (GC4419) and a pharmaceutically acceptable carrier.

268. The method of any of embodiments 239-266, wherein the disease or condition is selected from cancer, a cardiovascular disorder, a cerebrovascular disorder, a dermatological disorder, a fibrotic disorder, a gastrointestinal disorder, an immunological disorder, an inflammatory disorder, a metabolic disorder, a neurological disorder, an ophthalmic disorder, a pulmonary disorder, an infectious disease, and combinations thereof.

269. The method of any of embodiments 239-268, wherein the superoxide dismutase mimetic is administered in the form of the unit dose formulation of any of embodiments 1-38.

270. The method of any of embodiments 239-268, wherein the superoxide dismutase mimetic is dissolved in a solution comprising about 0.25 mg/mL to about 3.5 mg/mL superoxide dismutase mimetic and contained in an IV bag.

271. The method of any of embodiments 239-270, wherein X and Y are independently selected from monodentate ligands.

272. The method of any of embodiments 239-271, wherein X and Y are independently selected from the group consisting of aquo ligands, halo ligands, carboxylato ligands, and bicarbonato ligands.

273. The method of any of embodiments 239-272, wherein X and Y are independently selected from aquo ligands and halo ligands.

274. The method of any of embodiments 239-273, wherein X and Y are independently halo ligands.

275. The method of any of embodiments 239-274, wherein X and Y are chloro ligands.

276. The method of any of embodiments 239-275, wherein the superoxide dismutase mimetic corresponds to the dichloro complex form of Formula (GC4419):

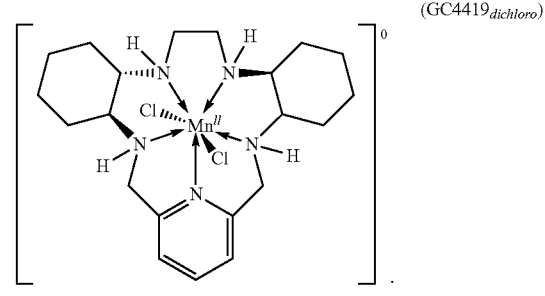

(GC4419$_{dichloro}$)

277. A method of treating a human patient for a disease or condition, the method comprising administering to the patient, within a 60 minute period, at least 100 mg of a superoxide dismutase mimetic corresponding to Formula (GC4419):

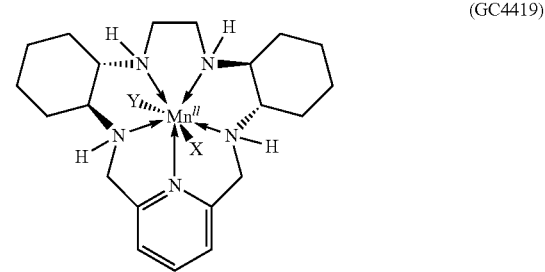

(GC4419)

wherein X and Y are independently neutral or negatively-charged ligands.

278. The method of embodiment 277, wherein at least 125 mg of the superoxide dismutase mimetic is administered within the 60 minute period.

279. The method of embodiment 277, wherein at least 150 mg of the superoxide dismutase mimetic is administered within the 60 minute period.

280. The method of embodiment 277, wherein at least 175 mg of the superoxide dismutase mimetic is administered within the 60 minute period.

281. The method of embodiment 277, wherein at least 200 mg of the superoxide dismutase mimetic is administered within the 60 minute period.

282. The method of embodiment 277, wherein at least 225 mg of the superoxide dismutase mimetic is administered within the 60 minute period.

283. The method of embodiment 277, wherein at least 250 mg of the superoxide dismutase mimetic is administered within the 60 minute period.

284. The method of embodiment 277, wherein at least 275 mg of the superoxide dismutase mimetic is administered within the 60 minute period.

285. The method of embodiment 277, wherein at least 300 mg of the superoxide dismutase mimetic is administered within the 60 minute period.

286. The method of embodiment 277, wherein at least 325 mg of the superoxide dismutase mimetic is administered within the 30 minute period.

287. The method of embodiment 277, wherein at least 350 mg of the superoxide dismutase mimetic is administered within the 30 minute period.

288. The method of embodiment 277, wherein at least 375 mg of the superoxide dismutase mimetic is administered within the 30 minute period.

289. The method of embodiment 277, wherein at least 400 mg of the superoxide dismutase mimetic is administered within the 30 minute period.

290. The method of embodiment 277, wherein at least 425 mg of the superoxide dismutase mimetic is administered within the 30 minute period.

291. The method of embodiment 277, wherein at least 450 mg of the superoxide dismutase mimetic is administered within the 30 minute period.

292. The method of embodiment 277, wherein at least 475 mg of the superoxide dismutase mimetic is administered within the 30 minute period.

293. The method of embodiment 277, wherein at least 500 mg of the superoxide dismutase mimetic is administered within the 30 minute period.

294. The method of embodiment 277, wherein at least 525 mg of the superoxide dismutase mimetic is administered within the 30 minute period.

295. The method of embodiment 277, wherein at least 550 mg of the superoxide dismutase mimetic is administered within the 30 minute period.

296. The method of embodiment 277, wherein at least 575 mg of the superoxide dismutase mimetic is administered within the 30 minute period.

297. The method of embodiment 277, wherein at least 600 mg of the superoxide dismutase mimetic is administered within the 30 minute period.

298. The method of embodiment 277, wherein at least 0.67 mg/kg of body weight is administered within the 60 minute period.

299. The method of embodiment 277, wherein at least 1.0 mg/kg of body weight is administered within the 60 minute period.

300. The method of embodiment 277, wherein at least 1.5 mg/kg of body weight is administered within the 60 minute period.

301. The method of embodiment 277, wherein at least 2.0 mg/kg of body weight is administered within the 60 minute period.

302. The method of embodiment 277, wherein at least 2.5 mg/kg of body weight is administered within the 60 minute period.

303. The method of embodiment 277, wherein at least 3.0 mg/kg of body weight is administered within the 60 minute period.

304. The method of embodiment 277, wherein at least 4.0 mg/kg of body weight is administered within the 60 minute period.

305. The method of embodiment 277, wherein at least 6.0 mg/kg of body weight is administered within the 60 minute period.

306. The method of embodiment 277, wherein at least 10.0 mg/kg of body weight is administered within the 60 minute period.

307. The method of any of embodiments 277-306, wherein the superoxide dismutase mimetic is administered parenterally.

308. The method of any of embodiments 277-306, wherein the superoxide dismutase mimetic is administered intravenously.

309. The method of any of embodiments 277-309, wherein the superoxide dismutase mimetic is administered as a pharmaceutical composition comprising the superoxide dismutase mimetic corresponding to Formula (GC4419) and a pharmaceutically acceptable carrier.

310. The method of any of embodiments 277-309, wherein the disease or condition is selected from cancer, a cardiovascular disorder, a cerebrovascular disorder, a dermatological disorder, a fibrotic disorder, a gastrointestinal disorder, an immunological disorder, an inflammatory disorder, a metabolic disorder, a neurological disorder, an ophthalmic disorder, a pulmonary disorder, an infectious disease, and combinations thereof.

311. The method of any of embodiments 277-310, wherein the superoxide dismutase mimetic is administered in the form of the unit dose formulation of any of embodiments 1-38.

312. The method of any of embodiments 277-310, wherein the superoxide dismutase mimetic is dissolved in a solution comprising about 0.25 mg/mL to about 3.5 mg/mL superoxide dismutase mimetic and contained in an IV bag.

313. The method of any of embodiments 277-312, wherein X and Y are independently selected from monodentate ligands.

314. The method of any of embodiments 277-313, wherein X and Y are independently selected from the group consisting of aquo ligands, halo ligands, carboxylato ligands, and bicarbonato ligands.

315. The method of any of embodiments 277-314, wherein X and Y are independently selected from aquo ligands and halo ligands.

316. The method of any of embodiments 277-315, wherein X and Y are independently halo ligands.

317. The method of any of embodiments 277-316, wherein X and Y are chloro ligands.

318. The method of any of embodiments 277-317, wherein the superoxide dismutase mimetic corresponds to the dichloro complex form of Formula (GC4419):

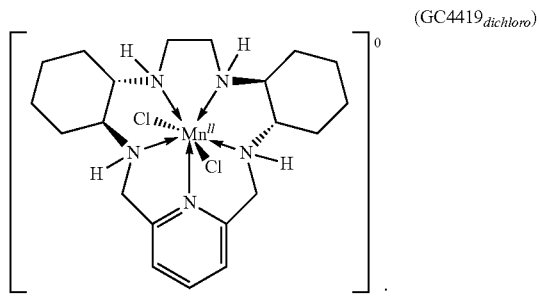

(GC4419$_{dichloro}$)

319. A method of treating a disease or condition in a human patient, the method comprising administering to the patient at least 25 mg of a superoxide dismutase mimetic at a rate of at least 100 mg/hr, wherein the superoxide dismutase mimetic corresponds to Formula (GC4419):

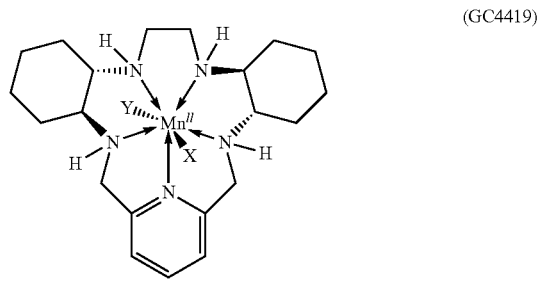

(GC4419)

and X and Y are independently neutral or negatively-charged ligands.

320. The method of embodiment 319, wherein the superoxide dismutase mimetic is administered at a rate of at least 150 mg/hr.

321. The method of embodiment 319, wherein the superoxide dismutase mimetic is administered at a rate of at least 200 mg/hr.

322. The method of embodiment 319, wherein the superoxide dismutase mimetic is administered at a rate of at least 250 mg/hr.

323. The method of embodiment 319, wherein the superoxide dismutase mimetic is administered at a rate of at least 300 mg/hr.

324. The method of embodiment 319, wherein the superoxide dismutase mimetic is administered at a rate of at least 350 mg/hr.

325. The method of embodiment 319, wherein the superoxide dismutase mimetic is administered at a rate of at least 400 mg/hr.

326. The method of embodiment 319, wherein the superoxide dismutase mimetic is administered at a rate of at least 450 mg/hr.

327. The method of embodiment 319, wherein the superoxide dismutase mimetic is administered at a rate of at least 500 mg/hr.

328. The method of embodiment 319, wherein the superoxide dismutase mimetic is administered at a rate of at least 550 mg/hr.

329. The method of embodiment 319, wherein the superoxide dismutase mimetic is administered at a rate of at least 600 mg/hr.

330. The method of embodiment 319, wherein at least 50 mg of the superoxide dismutase mimetic is administered to the patient.

331. The method of embodiment 319, wherein at least 75 mg of the superoxide dismutase mimetic is administered to the patient.

332. The method of embodiment 319, wherein at least 100 mg of the superoxide dismutase mimetic is administered to the patient.

333. The method of embodiment 319, wherein at least 125 mg of the superoxide dismutase mimetic is administered to the patient.

334. The method of embodiment 319, wherein at least 150 mg of the superoxide dismutase mimetic is administered to the patient.

335. The method of embodiment 319, wherein at least 175 mg of the superoxide dismutase mimetic is administered to the patient.

336. The method of embodiment 319, wherein at least 200 mg of the superoxide dismutase mimetic is administered to the patient.

337. The method of embodiment 319, wherein at least 225 mg of the superoxide dismutase mimetic is administered to the patient.

338. The method of embodiment 319, wherein at least 250 mg of the superoxide dismutase mimetic is administered to the patient.

339. The method of embodiment 319, wherein at least 275 mg of the superoxide dismutase mimetic is administered to the patient.

340. The method of embodiment 319, wherein at least 300 mg of the superoxide dismutase mimetic is administered to the patient.

341. The method of embodiment 319, wherein at least 325 mg of the superoxide dismutase mimetic is administered to the patient.

342. The method of embodiment 319, wherein at least 350 mg of the superoxide dismutase mimetic is administered to the patient.

343. The method of embodiment 319, wherein at least 375 mg of the superoxide dismutase mimetic is administered to the patient.

344. The method of embodiment 319, wherein at least 400 mg of the superoxide dismutase mimetic is administered to the patient.

345. The method of embodiment 319, wherein at least 425 mg of the superoxide dismutase mimetic is administered to the patient.

346. The method of embodiment 319, wherein at least 450 mg of the superoxide dismutase mimetic is administered to the patient.

347. The method of embodiment 319, wherein at least 475 mg of the superoxide dismutase mimetic is administered to the patient.

348. The method of embodiment 319, wherein at least 500 mg of the superoxide dismutase mimetic is administered to the patient.

349. The method of embodiment 319, wherein at least 525 mg of the superoxide dismutase mimetic is administered to the patient.

350. The method of embodiment 319, wherein at least 550 mg of the superoxide dismutase mimetic is administered to the patient.

351. The method of embodiment 319, wherein at least 575 mg of the superoxide dismutase mimetic is administered to the patient.

352. The method of embodiment 319, wherein at least 600 mg of the superoxide dismutase mimetic is administered to the patient.

353. The method of any one of embodiments 319, wherein the administration occurs within a 15 minute time period.

354. The method of any one of embodiments 319, wherein the administration occurs within a 30 minute time period.

355. The method of any one of embodiments 319, wherein the administration occurs within a 60 minute time period.

356. The method of any of embodiments 319-355, wherein the superoxide dismutase mimetic is administered parenterally.

357. The method of any of embodiments 319-355, wherein the superoxide dismutase mimetic is administered intravenously.

358. The method of any of embodiments 319-357, wherein the superoxide dismutase mimetic is administered as a pharmaceutical composition comprising the superoxide dismutase mimetic corresponding to Formula (GC4419) and a pharmaceutically acceptable carrier.

359. The method of any of embodiments 319-358, wherein the disease or condition is selected from cancer, a cardiovascular disorder, a cerebrovascular disorder, a dermatological disorder, a fibrotic disorder, a gastrointestinal disorder, an immunological disorder, an inflammatory disorder, a metabolic disorder, a neurological disorder, an ophthalmic disorder, a pulmonary disorder, an infectious disease, and combinations thereof.

360. The method of any of embodiments 319-359, wherein the superoxide dismutase mimetic is administered in the form of the unit dose formulation of any of embodiments 1-38.

361. The method of any of embodiments 319-359, wherein the superoxide dismutase mimetic is dissolved in a solution comprising about 0.25 mg/mL to about 3.5 mg/mL superoxide dismutase mimetic and contained in an IV bag.

362. The method of any of embodiments 319-361, wherein X and Y are independently selected from monodentate ligands.

363. The method of any of embodiments 319-362, wherein X and Y are independently selected from the group consisting of aquo ligands, halo ligands, carboxylato ligands, and bicarbonato ligands.

364. The method of any of embodiments 319-363, wherein X and Y are independently selected from aquo ligands and halo ligands.

365. The method of any of embodiments 319-364, wherein X and Y are independently halo ligands.

366. The method of any of embodiments 319-365, wherein X and Y are chloro ligands.

367. The method of any of embodiments 319-366, wherein the superoxide dismutase mimetic corresponds to the dichloro complex form of Formula (GC4419):

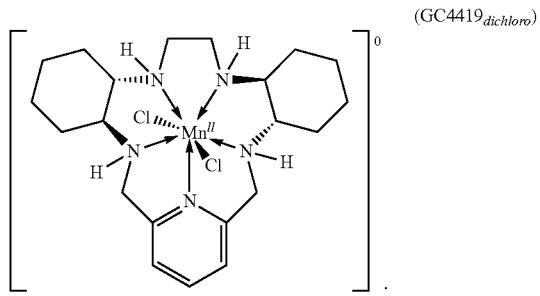

368. A method of treating a disease or condition in a human patient, the method comprising administering to the patient a superoxide dismutase mimetic to provide an exposure as measured by an area under the curve (AUC) of at least 4,000 ng-h/mL as calculated from the measurement of the superoxide dismutase mimetic concentration in the patient's plasma, wherein the superoxide dismutase mimetic corresponds to Formula (GC4419):

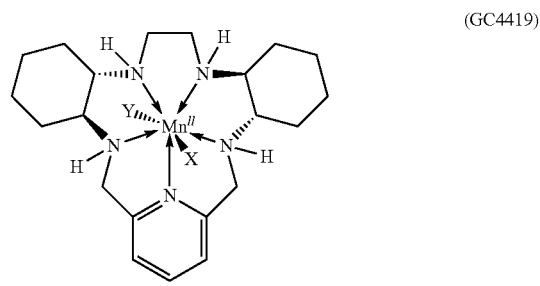

and X and Y are independently neutral or negatively-charged ligands.

369. The method of embodiment 368, wherein the administration provides an exposure as measured by an area under the curve (AUC) of at least 5,000 ng-h/mL as calculated from the measurement of the superoxide dismutase mimetic concentration in the patient's plasma.

370. The method of embodiment 368, wherein the administration provides an exposure as measured by an area under the curve (AUC) of at least 7,500 ng-h/mL as calculated from the measurement of the superoxide dismutase mimetic concentration in the patient's plasma.

371. The method of embodiment 368, wherein the administration provides an exposure as measured by an area under the curve (AUC) of at least 10,000 ng-h/mL as calculated from the measurement of the superoxide dismutase mimetic concentration in the patient's plasma.

372. The method of embodiment 368, wherein the administration provides an exposure as measured by an area under the curve (AUC) of at least 12,500 ng-h/mL as calculated from the measurement of the superoxide dismutase mimetic concentration in the patient's plasma.

373. The method of embodiment 368, wherein the administration provides an exposure as measured by an area under the curve (AUC) of at least 15,000 ng-h/mL as calculated from the measurement of the superoxide dismutase mimetic concentration in the patient's plasma.

374. The method of embodiment 368, wherein the administration provides an exposure as measured by an area under the curve (AUC) of at least 17,500 ng-h/mL as calculated from the measurement of the superoxide dismutase mimetic concentration in the patient's plasma.

375. The method of embodiment 368, wherein the administration provides an exposure as measured by an area under the curve (AUC) of at least 20,000 ng-h/mL as calculated from the measurement of the superoxide dismutase mimetic concentration in the patient's plasma.

376. The method of embodiment 368, wherein the administration provides an exposure as measured by an area under the curve (AUC) of at least 22,500 ng-h/mL as calculated from the measurement of the superoxide dismutase mimetic concentration in the patient's plasma.

377. The method of embodiment 368, wherein the administration provides an exposure as measured by an area under the curve (AUC) of at least 25,000 ng-h/mL as calculated from the measurement of the superoxide dismutase mimetic concentration in the patient's plasma.

378. The method of embodiment 368, wherein the administration provides an exposure as measured by an area under the curve (AUC) of at least 27,500 ng-h/mL as calculated from the measurement of the superoxide dismutase mimetic concentration in the patient's plasma.

379. The method of embodiment 368, wherein the administration provides an exposure as measured by an area under the curve (AUC) of at least 30,000 ng-h/mL as calculated from the measurement of the superoxide dismutase mimetic concentration in the patient's plasma.

380. The method of embodiment 368, wherein the administration provides an exposure as measured by an area under the curve (AUC) of at least 32,500 ng-h/mL as calculated from the measurement of the superoxide dismutase mimetic concentration in the patient's plasma.

381. The method of embodiment 368, wherein the administration provides an exposure as measured by an area under the curve (AUC) of at least 35,000 ng-h/mL as calculated from the measurement of the superoxide dismutase mimetic concentration in the patient's plasma.

382. The method of embodiment 368, wherein the administration provides an exposure as measured by an area under the curve (AUC) of at least 37,500 ng-h/mL as calculated from the measurement of the superoxide dismutase mimetic concentration in the patient's plasma.

383. The method of embodiment 368 wherein the administration provides an exposure as measured by an area under the curve (AUC) of at least 40,000 ng-h/mL as calculated from the measurement of the superoxide dismutase mimetic concentration in the patient's plasma.

384. The method of embodiment 368, wherein the administration provides an exposure as measured by an area under the curve (AUC) of at least 42,500 ng-h/mL as calculated from the measurement of the superoxide dismutase mimetic concentration in the patient's plasma.

385. The method of embodiment 368, wherein the administration provides an exposure as measured by an area under the curve (AUC) of at least 45,000 ng-h/mL as calculated from the measurement of the superoxide dismutase mimetic concentration in the patient's plasma.

386. The method of embodiment 368, wherein the administration provides an exposure as measured by an area under the curve (AUC) of at least 47,500 ng-h/mL as calculated from the measurement of the superoxide dismutase mimetic concentration in the patient's plasma.

387. The method of embodiment 368, wherein the administration provides an exposure as measured by an area under the curve (AUC) of at least 50,000 ng-h/mL as calculated from the measurement of the superoxide dismutase mimetic concentration in the patient's plasma.

388. The method of any of embodiments 368-387, wherein the superoxide dismutase mimetic is administered parenterally.

389. The method of any of embodiments 368-387, wherein the superoxide dismutase mimetic is administered intravenously.

390. The method of any of embodiments 368-389, wherein the superoxide dismutase mimetic is administered as a pharmaceutical composition comprising the superoxide dismutase mimetic corresponding to Formula (GC4419) and a pharmaceutically acceptable carrier.

391. The method of any of embodiments 368-390, wherein the disease or condition is selected from cancer, a cardiovascular disorder, a cerebrovascular disorder, a dermatological disorder, a fibrotic disorder, a gastrointestinal disorder, an immunological disorder, an inflammatory disorder, a metabolic disorder, a neurological disorder, an ophthalmic disorder, a pulmonary disorder, an infectious disease, and combinations thereof.

392. The method of any of embodiments 368-391, wherein the superoxide dismutase mimetic is administered in the form of the unit dose formulation of any of embodiments 1-38.

393. The method of any of embodiments 368-391, wherein the superoxide dismutase mimetic is dissolved in a solution comprising about 0.25 mg/mL to about 3.5 mg/mL superoxide dismutase mimetic and contained in an IV bag.

394. The method of any of embodiments 368-393, wherein X and Y are independently selected from monodentate ligands.

395. The method of any of embodiments 368-394, wherein X and Y are independently selected from the group consisting of aquo ligands, halo ligands, carboxylato ligands, and bicarbonato ligands.

396. The method of any of embodiments 368-395, wherein X and Y are independently selected from aquo ligands and halo ligands.

397. The method of any of embodiments 368-396, wherein X and Y are independently halo ligands.

398. The method of any of embodiments 368-397, wherein X and Y are chloro ligands.

399. The method of any of embodiments 368-398, wherein the superoxide dismutase mimetic corresponds to the dichloro complex form of Formula (GC4419):

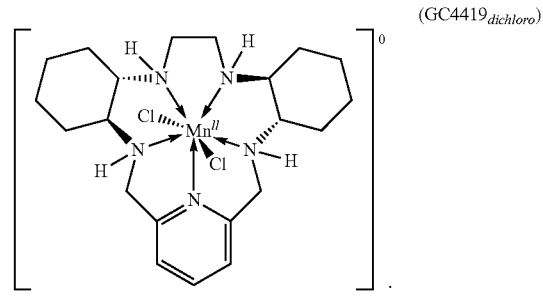

400. An article of manufacture, comprising packaging material and contained within said packaging material a parenteral formulation for treating a disease or condition or for protecting tissue against damage resulting from exposure to a cancer treatment in a patient in need thereof, wherein said parenteral formulation comprises a unit dose formulation of any of embodiments 1-38 and wherein said packaging material comprises a label or package insert with instructions for parenterally administering the dose to the patient.

401. The article of manufacture of embodiment 400, wherein the parenteral formulation is in solution form, comprising about 20 mg/mL superoxide dismutase mimetic, the formulation being a unit dose in a container.

402. The article of manufacture of embodiment 400, wherein the parenteral formulation is in solution form, comprising about 17.5 mg/mL superoxide dismutase mimetic, the formulation being a unit dose in a container.

403. The article of manufacture of embodiment 400, wherein the parenteral formulation is in solution form, comprising about 15 mg/mL superoxide dismutase mimetic, the formulation being a unit dose in a container.

404. The article of manufacture of embodiment 400, wherein the parenteral formulation is in solution form, comprising about 12.5 mg/mL superoxide dismutase mimetic, the formulation being a unit dose in a container.

405. The article of manufacture of embodiment 400, wherein the parenteral formulation is in solution form, comprising about 10 mg/mL superoxide dismutase mimetic, the formulation being a unit dose in a container.

406. The article of manufacture of embodiment 400, wherein the parenteral formulation is in solution form, comprising about 7.5 mg/mL superoxide dismutase mimetic, the formulation being a unit dose in a container.

407. The article of manufacture of embodiment 400, wherein the parenteral formulation is in solution form, comprising about 5 mg/mL superoxide dismutase mimetic, the formulation being a unit dose in a container.

408. The article of manufacture of any of embodiments 400-407, wherein the disease or condition is selected from cancer, a cardiovascular disorder, a cerebrovascular disorder, a dermatological disorder, a fibrotic disorder, a gastrointestinal disorder, an immunological disorder, an inflammatory disorder, a metabolic disorder, a neurological disorder, an ophthalmic disorder, a pulmonary disorder, an infectious disease, and combinations thereof.

409. The method of any of embodiments 400-408, wherein X and Y are independently selected from monodentate ligands.

410. The pharmaceutical composition of any of embodiments 400-409, wherein X and Y are independently selected from the group consisting of aquo ligands, halo ligands, carboxylato ligands, and bicarbonato ligands.

411. The pharmaceutical composition of any of embodiments 400-410, wherein X and Y are independently selected from aquo ligands and halo ligands.

412. The pharmaceutical composition of any of embodiments 400-411, wherein X and Y are independently halo ligands.

413. The pharmaceutical composition of any of embodiments 400-412, wherein X and Y are chloro ligands.

414. The article of manufacture of any of embodiments 400-413, wherein the superoxide dismutase mimetic corresponds to the dichloro complex form of Formula (GC4419):

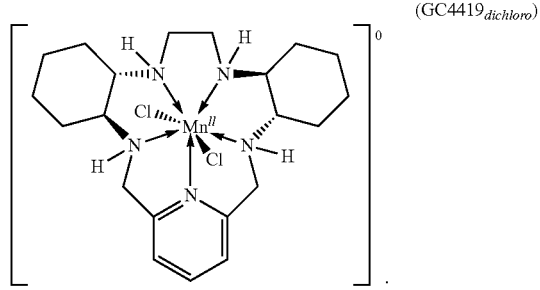

415. A pharmaceutical composition in solution form comprising about 0.25 mg/mL to about 3.5 mg/mL of a superoxide dismutase mimetic, the composition being a unit dose in a container for intravenous administration, wherein the superoxide dismutase mimetic corresponds to Formula (GC4419):

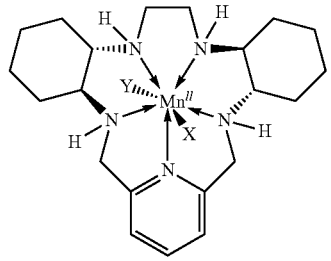

and X and Y are independently neutral or negatively-charged ligands.

416. The pharmaceutical composition of embodiment 415, which comprises about 0.25 mg/mL of the superoxide dismutase mimetic.

417. The pharmaceutical composition of embodiment 415, which comprises about 0.5 mg/mL of the superoxide dismutase mimetic.

418. The pharmaceutical composition of embodiment 415, which comprises about 0.75 mg/mL of the superoxide dismutase mimetic.

419. The pharmaceutical composition of embodiment 415, which comprises about 1.0 mg/mL of the superoxide dismutase mimetic.

420. The pharmaceutical composition of embodiment 415, which comprises about 1.25 mg/mL of the superoxide dismutase mimetic.

421. The pharmaceutical composition of embodiment 415, which comprises about 1.5 mg/mL of the superoxide dismutase mimetic.

422. The pharmaceutical composition of embodiment 415, which comprises about 1.75 mg/mL of the superoxide dismutase mimetic.

423. The pharmaceutical composition of embodiment 415, which comprises about 2.0 mg/mL of the superoxide dismutase mimetic.

424. The pharmaceutical composition of embodiment 415, which comprises about 2.25 mg/mL of the superoxide dismutase mimetic.

425. The pharmaceutical composition of embodiment 415, which comprises about 2.5 mg/mL of the superoxide dismutase mimetic.

426. The pharmaceutical composition of embodiment 415, which comprises about 2.75 mg/mL of the superoxide dismutase mimetic.

427. The pharmaceutical composition of embodiment 415, which comprises about 3.0 mg/mL of the superoxide dismutase mimetic.

428. The method of any of embodiments 415-427, wherein X and Y are independently selected from monodentate ligands.

429. The pharmaceutical composition of any of embodiments 415-428, wherein X and Y are independently selected from the group consisting of aquo ligands, halo ligands, carboxylato ligands, and bicarbonato ligands.

430. The pharmaceutical composition of any of embodiments 415-429, wherein X and Y are independently selected from aquo ligands and halo ligands.

431. The pharmaceutical composition of any of embodiments 415-430, wherein X and Y are independently halo ligands.

432. The pharmaceutical composition of any of embodiments 415-431, wherein X and Y are chloro ligands.

433. The pharmaceutical composition of any of embodiments 415-432, wherein the superoxide dismutase mimetic corresponds to the dichloro complex form of Formula (GC4419):

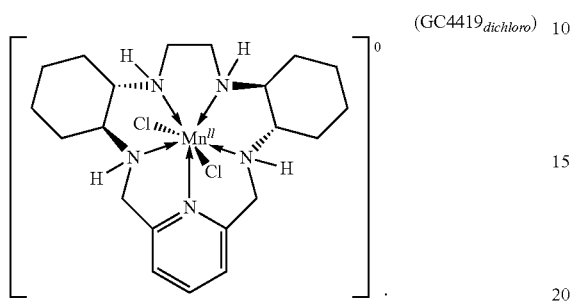

(GC4419$_{dichloro}$)

The foregoing embodiments are illustrative only, and do not represent any limitation on the scope of the invention. Various modifications and combinations of the features disclosed are apparent to those of skill in the art based upon the above disclosure, and are also within the scope of the invention.

Having described the invention in detail, it will be apparent that modifications and variations are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Chemical and Crystal Structures of GC4403 and GC4419

As noted above, the chemical structures of GC4403 and GC4419 are identical other than they possess mirror image chirality; that is, the enantiomeric structures are non-superimposable. GC4403 has four chiral carbon centers that exist in the R-absolute configuration and GC4419 has four chiral carbon atoms that are in the S-absolute configuration:

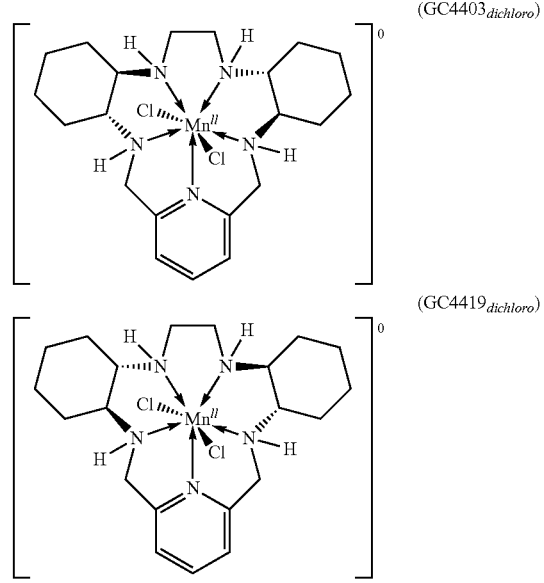

(GC4403$_{dichloro}$)

(GC4419$_{dichloro}$)

Figure 2:
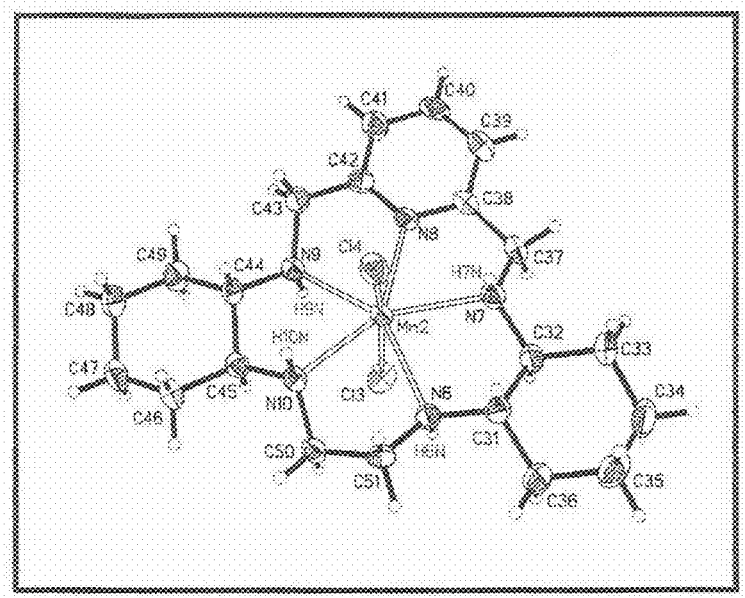
FIG. 2 is the Ortep drawing for the GC4419 complex based on single-crystal X-ray diffraction showing the 50% probability ellipsoids for the non-hydrogen atoms and the hydrogen atoms bound to the secondary amines (see Example 1).

The single crystal x-ray structure for GC4403 has been reported in the literature and is shown in FIG. 1. Riley, D. P., Schall, O. F., 2007, *Advances in Inorganic Chemistry*, 59: 233-263. The single crystal x-ray structure for GC4419 has likewise been determined and is shown in FIG. 2.

Example 2

Synthesis of GC4403 and GC4419

The GC4403 and GC4419 complexes were synthesized by the template method previously reported for GC4403. In the case of GC4403, the complex was synthesized via the template route described in the literature using the chiral R,R-1,2-diamminocyclohexane. Salvemini, D., et. al., 1999, *Science*, 286: 304-6; Aston, K., Rath, N., Naik, A., Slomczynska, U., Schall, O. F., Riley, D. P., 2001, *Inorg. Chem.*, 40(8), 1779-89. For the synthesis of GC4419 the identical method was utilized except that the chiral S,S-1,2-diamminocyclohexane replaces R,R-1,2-diamminocyclohexane in the synthesis.

Example 3

Physiochemical Properties of GC4403 and GC4419

The GC4403 and GC4419 complexes possess identical physicochemical properties including stability, reactivity with non-chiral reagents, electronic spectra, solubility in non-chiral media, and reactivity with superoxide. A summary of relevant physicochemical properties are listed in Table 1.

TABLE 1

Physical and Chemical Features of GC4419 and GC4403

| Parameter | GC4403 Value | GC4419 Value |
| --- | --- | --- |
| Solubility in Distilled Water | 30 mg/mL | 30 mg/mL |
| Electronic spectra in 240-700 nm range | $\lambda_{max}$ @ 264 nm $\epsilon = 3984$ | $\lambda_{max}$ @ 264 nm $\epsilon = 3984$ |

TABLE 1-continued

Physical and Chemical Features of GC4419 and GC4403

| Parameter | GC4403 Value | GC4419 Value |
|---|---|---|
| Catalytic rate constant for the dismutation of superoxide[†] | $k_{cat}$ = $1.2 \times 10^{+7}$ $M^{-1}$ $sec^{-1}$ at pH = 7.4 | $k_{cat}$ = $1.2 \times 10^{+7}$ $M^{-1}$ $sec^{-1}$ at pH = 7.4 |
| Solubility in 26 mM bicarbonate buffered saline, at 25° C., pH 8.3 | 20 mg/mL | 20 mg/mL |
| Melting Range | 375° C. | 375° C. |
| Molecular Weight | 483.39 | 483.39 |
| Appearance | White to off-white powder | White to off-white powder |
| Kinetic Stability[‡] | $k_{diss}$ = 0.135 $M^{-1}$ $s^{-1}$ | $k_{diss}$ = 0.135 $M^{-1}$ $s^{-1}$ |

[†]See Riley, D. P., Weiss, R. H., River, W., J., 1991, *Anal. Biochem.*, 196: 344-49.
[‡]The kinetic stability is a measure of the rate of loss of the ligand from Mn(II); i.e., the dissociation of the Mn(II) ion from the ligand is a second-order reaction which is first-order in [H⁺] and first-order in [Mn(II) complex]. The $k_{diss}$ value is the second-order rate constant for this dissociation reaction at any pH in water. Riley, D. P., Henke, S., Lennon, P. J., Weiss, R. H., Neuman, W. L., Rivers, W. J., Aston, K. W., Sample, K. R., Rahman, H., Ling, C-S., Shieh, J. J., Busch, D. H., Szulbinski, W., 1996, *Inorg. Chem.*, 35: 5213.

Example 4

Anti-Proliferative Activity (In Vitro)

Figure 3:
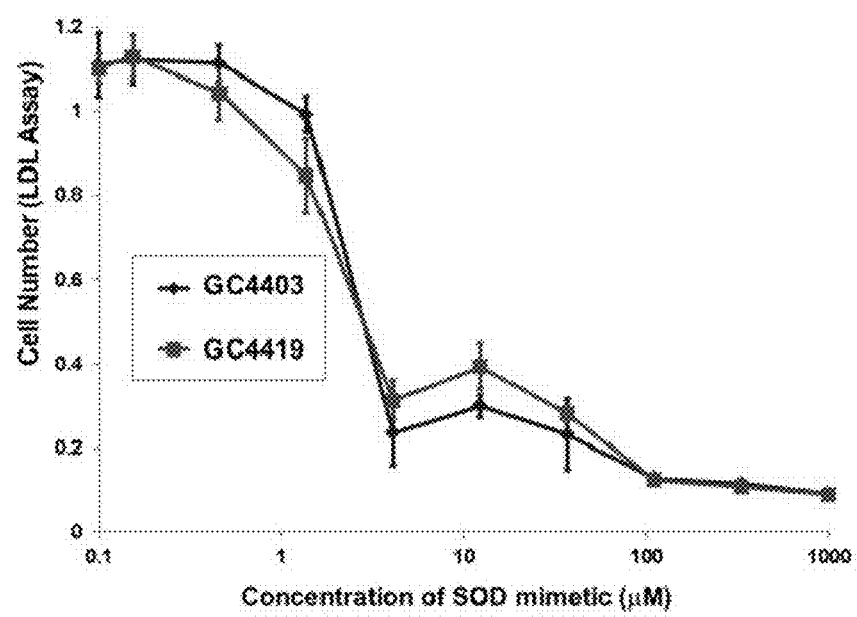
FIG. 3 is a graph showing the dose-dependent decrease in the proliferation of HEK-293 cells when treated with GC4403 or GC4419.

Materials and Methods: HEK-293 (CRL-1573) cells were obtained from ATCC and cultured according to ATCC instructions. Complete growth medium consisted of RPMI 1640 supplemented to 10% with fetal bovine serum (FBS). All cell incubations were at 37° C. in 95% air: 5% $CO_2$. Two days before the start of a proliferation experiment, $10^3$ HEK-293 cells in exponential growth phase were plated into each well of a 96-well plate. To synchronize cell division, the cells were maintained in complete growth medium for 24 hours at which time the cell monolayers were rinsed once with growth medium without FBS and then incubated overnight in media without FBS. The next morning GC4419 or GC4403 in complete growth medium or complete growth medium alone was added. The plates were incubated for 72 hour, after which time cell numbers were determined using an LDH assay kit. "Cell number" on FIG. 3 represents absorbance at 490 nm.

Results: Both SOD mimetics, GC4403 and GC4419, caused an equivalent dose-dependent decrease in the proliferation of HEK-293 cells (FIG. 3). In addition, there was no significant difference between the compounds in their anti-proliferative effects.

Example 5

Animal Safety Studies

When compared to GC4403, GC4419 was significantly safer in animal safety models and human studies, while achieving similar plasma exposures for similar mass doses and IV infusion rates (i.e., significantly more compound can be administered in a significantly shorter infusion time).

Safety Studies in Dog
GC4403 7-Day IV Toxicity

GC4403 in 26 mM sodium bicarbonate/0.9% sodium chloride was administered to beagle dogs (4/sex/group) IV (slow bolus injection over at least 1 minute) at dosages of 0, 1, 3 or 6 mg/kg/day for 7 days. There was no mortality during the study. Clinical signs immediately after dose administration were observed at ≥3 mg/kg/day and included scratching, mild to moderate facial swelling, raised red areas on the ventral body surface and partial closing of the eyes. At 6 mg/kg/day, animals also had tremors, abnormal stance and gait, inability to stand and prostration. Generally, clinical signs had resolved by two hours after dose administration. As the study progressed, some clinical signs (tremors, inability to stand, prostration and abnormal stance and gait) lessened slightly. Males at ≥3 mg/kg/day and females at 6 mg/kg/day had an initial body weight loss during the first three days of the study accompanied by decreased mean food consumption. Males and females at 6 mg/kg/day did not gain weight during the study as compared to animals in the other groups, which did gain weight. At the end of the dosing period, all treated groups had a trend of lower red blood cell count, hemoglobin and hematocrit, and lower total white blood cell counts. The lower white cell counts correlated with lower absolute neutrophil and eosinophil counts at ≤3 mg/kg/day, which were, however, within the normal historical values for these parameters. At necropsy, there were no changes in organ weights compared to control animals nor were there macroscopic or microscopic changes in any organs with the exception of fibrosis in the heart of one male at 3 mg/kg/day and 1 male at 6 mg/kg/day.

Based on the results of this study, the no observed toxic event level (NOTEL) for the administration of GC4403 IV by slow bolus injection to the dog for 7 days was 3 mg/kg/day.

GC4403 28-Day IV Toxicity

GC4403 was evaluated in a Good Laboratory Practice (GLP)-regulated study in beagle dogs. GC4403 was administered intravenously (IV) via slow bolus dose, once daily, to beagle dogs for 28 consecutive days. GC4403 was administered IV into the cephalic vein (0.5 mL/kg) to 3 groups of dogs (4 animals/sex/group) at dosages of 1.0, 3.0 and 6.0 mg/kg with a fourth group receiving vehicle (26 mM sodium bicarbonate in normal saline). No animals died during the treatment, although in the 6.0 mg/kg group tremors, abnormal stance and gait and inability to stand were noted immediately post-dose, but these clinical signs were or short duration and lessened in incidence and severity as the study proceeded. There were no test article-related differences in group mean hematology, coagulation, or clinical chemistry parameters or urinalysis parameters after 28 days of treatment in any dosing group. At necropsy on day 29, there were neither test-article related gross macroscopic findings nor test-article-related differences in organ weight. No test-article-related histopathological lesions were present. There were no test-article-related electrocardiology (ECG) effects when evaluated on day 27.

Based on the results and observations of this study, the no observed toxic effect level (NOTEL) for GC4403 administered IV to beagle dogs for 28 consecutive days was 3.0 mg/kg/day, whereas the no observed adverse effect level (NOAEL) was 1 mg/kg/day.

14-Day Repeat Dose Toxicity of GC4419 in Dog

GC4419 was evaluated in a GLP study in beagle dogs. GC4419 was administered intravenously (IV) over 15 minutes, once daily, to beagle dogs for 14 consecutive days. GC4419 was administered IV into the cephalic vein (4 mL/kg) to 3 groups of dogs (4 animals/sex/group) at dosages of 2.5, 5.0 and 7.5 mg/kg with a fourth group receiving vehicle (26 mM sodium bicarbonate in normal saline). No animals died during the treatment and there were few effects of GC4419 at up to 7.5 mg/kg, with ataxia noted in one male and one female, and a convulsion in one female, all in the 7.5 mg/kg groups. All animals recovered from these effects. There were no test-article-related differences in group mean hematology, coagulation, or clinical chemistry parameters or urinalysis parameters after 14 days of treatment in any dosing group. At necropsy on day 15, there were neither test-article related gross macroscopic findings nor test-article-related differences in organ weight. No test-article-related histopathological lesions were present.

Based on the infrequent clinical signs at 7.5 mg/kg/day, the NOAEL was determined to 5.0 mg/kg/day.

Safety Studies in Rat

Rat GC4403 7-Day Intravenous Toxicity

GC4403 was Studied in a GLP toxicology study in which it was administered in 26 mM sodium bicarbonate/0.9% sodium chloride to SD rats (10/sex/group) IV (slow bolus 1 mL/kg/minute) at dosages of 0, 1, 3 or 10 mg/kg/day for 7 days (On Day 1, 1/10 male rats receiving 10 mg/kg/day died). The dosage was therefore decreased to 8 mg/kg/day on Day 2 for all surviving animals for the remainder of the study, and the original 10 mg/kg/day group was re-designated as the 8 mg/kg/day group. On Day 4, two females from the 8 mg/kg/day group also died. Clinical signs immediately following dose administration of 8 mg/kg/day were twitching, labored breathing, body drop and prostration. At the scheduled 1-hour observation time, animals appeared normal. Males and females given 8 mg/kg/day had decreased body weight gains, which were accompanied by decreased food consumption in the males only. When compared to controls, rats administered 8 mg/kg/day had significantly higher glucose, alkaline phosphatase, and ALT and triglyceride values. Males at ≥3 mg/kg/day and females at 8 mg/kg/day had significantly higher calcium values. Surviving rats were sacrificed, and all rats sacrificed or found dead were necropsied. No compound-related changes in organ weights were observed at necropsy. There were no macroscopic or microscopic findings in any tissues and examination of the injection sites revealed that the compound was non-irritating.

Based on the results of this study, the no observed toxic event level (NOTEL) for the administration of GC4403 IV by slow bolus injection to the rat for 7 days was 3 mg/kg/day.

Rat GC4403 28-Day IV Toxicology

GC4403 was evaluated in a 28-day GLP study in Sprague-Dawley rats. GC4403 was administered to rats (10/sex/group) as slow-bolus IV injections at dosages of 0, 1, 3 or 6 mg/kg/day for 28 days. The control (0 dose) group received vehicle (26 mM sodium bicarbonate in normal saline). Evaluations for compound-related effects were based on clinical observations, body weight, food consumption, hematology and clinical chemistry parameters, functional observation battery, organ weights and gross and microscopic postmortem examinations. There were no compound-related changes in organ weights or macroscopic or microscopic pathology. Based on the results of this study, the NOTEL for GC4403, when administered to rats for 28 days as an IV infusion was 3 mg/kg/day.

Rat GC4419 7-Day IV Study

A GLP toxicity study with GC4419 in bicarbonate buffer was performed. Rats (5/sex/group) were administered GC4419 as a 15 minute IV injection (4 mL/kg) at 0, 5, 10 or 15 mg/kg for 7 consecutive days. The control group received bicarbonate buffer. Evaluations for compound-related effects were based on clinical observations, body weight and food consumption. There were no deaths during the study and there were no signs of significant compound effects at any dosage. Some mild decreases in body weight that reached approximately 10% by Day 8 and mild decreased food consumption were observed in males given 15 mg/kg/day. The NOTEL was found to be 15 mg/kg for both males and females.

Rat GC4419 14-Day IV Study

GC4419 was evaluated in a 14-day GLP study in rats. GC4419 was administered to rats (10/sex/group) as 15 minute IV injections at dosages of 0, 5, 10 or 20 (15) mg/kg/day for 14 days. The control group received vehicle (sodium citrate in normal saline). Due to mortality at 20 mg/kg/day, the high dose group was decreased to 15 mg/kg/day on Day 3. Evaluations for compound-related effects were based on clinical observations, body weight, food consumption, hematology and clinical chemistry parameters, functional observation battery, organ weights and gross and microscopic postmortem examinations. Several rats died on Days 1 or 2 at 20 mg/kg and these deaths were considered to be compound-related and the dose level was reduced to 15 mg/kg/day beginning day 3. There were no compound-related changes in organ weights or macroscopic or microscopic pathology. Based on the results of this study the NOAEL for GC4419 when administered to rats for 14 days as a 15 minute IV infusion was 15 mg/kg/day.

Example 6

Efficacy of SOD Mimetics on Radiation-Induced Oral Mucositis

GC4403 and GC4419 were studied in a hamster model of oral mucositis (OM). Irradiation of the hamster cheek pouch induces lesions that are histologically similar to OM that which occurs clinically, and develop and resolve at a similar rate to radiation-induced OM in humans. Male Syrian golden hamsters (8/group) received vehicle, GC4403 (30 mg/kg) or GC4419 (3-30 mg/kg) in 26 mM sodium bicarbonate-buffered saline by intraperitoneal injection 30 minutes prior to irradiation and 12 hrs post-irradiation. The animals received 40 Gy radiation localized to the everted cheek pouch and were evaluated every second day for the development of inflammation at the radiation site. Inflammation was rated on a scale of 0 (normal) to 5 (total ulceration of pouch) by a trained observer, blinded to the treatment protocol.

Figure 4:
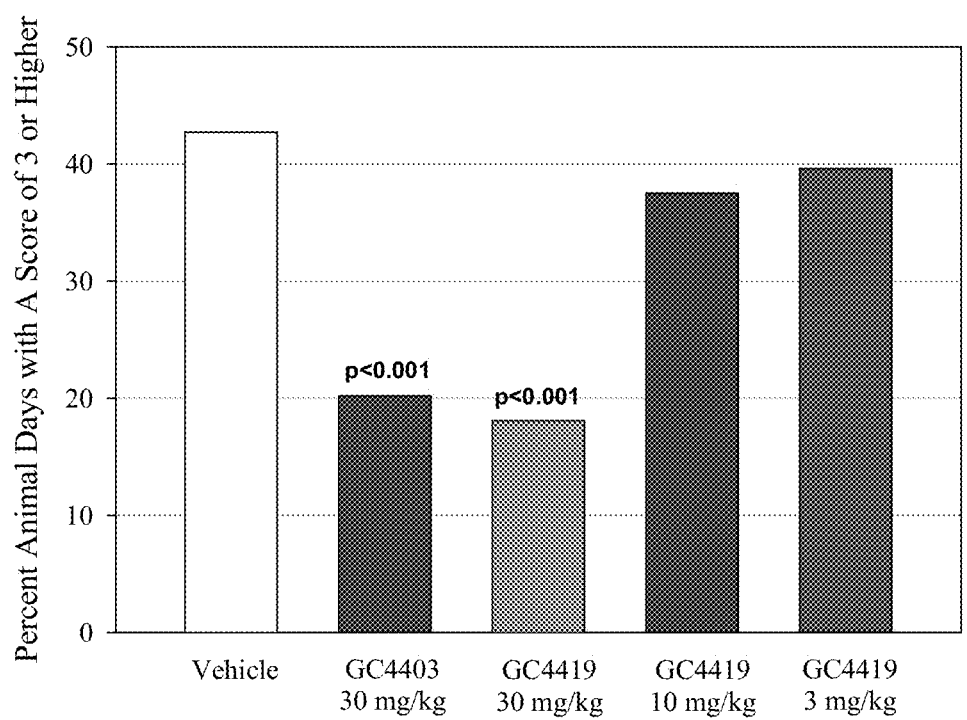
FIG. 4 is a graph showing the effect of GC4403 and GC4419 on radiation-induced oral mucositis in hamster.

All doses of GC4419 administered prior to irradiation prevented the development of grade 3 or greater OM (FIG. 4). GC4419 at 30 mg/kg reduced OM by 57% while GC4403 at 30 mg/kg reduced grade 3 and greater OM by 52%. All hamsters treated with GC4403 or GC4419 showed a weight gain (approximately 15% compared to vehicle) over the course of the experiment (28 days), presumably because of decreased oral pain and inflammation making it easier to eat and drink.

Example 7

Efficacy of SOD Mimetics on Plasma TNF-α in the Collagen Induced Arthritis Model Male Lewis rats (160-180 g) were used for this study. Collagen induced arthritis (CIA) was induced as follows: Bovine type II collagen (CII; Sigma) was dissolved in 0.1 M acetic acid at 2 mg/mL by stirring overnight at 4 C. Rats were immunized with an emulsion of 2 mg/mL CII in incomplete Freund's adjuvant (IFA; Sigma). The emulsion was prepared by homogenizing one part CII into one part IFA at 4 C. On day 1, rats were injected intradermally at the base of the tail with 100 μL of the emulsion. On day 21, a second injection of CII in IFA was administered at the base of the tail. GC4403 and GC4419 were prepared fresh, dissolved in 26 mM sodium bicarbonate buffered saline (Vehicle). All drugs were given by intraperitoneal injection at 1 mL/kg. Animals were randomly divided into groups (n=10 per group). GC4403 and GC4419 were administered once daily at 2, 5 and 10 mg/kg from days 25 through 35.

Time course studies have indicated that plasma levels peak at day 35 in the CIA model, and remain elevated for approximately 5-6 days. TNF-α levels were measured from plasma on day 35. The assay was conducted using a colorimetric ELISA kit (Calbiochem-Novabiochem) having a detection limit of 5 pg/mL. Values were expressed as mean±standard error of the mean of 10 observations. Data sets were examined by one-way ANOVA followed by a Bonferroni post-hoc test for multiple comparisons. A p-value of less than 0.05 was considered significant.

Figure 5:
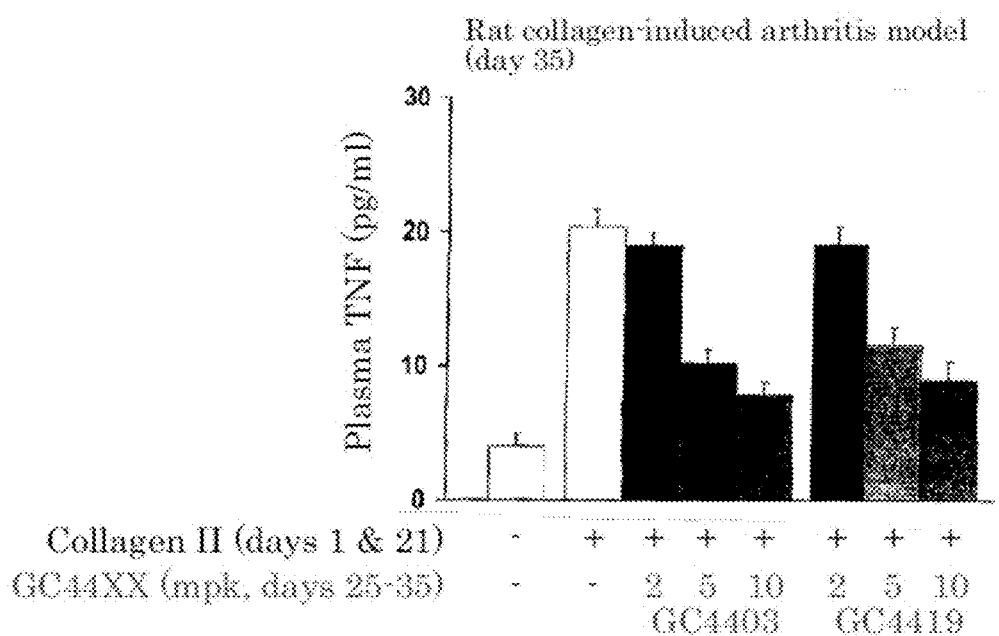
FIG. 5 is a graph showing the effect of GC4403 and GC4419 on TNFα levels in mouse collagen-induced arthritis.

At day 35, the levels of TNF-α were significantly elevated in the plasma of Vehicle-treated CIA-rats. Both GC4403 and GC4419 attenuated TNF-α production in an equivalent manner (FIG. 5). The 2 mg/kg doses did not significantly reduce TNF-α production. For both agents, the 5 mg/kg and 10 mg/kg doses significantly reduced TNF-α production.

Example 8

Human Clinical Safety for GC4419

A human clinical trial entitled, "A Double-Blind, Placebo-Controlled, Single Rising Dose Study to Evaluate the Safety and Tolerability and Determine the Pharmacokinetics of M40419 Administered as a 15-Minute Intravenous Infusion in Healthy Subjects," was conducted on 54 subjects. This was a single center, randomized, placebo-controlled, sequential panel, single dose safety, tolerability, and pharmacokinetic study of GC4419 administered as a 75-mL IV infusion over 15 minutes in escalating doses of 10 mg, 15 mg, 22 mg, 33 mg, 50 mg, 75 mg, and 112 mg. The study consisted of two phases: the first phase was a dose escalation with six subjects (four active and two placebo) in each cohort to determine a Maximum Tolerated Dose (MTD); the second phase was a repeat of the MTD dose in 12 subjects (eight active drug and four placebo) to confirm the MTD or safety of highest dose tested. The study population was comprised of 54 healthy male and female subjects (36 males, 18 females) between the ages of 18 and 50 years considered eligible on the basis of inclusion and exclusion criteria. There were four active and two placebo subjects for each dose level in the escalating dose phase of the study, and eight active and four placebo subjects for the confirmation of MTD phase.

All subjects receiving a dose of study medication were evaluated for safety. The safety of the drug product was assessed based on: treatment-emergent adverse events (TE-AEs), clinical laboratory evaluations, vital signs, 12-lead electrocardiograms (ECGs) and standard ECG parameters including PR, QRS, QT, and QTc intervals.

Of the 54 subjects who were randomized to receive study medication, 54 (100%) completed the study in accordance with the study protocol. No subjects withdrew prematurely from the study. Protocol deviations were minor, and none were thought to affect the pharmacokinetic or safety outcomes of the study. Upon visual inspection of demographic and baseline characteristics data, no clinically relevant differences among treatment groups were apparent.

A total of 125 Treatment Emergent Adverse Events (TE-AEs) emerged post-dose in 37 subjects. Overall, 7 of 18 subjects (38.9%) who received placebo and 30 of 36 subjects (83.3%) who received trial material experienced at least one TEAE. TEAEs occurred in 12 body systems, the most common in subjects that received the trial material being nervous system disorders, general disorders and administration site conditions, and gastrointestinal disorders. The most common adverse events in trial material treated subjects were paresthesia, circumoral paresthesia, and nausea (an analysis of origin of the paresthesia side-effect is discussed below). The majority of TEAEs reported were mild in severity (104 of 125 events, 83.2%). Nineteen events (19 of 125 events, 15.2%), were moderate, and two events were severe (2 of 125 events, 1.6%). Both events reported as severe in intensity were nausea, reported in the 75 mg and 112 mg treated groups. Both events resolved spontaneously. Of the 125 total TEAEs reported, 105 events (84.0%), occurring in 37 of 54 total subjects, were judged by the Investigator as having either an uncertain or probable relationship to study medication. Seven of these events (5.6%) occurred in placebo treated subjects, and 99 of the 105 events (94.3%) occurred in study medication treated subjects.

The 50-mg dose was determined to be the MTD following completion of confirmation of the MTD panel. The 75 mg dose was initially determined in the dose escalation phase to be the MTD, however based on the character and grading of adverse events that occurred during the confirmation of MTD phase, the decision was made to define the MTD as 50 mg. Upon visual inspection of the data, the incidence of AEs seemed to correlate with trial material dose, although no formal statistical analysis was performed on the data.

No deaths or serious adverse events occurred during the course of the study. No subject discontinued prematurely due to an adverse event. Two dose-limiting toxicities (DLT) occurred, and each prompted the identification of the MTD as the next lower dose. The DLTs included nausea in a subject who received 112 mg of study material in the dose escalation phase (initially defining the MTD as 75 mg), and nausea with mild hypotension in a subject who received 75 mg of study material in the confirmation of MTD phase (defining the final MTD as 50 mg). Both events were judged by the Investigator as probably related to study medication.

Vital signs, ECGs, and physical examination data did not reveal any clinically significant trends or changes from baseline, nor were there any distinguishable differences between placebo-treated and study material-treated subjects at any dose of the study drug.

The overall conclusions of the study were as follows:

GC4419 was excreted unchanged in the urine and over 48 hours accounted for less than 20% of the dose administered. The renal pathway does not appear to be the major route of elimination for GC4419 in humans.

The 50-mg dose of GC4419, administered as an intravenous infusion over 15 minutes was determined to be the maximum no effect tolerated dose.

Adverse events following GC4419 administration were generally mild. The two dose-limiting toxicities reported did not warrant discontinuation of dose escalation, but led to the final identification of the maximum tolerated dose as 50 mg. No serious adverse events were reported, and none of the subjects discontinued prematurely due to an adverse event.

Overall, single intravenous doses of GC4419 from 10 mg to 50 mg were safe and well tolerated with no adverse events.

In this Phase 1 study, the results indicate that single doses of GC4419 up to 112 mg were tolerated by healthy subjects with no serious adverse events.

Example 9

Human Clinical Safety for GC4403

In a Phase 1 randomized, double-blind, placebo-controlled single rising dose safety, tolerability and pharmacokinetics study, 54 healthy male and female subjects were dosed from 2.2 to 25 mg of GC4403 administered intravenously over 30 minutes. Disposition of GC4403 is multi-exponential and follows linear pharmacokinetics with generally proportional increases in AUC and $C_{max}$ with increasing dose over the dose ranges studied. The terminal elimination half-life is approximately 1.5 hours. GC4403 is excreted unchanged in the urine and accounts for approximately 9 to 17% of the dose administered. No significant cardiovascular or vital sign effects, no significant physical examination abnormalities, and no significant abnormalities in routine clinical laboratory assessments were observed. Facial tingling, generalized tingling, paraesthesias and facial warmth were reported in a dose responsive manner, occurring at the 16.7 and 25 mg GC4403 doses. No adverse events labeled as severe and no serious adverse events were seen in this study.

Table 2 summarizes the clinical findings of signs and symptoms of toxicity observed in subjects in this Phase 1a trial. An official MTD was not established in this trial but given the dose dependent findings and the extent of findings at the 25 mg dose, subsequent clinical studies with GC4403 were held to a top dose of 20 mg infused over a period of 30 minutes.

In this first Phase 1 study, the results indicate that single doses of M40403 up to 25 mg were tolerated by healthy subjects with no severe adverse events. The numbers of subjects experiencing adverse events in the study seen at each dose are listed in Table 2, and as noted a maximum tolerated dose (MTD) was not attained. The maximum dose to be administered was 25 mg. No significant cardiovascular effects, no significant physical examination abnormalities, and no significant abnormalities in routine clinical laboratory assessments were observed. No severe or serious adverse events were reported. One episode of conjunctivitis (2.2 mg group), one episode of lightheadedness (3.3 mg group), one episode of headache (16.7 group), and one episode of injection site pain (16.7 mg group) were reported as moderate in intensity. All other treatment-emergent adverse events were reported as mild in intensity. Facial warmth, tingling, tingling mouth, and paraesthesias, all rated mild in intensity, were reported in a dose-responsive manner occurring at the 16.7 and 25 mg doses. The facial warmth, tingling, tingling mouth, and paraesthesias typically began during or shortly after the infusion, and lasted up to 3 to 4 hours.

TABLE 2

Treatment-Emergent Adverse Events Reported for GC4403
Phase 1 Safety and Tolerability Trial

| | Treatment | | | | | | | |
|---|---|---|---|---|---|---|---|---|
| | Placebo | 2.2 mg | 3.3 mg | 4.9 mg | 7.4 mg | 11.1 mg | 16.7 mg | 25.0 mg |
| | # of Subjects Dosed | | | | | | | |
| | 16 | 4 | 4 | 4 | 4 | 4 | 4 | 12 |
| Any Event N (%) | 5 (27.8) | 1 (25) | 2 (50) | 1 (25) | 3 (75) | 0 (0) | 2 (50) | 10 (87.3) |
| Tingling Mouth | 0 (0) | 0 (0) | 0 (0) | 0 (0) | 0 (0) | 0 (0) | 0 (0) | 5 (41.7) |
| Injection Site Pain | 0 (0) | 0 (0) | 0 (0) | 0 (0) | 0 (0) | 0 (0) | 1 (25) | 4 (33.3) |
| Tingling | 0 (0) | 0 (0) | 0 (0) | 0 (0) | 0 (0) | 0 (0) | 2 (50) | 3 (25.0) |
| Lightheadedness | 0 (0) | 0 (0) | 1 (25) | 0 (0) | 0 (0) | 0 (0) | 0 (0) | 2 (16.7) |
| Drowsiness | 0 (0) | 0 (0) | 0 (0) | 0 (0) | 0 (0) | 0 (0) | 0 (0) | 1 (8.3) |
| Feeling Drunk | 0 (0) | 0 (0) | 0 (0) | 0 (0) | 0 (0) | 0 (0) | 0 (0) | 1 (8.3) |
| Facial Warmth | 0 (0) | 0 (0) | 0 (0) | 0 (0) | 0 (0) | 0 (0) | 0 (0) | 1 (8.3) |
| Headache | 3 (16.7) | 0 (0) | 0 (0) | 0 (0) | 1 (25) | 0 (0) | 1 (25) | 1 (8.3) |
| Inj. Site Pressure | 0 (0) | 0 (0) | 0 (0) | 0 (0) | 1 (25) | 0 (0) | 0 (0) | 1 (8.3) |
| Inj. Site Reaction | 0 (0) | 0 (0) | 1 (25) | 0 (0) | 0 (0) | 0 (0) | 0 (0) | 1 (8.3) |
| Paresthesia | 0 (0) | 0 (0) | 0 (0) | 0 (0) | 0 (0) | 0 (0) | 0 (0) | 1 (8.3) |
| Skin Tightness | 0 (0) | 0 (0) | 0 (0) | 0 (0) | 0 (0) | 0 (0) | 0 (0) | 1 (8.3) |
| Taste Perversion | 0 (0) | 0 (0) | 0 (0) | 0 (0) | 0 (0) | 0 (0) | 0 (0) | 1 (8.3) |
| Discolored Urine | 0 (0) | 0 (0) | 0 (0) | 0 (0) | 0 (0) | 0 (0) | 0 (0) | 1 (8.3) |
| Conjunctivitis | 0 (0) | 1 (25) | 0 (0) | 0 (0) | 0 (0) | 0 (0) | 0 (0) | 0 (0) |
| Cough | 0 (0) | 0 (0) | 0 (0) | 0 (0) | 0 (0) | 0 (0) | 1 (25) | 0 (0) |

TABLE 3

Average Area-Under-the-Curve (AUC) Plasma Exposures in Human Phase 1 Studies

| Dose (mg) | GC4403 $AUC_{0-24\,h}$† (ng-hr/mL) | GC4419 $AUC_{0-inf}$ (ng-hr/mL) |
|---|---|---|
| 2.2 | 184 | — |
| 3.3 | 310 | — |
| 4.9 | 453 | — |
| 7.4 | 595 | — |
| 10 | — | 741 |
| 11.1 | 1050 | — |
| 15 | — | 1298 |
| 16.7 | 1508 | — |
| 22 | — | 2003 |
| 25 | 2556 | — |
| 33 | — | 3193 |
| 50 | — | 4558 |
| 75 | — | 6488 |
| 112 | — | 10350 |

†At the tested doses GC4403 was not detectable in plasma past 24 hr (LOD = 1 ng/mL)

As part of the conduct of the Phase 1a clinical studies for GC4403 and GC4419 described in the Examples herein, plasma samples were collected for measuring the concentration of parent compounds (GC4403 and GC4419) after intravenous infusion. Table 3 illustrates the pharmacokinetic parameter, area under the curve (AUC), representing the total exposure of the subject to the drugs over time. Importantly, the results indicate that equivalent mass doses of GC4419 and GC4403 should yield substantially equivalent AUC values in humans. Because of the enhanced safety of GC4419 over GC4403 (reflected in the higher doses safely achieved with GC4419), almost 4-fold greater AUCs were achieved with GC4419 compared to GC4403, 10350 ng-hr/mL vs. 2556 ng-hr/mL, respectively.

What is claimed is:

1. A method of reducing tissue damage or toxicity resulting from radiation therapy, chemotherapy or a combination thereof, the tissue damage or toxicity being modulated by superoxide dismutase activity in a human patient, the method comprising parenterally administering to the patient 25 to 450 mg of a superoxide dismutase mimetic at a rate of at least 100 mg/hr, wherein the superoxide dismutase mimetic corresponds to Formula (GC4419):

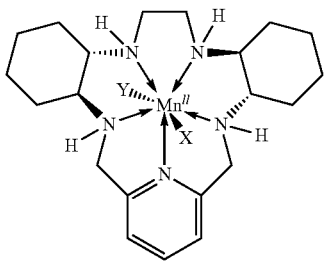

(GC4419)

and X and Y are independently halo ligands.

2. The method of claim 1, wherein 50 mg of the superoxide dismutase mimetic is administered to the patient.

3. The method of claim 1, wherein 100 mg of the superoxide dismutase mimetic is administered to the patient.

4. The method of claim 1, wherein the superoxide dismutase mimetic is administered intravenously.

5. The method of claim 1, wherein the superoxide dismutase mimetic is administered as a pharmaceutical composition comprising the superoxide dismutase mimetic corresponding to Formula (GC4419) and a pharmaceutically acceptable carrier.

6. The method of claim 1, wherein the superoxide dismutase mimetic is administered in the form of the unit dose formulation of claim.

7. The method of claim 1, wherein the superoxide dismutase mimetic is dissolved in a solution comprising about 0.25 mg/mL to about 3.5 mg/mL superoxide dismutase mimetic and contained in an IV bag.

8. The method of claim 1, wherein X and Y are chloro ligands.

9. The method of claim 1, wherein 25 to 200 mg of the superoxide dismutase mimetic is administered to the patient.

10. The method of claim 1, wherein 25 mg of the superoxide dismutase mimetic is administered to the patient.

11. The method of claim 1, wherein 75 mg of the superoxide dismutase mimetic is administered to the patient.

12. The method of claim 1, wherein the superoxide dismutase mimetic is administered at a rate of 100 mg/hr.

13. The method of claim 1, wherein the superoxide dismutase mimetic is administered at a rate of 200 mg/hr.

14. The method of claim 12, wherein the superoxide dismutase mimetic is administered at a rate of 450 mg/hr.

15. The method of claim 1, wherein 25 mg of the superoxide dismutase mimetic is administered at a rate of 100 mg/hr.

16. The method of claim 1, wherein 50 mg of the superoxide dismutase mimetic is administered at a rate of 200 mg/hr.

17. The method of claim 1, wherein the administration provides an exposure as measured by an area under the curve (AUC) of 4,000 to 10,000 ng-h/mL as calculated from the measurement of the superoxide dismutase mimetic concentration in the patient's plasma.

18. The method of claim 1, wherein the administration occurs within a 15 minute time period.

19. The method of claim 1, wherein the administration occurs within a 30 minute time period.

20. The method of claim 1, wherein the administration occurs within a 60 minute time period.

21. The method of claim 1, wherein the tissue damage or toxicity results from the administration of radiation therapy to the patient.

22. The method of claim 1, wherein the tissue damage or toxicity results from the administration of chemotherapy to the patient.

* * * * *